US011844605B2

(12) United States Patent
Stewart et al.

(10) Patent No.: US 11,844,605 B2
(45) Date of Patent: Dec. 19, 2023

(54) SYSTEM, METHOD AND BIOMARKERS FOR AIRWAY OBSTRUCTION

(71) Applicant: The Research Foundation for the State University of new York, Brooklyn, NY (US)

(72) Inventors: Mark Stewart, East Hanover, NJ (US); Richard Kollmar, Bronx, NY (US); Jason Lazar, Roslyn Heights, NY (US)

(73) Assignee: The Research Foundation for SUNY, Binghamton, NY (US)

( * ) Notice: Subject to any disclaimer, the term of this patent is extended or adjusted under 35 U.S.C. 154(b) by 378 days.

(21) Appl. No.: 16/478,100

(22) PCT Filed: Nov. 10, 2017

(86) PCT No.: PCT/US2017/061099
§ 371 (c)(1),
(2) Date: Jul. 15, 2019

(87) PCT Pub. No.: WO2018/089789
PCT Pub. Date: May 17, 2018

(65) Prior Publication Data
US 2020/0405184 A1     Dec. 31, 2020

Related U.S. Application Data

(60) Provisional application No. 62/420,308, filed on Nov. 10, 2016.

(51) Int. Cl.
*A61B 5/08* (2006.01)
*A61B 5/369* (2021.01)
(Continued)

(52) U.S. Cl.
CPC .......... *A61B 5/0826* (2013.01); *A61B 5/0004* (2013.01); *A61B 5/0205* (2013.01);
(Continued)

(58) Field of Classification Search
CPC ... A61B 5/0826; A61B 5/4818; A61B 5/0205; A61B 5/349; A61B 5/352; A61B 5/7225; A61B 5/7246; A61B 5/389
See application file for complete search history.

(56) References Cited

U.S. PATENT DOCUMENTS 3,942,513 A   3/1976   Frank
3,950,799 A   4/1976   Frank
(Continued)

FOREIGN PATENT DOCUMENTS

WO   WO-2005018737 A1 *  3/2005   ........... A61B 5/4815

OTHER PUBLICATIONS

"A. Bartolo, et al. Analysis of diaphragm EMG signals: comparison of gating vs. subtraction for removal of ECG contamination. Jun. 1996. Journal of Applied Physiology. vol. 80, Issue 6. pp. 1898-1900" (Year: 1996).*

(Continued)

*Primary Examiner* — Nathan J Jenness
*Assistant Examiner* — Severo Antonio P. Lopez
(74) *Attorney, Agent, or Firm* — Hoffberg & Associates; Steven M. Hoffberg

(57) ABSTRACT

Two biomarkers are provided for obstructive apnea. A first biomarker determines amplitude and timing of inspiratory efforts from a bioelectric signal. The respiratory rate is compared with a normal pre-detection rate, and the amplitude of the effort is compared with a normal amplitude. The obstructive apnea is likely present if a series of inspiratory efforts are above a normal amplitude and with increasing amplitude, but at a normal rate. A second biomarker determines heart rate and respiratory rate. A normal lower threshold for heartbeat interval is established, and if subthreshold events occur (short RR intervals), a commencement time for each sequence of subthreshold events is compared for a (Continued)

respiratory rate-normalized window. If the number of sub-threshold events exceeds a minimum for the window, obstructive apnea is likely present.

19 Claims, 17 Drawing Sheets

(51) Int. Cl.
*A61B 5/389* (2021.01)
*A61B 5/352* (2021.01)
*A61B 5/316* (2021.01)
*A61B 5/00* (2006.01)
*A61B 5/0205* (2006.01)

(52) U.S. Cl.
CPC .............. *A61B 5/316* (2021.01); *A61B 5/352* (2021.01); *A61B 5/369* (2021.01); *A61B 5/389* (2021.01); *A61B 5/7225* (2013.01); *A61B 5/7246* (2013.01); *A61B 5/7405* (2013.01); *A61B 5/746* (2013.01)

(56) References Cited

U.S. PATENT DOCUMENTS

| | | | |
|---|---|---|---|
| 4,033,332 A | 7/1977 | Hardway, Jr. et al. | |
| 4,169,462 A | 10/1979 | Strube | |
| 4,197,856 A | 4/1980 | Northrop | |
| 4,289,142 A | 9/1981 | Kearns | |
| 4,308,872 A | 1/1982 | Watson et al. | |
| 4,350,166 A | 9/1982 | Mobarry | |
| 4,381,788 A | 5/1983 | Douglas | |
| 4,387,722 A | 6/1983 | Kearns | |
| 4,391,279 A | 7/1983 | Stein | |
| 4,403,215 A | 9/1983 | Hofmann et al. | |
| 4,422,458 A | 12/1983 | Kravath | |
| 4,446,869 A | 5/1984 | Knodle | |
| 4,474,185 A | 10/1984 | Diamond | |
| 4,475,559 A | 10/1984 | Horn | |
| 4,506,626 A | 3/1985 | Schurman et al. | |
| 4,506,666 A | 3/1985 | Durkan | |
| 4,558,708 A | 12/1985 | Labuda et al. | |
| RE32,180 E | 6/1986 | Lewiner et al. | |
| 4,595,016 A | 6/1986 | Fertig et al. | |
| D284,697 S | 7/1986 | Brefka | |
| 4,617,525 A | 10/1986 | Lloyd | |
| 4,630,614 A | 12/1986 | Atlas | |
| 4,648,407 A | 3/1987 | Sackner | |
| 4,657,026 A | 4/1987 | Tagg | |
| 4,686,975 A | 8/1987 | Naimon et al. | |
| 4,686,999 A | 8/1987 | Snyder et al. | |
| 4,694,839 A | 9/1987 | Timme | |
| 4,715,367 A | 12/1987 | Crossley | |
| 4,724,844 A | 2/1988 | Rafelson | |
| 4,732,159 A | 3/1988 | Kraman | |
| 4,736,749 A | 4/1988 | Lundback | |
| 4,745,925 A | 5/1988 | Dietz | |
| 4,757,824 A | 7/1988 | Chaumet | |
| 4,757,825 A | 7/1988 | Diamond | |
| 4,765,340 A | 8/1988 | Sakai et al. | |
| 4,777,962 A | 10/1988 | Watson et al. | |
| 4,802,485 A | 2/1989 | Bowers et al. | |
| 4,802,486 A | 2/1989 | Goodman et al. | |
| 4,803,997 A | 2/1989 | Bowman | |
| 4,806,112 A | 2/1989 | Roberts et al. | |
| 4,807,616 A | 2/1989 | Adahan | |
| 4,815,473 A | 3/1989 | Watson et al. | |
| 4,838,279 A | 6/1989 | Fore | |
| 4,860,766 A | 8/1989 | Sackner | |
| 4,889,116 A | 12/1989 | Taube | |
| 4,895,162 A | 1/1990 | Dolliver | |
| 4,924,860 A | 5/1990 | Larsen et al. | |
| 4,928,692 A | 5/1990 | Goodman et al. | |
| 4,928,703 A | 5/1990 | Wong | |
| 4,941,469 A | 7/1990 | Adahan | |
| 4,958,638 A | 9/1990 | Sharpe et al. | |
| 4,961,423 A | 10/1990 | Canducci | |
| 4,982,738 A | 1/1991 | Griebel | |
| 5,005,234 A | 4/1991 | Kelleher et al. | |
| 5,005,571 A | 4/1991 | Dietz | |
| 5,016,636 A | 5/1991 | Kulakowski | |
| 5,036,852 A | 8/1991 | Leishman | |
| 5,052,400 A | 10/1991 | Dietz | |
| 5,095,900 A | 3/1992 | Fertig et al. | |
| 5,099,836 A | 3/1992 | Rowland et al. | |
| 5,105,354 A * | 4/1992 | Nishimura | A61B 5/0205 600/484 |
| 5,107,855 A | 4/1992 | Harrington et al. | |
| 5,131,387 A | 7/1992 | French et al. | |
| 5,131,399 A | 7/1992 | Sciarra | |
| 5,133,346 A | 7/1992 | Kulkarni | |
| 5,134,995 A | 8/1992 | Gruenke et al. | |
| 5,146,918 A | 9/1992 | Kallok et al. | |
| 5,174,287 A | 12/1992 | Kallok et al. | |
| 5,191,893 A | 3/1993 | Reiten | |
| 5,199,424 A | 4/1993 | Sullivan et al. | |
| 5,206,807 A | 4/1993 | Hatke et al. | |
| 5,211,173 A | 5/1993 | Kallok et al. | |
| 5,215,082 A | 6/1993 | Kallok et al. | |
| 5,233,983 A | 8/1993 | Markowitz | |
| 5,245,995 A | 9/1993 | Sullivan et al. | |
| 5,259,373 A | 11/1993 | Gruenke et al. | |
| 5,271,412 A | 12/1993 | Shtalryd et al. | |
| 5,275,159 A | 1/1994 | Griebel | |
| 5,277,194 A | 1/1994 | Hosterman et al. | |
| 5,278,190 A | 1/1994 | Askanazi et al. | |
| 5,294,642 A | 3/1994 | Askanazi et al. | |
| 5,295,490 A | 3/1994 | Dodakian | |
| 5,300,094 A | 4/1994 | Kallok et al. | |
| 5,307,817 A | 5/1994 | Guggenbuhl et al. | |
| 5,309,921 A | 5/1994 | Kisner et al. | |
| 5,311,875 A | 5/1994 | Stasz | |
| 5,348,008 A | 9/1994 | Bornn et al. | |
| 5,353,793 A | 10/1994 | Bornn | |
| 5,360,008 A | 11/1994 | Campbell, Jr. | |
| 5,373,859 A | 12/1994 | Forney | |
| 5,385,144 A | 1/1995 | Yamanishi et al. | |
| 5,395,301 A | 3/1995 | Russek | |
| 5,398,682 A | 3/1995 | Lynn | |
| 5,458,137 A | 10/1995 | Axe et al. | |
| 5,483,969 A | 1/1996 | Testerman et al. | |
| 5,485,850 A | 1/1996 | Dietz | |
| 5,485,851 A | 1/1996 | Erickson | |
| 5,492,113 A | 2/1996 | Estes et al. | |
| 5,495,242 A | 2/1996 | Kick et al. | |
| 5,513,631 A | 5/1996 | McWilliams | |
| 5,513,646 A | 5/1996 | Lehrman et al. | |
| 5,522,382 A | 6/1996 | Sullivan et al. | |
| 5,522,862 A | 6/1996 | Testerman et al. | |
| 5,535,738 A | 7/1996 | Estes et al. | |
| 5,537,997 A | 7/1996 | Mechlenburg et al. | |
| 5,540,219 A | 7/1996 | Mechlenburg et al. | |
| 5,540,731 A | 7/1996 | Testerman | |
| 5,540,732 A | 7/1996 | Testerman | |
| 5,540,733 A | 7/1996 | Testerman et al. | |
| 5,546,952 A | 8/1996 | Erickson | |
| 5,549,106 A | 8/1996 | Gruenke et al. | |
| 5,549,655 A | 8/1996 | Erickson | |
| 5,551,418 A | 9/1996 | Estes et al. | |
| 5,555,891 A | 9/1996 | Eisenfeld | |
| 5,564,429 A | 10/1996 | Bornn et al. | |
| 5,591,216 A | 1/1997 | Testerman et al. | |
| 5,603,316 A | 2/1997 | Coufal et al. | |
| 5,605,151 A | 2/1997 | Lynn | |
| 5,611,349 A | 3/1997 | Halleck et al. | |
| 5,632,269 A | 5/1997 | Zdrojkowski | |
| 5,645,053 A | 7/1997 | Remmers et al. | |
| 5,655,522 A | 8/1997 | Mechlenburg et al. | |
| 5,671,733 A | 9/1997 | Raviv et al. | |
| 5,704,345 A | 1/1998 | Berthon-Jones | |
| 5,765,554 A | 6/1998 | Somerson et al. | |
| 5,769,084 A | 6/1998 | Katz et al. | |
| 5,779,631 A | 7/1998 | Chance | |

(56) References Cited

U.S. PATENT DOCUMENTS

| | | | |
|---|---|---|---|
| 5,782,240 A | 7/1998 | Raviv et al. | |
| 5,792,068 A | 8/1998 | Bowman et al. | |
| 5,794,614 A | 8/1998 | Gruenke et al. | |
| 5,794,615 A | 8/1998 | Estes | |
| 5,800,360 A | 9/1998 | Kisner et al. | |
| 5,800,470 A | 9/1998 | Stein et al. | |
| 5,803,065 A | 9/1998 | Zdrojkowski et al. | |
| 5,803,066 A | 9/1998 | Rapoport et al. | |
| 5,823,187 A | 10/1998 | Estes et al. | |
| 5,825,293 A | 10/1998 | Ahmed et al. | |
| 5,845,636 A | 12/1998 | Gruenke et al. | |
| 5,853,005 A | 12/1998 | Scanlon | |
| 5,862,803 A | 1/1999 | Besson et al. | |
| 5,873,821 A | 2/1999 | Chance et al. | |
| 5,879,313 A | 3/1999 | Raviv et al. | |
| 5,891,023 A | 4/1999 | Lynn | |
| 5,895,360 A | 4/1999 | Christopherson et al. | |
| 5,901,704 A | 5/1999 | Estes et al. | |
| 5,902,250 A * | 5/1999 | Verrier | A61B 5/0205 600/515 |
| 5,904,141 A | 5/1999 | Estes et al. | |
| 5,913,826 A | 6/1999 | Blank | |
| 5,921,942 A | 7/1999 | Remmers et al. | |
| 5,928,157 A | 7/1999 | O'Dwyer | |
| 5,944,680 A | 8/1999 | Christopherson et al. | |
| 5,947,115 A | 9/1999 | Lordo et al. | |
| 5,953,713 A | 9/1999 | Behbehani et al. | |
| 5,954,050 A | 9/1999 | Christopher | |
| 5,954,053 A | 9/1999 | Chance et al. | |
| 5,957,854 A | 9/1999 | Besson et al. | |
| 5,961,447 A | 10/1999 | Raviv et al. | |
| 5,964,720 A | 10/1999 | Pelz | |
| 5,970,975 A | 10/1999 | Estes et al. | |
| 5,989,193 A | 11/1999 | Sullivan | |
| 6,015,388 A | 1/2000 | Sackner et al. | |
| 6,017,315 A | 1/2000 | Starr et al. | |
| 6,019,732 A | 2/2000 | Volgyesi | |
| 6,021,352 A | 2/2000 | Christopherson et al. | |
| 6,029,664 A | 2/2000 | Zdrojkowski et al. | |
| 6,029,665 A | 2/2000 | Berthon-Jones | |
| 6,032,072 A * | 2/2000 | Greenwald | A61B 5/291 600/397 |
| 6,045,514 A | 4/2000 | Raviv et al. | |
| 6,062,216 A | 5/2000 | Corn | |
| 6,064,910 A | 5/2000 | Andersson et al. | |
| 6,085,747 A | 7/2000 | Axe et al. | |
| 6,099,479 A | 8/2000 | Christopherson et al. | |
| 6,105,575 A | 8/2000 | Estes et al. | |
| 6,120,441 A | 9/2000 | Griebel | |
| 6,126,611 A | 10/2000 | Bourgeois et al. | |
| 6,132,384 A | 10/2000 | Christopherson et al. | |
| 6,134,460 A | 10/2000 | Chance | |
| 6,138,675 A | 10/2000 | Berthon-Jones | |
| 6,142,950 A | 11/2000 | Allen et al. | |
| 6,142,952 A | 11/2000 | Behbehani et al. | |
| 6,150,104 A | 11/2000 | Splawski et al. | |
| 6,150,941 A | 11/2000 | Geiger et al. | |
| 6,159,158 A | 12/2000 | Lowe | |
| 6,165,133 A | 12/2000 | Rapoport et al. | |
| 6,168,568 B1 | 1/2001 | Gavriely | |
| 6,190,328 B1 | 2/2001 | Ruton et al. | |
| 6,208,897 B1 | 3/2001 | Jorgenson et al. | |
| 6,223,064 B1 | 4/2001 | Lynn et al. | |
| 6,241,683 B1 | 6/2001 | Macklem et al. | |
| 6,248,068 B1 | 6/2001 | Seabron | |
| 6,251,126 B1 | 6/2001 | Ottenhoff et al. | |
| 6,261,238 B1 | 7/2001 | Gavriely | |
| 6,267,730 B1 | 7/2001 | Pacunas | |
| 6,269,269 B1 | 7/2001 | Ottenhoff et al. | |
| 6,273,859 B1 | 8/2001 | Remmers et al. | |
| 6,286,508 B1 | 9/2001 | Remmers et al. | |
| 6,289,238 B1 | 9/2001 | Besson et al. | |
| 6,290,654 B1 | 9/2001 | Karakasoglu | |
| 6,305,374 B1 | 10/2001 | Zdrojkowski et al. | |
| 6,306,088 B1 | 10/2001 | Krausman et al. | |
| 6,331,536 B1 | 12/2001 | Radulovacki et al. | |
| 6,342,039 B1 | 1/2002 | Lynn et al. | |
| 6,342,040 B1 | 1/2002 | Starr et al. | |
| 6,359,449 B1 | 3/2002 | Reining et al. | |
| 6,363,933 B1 | 4/2002 | Berthon-Jones | |
| 6,368,287 B1 | 4/2002 | Hadas | |
| 6,375,621 B1 | 4/2002 | Sullivan | |
| 6,390,987 B1 | 5/2002 | Graham | |
| 6,397,845 B1 | 6/2002 | Burton | |
| 6,398,739 B1 | 6/2002 | Sullivan et al. | |
| 6,409,676 B2 | 6/2002 | Ruton et al. | |
| 6,411,843 B1 * | 6/2002 | Zarychta | A61B 5/389 128/204.23 |
| 6,450,168 B1 | 9/2002 | Nguyen | |
| 6,450,957 B1 | 9/2002 | Yoshimi et al. | |
| 6,454,724 B1 | 9/2002 | Greene | |
| 6,470,888 B1 | 10/2002 | Matter | |
| 6,477,710 B1 | 11/2002 | Ojoyeyi | |
| 6,491,647 B1 | 12/2002 | Bridger et al. | |
| 6,498,652 B1 | 12/2002 | Varshneya et al. | |
| 6,510,339 B2 | 1/2003 | Kovtun et al. | |
| 6,517,497 B2 | 2/2003 | Rymut et al. | |
| 6,529,752 B2 | 3/2003 | Krausman et al. | |
| 6,537,228 B1 | 3/2003 | Lambert | |
| 6,539,940 B2 | 4/2003 | Zdrojkowski et al. | |
| 6,544,192 B2 | 4/2003 | Starr et al. | |
| 6,547,743 B2 | 4/2003 | Brydon | |
| 6,549,795 B1 | 4/2003 | Chance | |
| 6,550,478 B2 | 4/2003 | Remmers et al. | |
| 6,551,252 B2 | 4/2003 | Sackner et al. | |
| 6,553,242 B1 | 4/2003 | Sarussi | |
| 6,553,256 B1 | 4/2003 | Jorgenson et al. | |
| 6,555,564 B1 | 4/2003 | Radulovacki et al. | |
| 6,572,543 B1 | 6/2003 | Christopherson et al. | |
| 6,574,507 B1 | 6/2003 | Bonnet | |
| 6,577,893 B1 | 6/2003 | Besson et al. | |
| 6,580,943 B2 | 6/2003 | Nissila | |
| 6,580,944 B1 | 6/2003 | Katz et al. | |
| 6,595,215 B2 | 7/2003 | Wood | |
| 6,609,517 B1 | 8/2003 | Estes et al. | |
| 6,621,278 B2 | 9/2003 | Ariav | |
| 6,629,527 B1 | 10/2003 | Estes et al. | |
| 6,635,021 B1 | 10/2003 | Sullivan et al. | |
| 6,637,434 B2 | 10/2003 | Noble | |
| 6,675,797 B1 | 1/2004 | Berthon-Jones | |
| 6,705,315 B2 | 3/2004 | Sullivan et al. | |
| 6,721,980 B1 | 4/2004 | Price et al. | |
| 6,727,242 B2 | 4/2004 | Radulovacki et al. | |
| 6,739,335 B1 | 5/2004 | Rapport et al. | |
| 6,748,252 B2 | 6/2004 | Lynn et al. | |
| 6,760,608 B2 | 7/2004 | Lynn | |
| 6,770,037 B2 | 8/2004 | Sullivan et al. | |
| 6,773,404 B2 | 8/2004 | Poezevera et al. | |
| 6,776,162 B2 | 8/2004 | Wood | |
| 6,785,568 B2 | 8/2004 | Chance | |
| 6,807,967 B2 | 10/2004 | Wood | |
| 6,811,538 B2 | 11/2004 | Westbrook et al. | |
| 6,814,073 B2 | 11/2004 | Wickham | |
| 6,816,266 B2 | 11/2004 | Varshneya et al. | |
| 6,832,609 B2 | 12/2004 | Wright et al. | |
| 6,840,907 B1 | 1/2005 | Brydon | |
| 6,848,446 B2 | 2/2005 | Noble | |
| 6,849,049 B2 | 2/2005 | Starr et al. | |
| 6,856,141 B2 | 2/2005 | Ariav | |
| 6,881,192 B1 | 4/2005 | Park | |
| 6,889,691 B2 | 5/2005 | Eklund et al. | |
| 6,890,306 B2 | 5/2005 | Poezevera | |
| 6,904,320 B2 | 6/2005 | Park et al. | |
| 6,915,705 B1 | 7/2005 | Truitt et al. | |
| 6,918,878 B2 | 7/2005 | Brodnick | |
| 6,920,877 B2 | 7/2005 | Remmers et al. | |
| 6,928,324 B2 | 8/2005 | Park et al. | |
| 6,932,084 B2 | 8/2005 | Estes et al. | |
| 6,935,335 B1 | 8/2005 | Lehrman et al. | |
| 6,948,497 B2 | 9/2005 | Zdrojkowski et al. | |
| 6,964,641 B2 | 11/2005 | Cho et al. | |
| 6,970,737 B1 | 11/2005 | Brodnick et al. | |
| 6,974,814 B2 | 12/2005 | Radulovacki et al. | |
| 6,984,993 B2 | 1/2006 | Ariav | |

(56) References Cited

U.S. PATENT DOCUMENTS

| | | |
|---|---|---|
| 6,988,994 B2 | 1/2006 | Rapoport et al. |
| 6,989,744 B2 | 1/2006 | Proebsting |
| 6,997,177 B2 | 2/2006 | Wood |
| 6,999,817 B2 | 2/2006 | Park et al. |
| 7,004,908 B2 | 2/2006 | Sullivan et al. |
| 7,013,892 B2 | 3/2006 | Estes et al. |
| 7,013,893 B2 | 3/2006 | Wickham et al. |
| 7,018,341 B2 | 3/2006 | Wright et al. |
| 7,020,511 B2 | 3/2006 | Boyd et al. |
| 7,025,730 B2 | 4/2006 | Cho et al. |
| 7,035,432 B2 | 4/2006 | Szuba |
| 7,039,152 B2 | 5/2006 | Bruder et al. |
| 7,047,969 B2 | 5/2006 | Noble |
| 7,059,328 B2 | 6/2006 | Wood |
| 7,074,177 B2 | 7/2006 | Pickett et al. |
| 7,080,554 B2 | 7/2006 | Ariav et al. |
| 7,081,095 B2 | 7/2006 | Lynn et al. |
| 7,089,936 B2 | 8/2006 | Madaus et al. |
| 7,092,755 B2 | 8/2006 | Florio |
| 7,100,607 B2 | 9/2006 | Zdrojkowski et al. |
| 7,117,036 B2 | 10/2006 | Florio |
| 7,126,467 B2 | 10/2006 | Albert et al. |
| 7,128,717 B1 | 10/2006 | Thach et al. |
| 7,129,833 B2 | 10/2006 | Albert |
| 7,130,687 B2 | 10/2006 | Cho et al. |
| 7,141,021 B2 | 11/2006 | Sullivan et al. |
| 7,148,797 B2 | 12/2006 | Albert |
| 7,153,271 B2 | 12/2006 | Aylsworth |
| 7,159,588 B2 | 1/2007 | Wickham |
| 7,160,898 B2 | 1/2007 | Radulovacki et al. |
| 7,166,123 B2 | 1/2007 | Hovanes et al. |
| 7,168,429 B2 | 1/2007 | Matthews et al. |
| 7,170,404 B2 | 1/2007 | Albert et al. |
| 7,173,525 B2 | 2/2007 | Albert |
| 7,178,524 B2 | 2/2007 | Noble |
| 7,179,229 B1 | 2/2007 | Koh |
| 7,186,221 B2 | 3/2007 | Rapoport et al. |
| 7,188,624 B2 | 3/2007 | Wood |
| 7,190,995 B2 | 3/2007 | Chervin et al. |
| 7,212,862 B2 | 5/2007 | Park et al. |
| 7,215,991 B2 | 5/2007 | Besson et al. |
| 7,225,013 B2 | 5/2007 | Geva et al. |
| 7,225,021 B1 | 5/2007 | Park et al. |
| 7,269,459 B1 | 9/2007 | Koh |
| 7,296,573 B2 | 11/2007 | Estes et al. |
| 7,297,119 B2 | 11/2007 | Westbrook et al. |
| 7,306,564 B2 | 12/2007 | Nakatani et al. |
| 7,314,046 B2 | 1/2008 | Schroeder et al. |
| 7,314,451 B2 | 1/2008 | Halperin et al. |
| 7,315,759 B2 | 1/2008 | Markowitz et al. |
| 7,315,760 B2 | 1/2008 | Brodnick et al. |
| 7,320,320 B2 | 1/2008 | Berthon-Jones |
| 7,324,845 B2 | 1/2008 | Mietus et al. |
| 7,330,127 B2 | 2/2008 | Price et al. |
| 7,336,996 B2 | 2/2008 | Hartley et al. |
| 7,340,302 B1 | 3/2008 | Falkenberg et al. |
| 7,361,146 B1 | 4/2008 | Bharmi et al. |
| 7,363,086 B1 | 4/2008 | Koh et al. |
| 7,364,547 B2 | 4/2008 | Stahmann et al. |
| 7,371,220 B1 | 5/2008 | Koh et al. |
| 7,391,316 B2 | 6/2008 | Albert et al. |
| 7,396,333 B2 | 7/2008 | Stahmann et al. |
| 7,398,115 B2 | 7/2008 | Lynn |
| 7,403,110 B2 | 7/2008 | Albert et al. |
| 7,415,093 B2 | 8/2008 | Tkaczyk et al. |
| 7,431,700 B2 | 10/2008 | Aoki et al. |
| 7,435,221 B1 | 10/2008 | Bharmi et al. |
| 7,438,686 B2 | 10/2008 | Cho et al. |
| 7,440,795 B2 | 10/2008 | Poezevara |
| 7,460,899 B2 | 12/2008 | Almen |
| 7,467,012 B1 | 12/2008 | Park et al. |
| 7,468,040 B2 | 12/2008 | Hartley et al. |
| 7,469,697 B2 | 12/2008 | Lee et al. |
| 7,473,227 B2 | 1/2009 | Hsu et al. |
| 7,477,142 B2 | 1/2009 | Albert et al. |
| 7,477,143 B2 | 1/2009 | Albert |
| 7,477,144 B2 | 1/2009 | Albert |
| 7,479,114 B2 | 1/2009 | Hartley et al. |
| 7,508,307 B2 | 3/2009 | Albert |
| 7,509,164 B2 | 3/2009 | Jensen et al. |
| 7,510,531 B2 | 3/2009 | Lee et al. |
| 7,515,059 B2 | 4/2009 | Price et al. |
| 7,519,425 B2 | 4/2009 | Benser et al. |
| 7,520,279 B2 | 4/2009 | Berthon-Jones |
| 7,522,035 B2 | 4/2009 | Albert |
| 7,532,934 B2 | 5/2009 | Lee et al. |
| 7,533,571 B2 | 5/2009 | Ariav et al. |
| 7,545,279 B2 | 6/2009 | Sato et al. |
| 7,572,225 B2 | 8/2009 | Stahmann et al. |
| 7,591,265 B2 | 9/2009 | Lee et al. |
| 7,593,764 B2 | 9/2009 | Kohls et al. |
| 7,593,767 B1 | 9/2009 | Modarres |
| 7,596,413 B2 | 9/2009 | Libbus et al. |
| 7,597,659 B2 | 10/2009 | Pickett et al. |
| 7,611,472 B2 | 11/2009 | Lu |
| 7,623,912 B2 | 11/2009 | Akselrod et al. |
| 7,636,600 B1 | 12/2009 | Koh |
| 7,650,189 B1 | 1/2010 | Park et al. |
| 7,656,287 B2 | 2/2010 | Albert et al. |
| 7,661,426 B2 | 2/2010 | Lauk et al. |
| 7,662,101 B2 | 2/2010 | Lee et al. |
| 7,667,624 B2 | 2/2010 | Stoval |
| 7,668,579 B2 | 2/2010 | Lynn |
| 7,668,591 B2 | 2/2010 | Lee et al. |
| 7,670,295 B2 | 3/2010 | Sackner et al. |
| 7,674,230 B2 | 3/2010 | Reisfeld |
| 7,678,058 B2 | 3/2010 | Patangay et al. |
| 7,678,061 B2 | 3/2010 | Lee et al. |
| 7,680,537 B2 | 3/2010 | Stahmann et al. |
| 7,691,067 B2 | 4/2010 | Westbrook et al. |
| 7,697,990 B2 | 4/2010 | Ujhazy et al. |
| 7,705,039 B2 | 4/2010 | Carley et al. |
| 7,706,852 B2 | 4/2010 | Baker, Jr. |
| 7,708,697 B2 | 5/2010 | Wilkinson et al. |
| 7,711,579 B2 | 5/2010 | Lancaster et al. |
| 7,715,905 B2 | 5/2010 | Kurzweil et al. |
| 7,716,767 B2 | 5/2010 | Bohm et al. |
| 7,720,541 B2 | 5/2010 | Stahmann et al. |
| 7,725,181 B1 | 5/2010 | Bornzin et al. |
| 7,730,886 B2 | 6/2010 | Berthon-Jones |
| 7,734,334 B2 | 6/2010 | Mietus et al. |
| 7,734,335 B2 | 6/2010 | Kontothanassis et al. |
| 7,734,340 B2 | 6/2010 | De Ridder |
| 7,734,350 B2 | 6/2010 | Dubnov et al. |
| 7,735,491 B2 | 6/2010 | Doshi et al. |
| 7,735,492 B2 | 6/2010 | Doshi et al. |
| 7,740,591 B1 | 6/2010 | Starr et al. |
| 7,747,323 B2 | 6/2010 | Libbus et al. |
| 7,748,493 B2 | 7/2010 | Moses et al. |
| 7,757,690 B2 | 7/2010 | Stahmann et al. |
| 7,758,503 B2 | 7/2010 | Lynn et al. |
| 7,766,840 B2 | 8/2010 | Kwok et al. |
| 7,766,841 B2 | 8/2010 | Yamamoto et al. |
| 7,770,578 B2 | 8/2010 | Estes et al. |
| 7,787,946 B2 | 8/2010 | Stahmann et al. |
| 7,788,343 B2 | 8/2010 | Haselhurst et al. |
| 7,789,837 B2 | 9/2010 | Lehrman et al. |
| 7,794,406 B2 | 9/2010 | Reisfeld et al. |
| 7,794,716 B2 | 9/2010 | Adair |
| 7,798,148 B2 | 9/2010 | Doshi et al. |
| 7,800,505 B2 | 9/2010 | Pietersen |
| 7,803,118 B2 | 9/2010 | Reisfeld et al. |
| 7,803,119 B2 | 9/2010 | Reisfeld |
| 7,806,120 B2 | 10/2010 | Loomas et al. |
| 7,810,496 B2 | 10/2010 | Estes et al. |
| 7,810,497 B2 | 10/2010 | Pittman et al. |
| 7,811,234 B2 | 10/2010 | McGrath |
| 7,818,058 B2 | 10/2010 | Mentelos |
| 7,819,816 B2 | 10/2010 | Pu et al. |
| 7,827,988 B2 | 11/2010 | Matthews et al. |
| 7,828,739 B2 | 11/2010 | Arnold |
| 7,848,792 B2 | 12/2010 | Vitali et al. |
| 7,856,979 B2 | 12/2010 | Doshi et al. |
| 7,884,735 B2 | 2/2011 | Newkirk |

(56) References Cited

U.S. PATENT DOCUMENTS

| | | |
|---|---|---|
| 7,887,493 B2 | 2/2011 | Stahmann et al. |
| 7,894,849 B2 | 2/2011 | Kass et al. |
| 7,896,812 B2 | 3/2011 | Rapoport et al. |
| 7,899,519 B2 | 3/2011 | Carlson et al. |
| 7,899,521 B2 | 3/2011 | Demharter et al. |
| 7,900,626 B2 | 3/2011 | Daly |
| 7,909,764 B1 | 3/2011 | Wenzel et al. |
| 7,934,500 B2 | 5/2011 | Madaus et al. |
| 7,938,114 B2 | 5/2011 | Matthews et al. |
| 7,938,782 B2 | 5/2011 | Stahmann et al. |
| 7,942,822 B1 | 5/2011 | Koh |
| 7,942,823 B2 | 5/2011 | Wright et al. |
| 7,942,824 B1 | 5/2011 | Kayyali et al. |
| 7,970,470 B2 | 6/2011 | Hartley et al. |
| 7,976,470 B2 | 7/2011 | Patangay et al. |
| 7,981,042 B2 | 7/2011 | Stahmann et al. |
| 7,988,640 B2 | 8/2011 | Berthon-Jones et al. |
| 7,993,279 B2 | 8/2011 | Hartley et al. |
| 7,994,218 B2 | 8/2011 | Jandeleit et al. |
| 8,002,553 B2 | 8/2011 | Hatlestad et al. |
| 8,011,365 B2 | 9/2011 | Douglas et al. |
| 8,021,309 B2 | 9/2011 | Zilberg |
| 8,031,080 B2 | 10/2011 | Price et al. |
| 8,043,225 B2 | 10/2011 | Poezevara |
| 8,050,765 B2 | 11/2011 | Lee et al. |
| 8,053,413 B2 | 11/2011 | Carley et al. |
| 8,069,852 B2 | 12/2011 | Burton et al. |
| 8,074,646 B2 | 12/2011 | Daly |
| 8,076,315 B2 | 12/2011 | Carley et al. |
| 8,104,470 B2 | 1/2012 | Lee et al. |
| 8,106,781 B2 | 1/2012 | Pietersen |
| 8,119,134 B2 | 2/2012 | Adair |
| 8,121,692 B2 | 2/2012 | Haefner et al. |
| 8,136,521 B2 | 3/2012 | Matthews et al. |
| 8,140,164 B2 | 3/2012 | Tehrani et al. |
| 8,142,343 B2 | 3/2012 | Pickett et al. |
| 8,152,732 B2 | 4/2012 | Lynn et al. |
| 8,155,735 B2 | 4/2012 | Bashour et al. |
| 8,161,971 B2 | 4/2012 | Jaffe et al. |
| 8,167,812 B2 | 5/2012 | Scholler et al. |
| 8,168,617 B2 | 5/2012 | Jandeleit et al. |
| 8,187,200 B2 | 5/2012 | Jensen et al. |
| 8,187,201 B2 | 5/2012 | Lynn |
| 8,192,376 B2 | 6/2012 | Lovett et al. |
| 8,200,336 B2 | 6/2012 | Tehrani et al. |
| 8,203,330 B2 | 6/2012 | Ansay et al. |
| 8,204,580 B2 | 6/2012 | Kurzweil et al. |
| 8,207,230 B2 | 6/2012 | Carley et al. |
| 8,219,185 B2 | 7/2012 | Lin et al. |
| 8,221,327 B2 | 7/2012 | Lee et al. |
| 8,225,789 B2 | 7/2012 | Berthon-Jones |
| 8,226,569 B2 | 7/2012 | Sotos et al. |
| 8,226,570 B2 | 7/2012 | Pu et al. |
| 8,226,571 B2 | 7/2012 | Landesberg et al. |
| 8,233,987 B2 | 7/2012 | Gelfand et al. |
| 8,238,996 B2 | 8/2012 | Burnes et al. |
| 8,241,213 B2 | 8/2012 | Lynn et al. |
| 8,251,061 B2 | 8/2012 | Lee et al. |
| 8,255,029 B2 | 8/2012 | Addison et al. |
| 8,255,056 B2 | 8/2012 | Tehrani |
| 8,258,973 B2 | 9/2012 | Newkirk |
| 8,261,742 B2 | 9/2012 | Strothmann et al. |
| 8,262,578 B1 | 9/2012 | Bharmi et al. |
| 8,265,759 B2 | 9/2012 | Tehrani et al. |
| 8,273,053 B2 | 9/2012 | Saltzstein |
| 8,275,553 B2 | 9/2012 | Ochs et al. |
| 8,280,513 B2 | 10/2012 | Tehrani et al. |
| 8,301,219 B2 | 10/2012 | Chen et al. |
| 8,301,232 B2 | 10/2012 | Albert et al. |
| 8,321,022 B2 | 11/2012 | Stahmann et al. |
| 8,323,204 B2 | 12/2012 | Stahmann et al. |
| 8,333,708 B2 | 12/2012 | Rapoport et al. |
| 8,343,057 B2 | 1/2013 | Starr et al. |
| 8,348,840 B2 | 1/2013 | Heit et al. |
| 8,348,941 B2 | 1/2013 | Tehrani |
| 8,356,594 B2 | 1/2013 | Ujhazy et al. |
| 8,360,060 B2 | 1/2013 | Berthon-Jones |
| 8,360,983 B2 | 1/2013 | Patangay et al. |
| 8,365,729 B2 | 2/2013 | Alder et al. |
| 8,365,730 B2 | 2/2013 | Baker, Jr. et al. |
| 8,380,296 B2 | 2/2013 | Lee et al. |
| 8,381,722 B2 | 2/2013 | Berthon-Jones |
| 8,393,233 B2 | 3/2013 | Lu |
| 8,396,537 B2 | 3/2013 | Balji et al. |
| 8,398,555 B2 | 3/2013 | Ochs et al. |
| 8,401,626 B2 | 3/2013 | Mietus et al. |
| 8,401,655 B2 | 3/2013 | De Ridder |
| 8,403,848 B2 | 3/2013 | Mietus et al. |
| 8,403,861 B2 | 3/2013 | Williams et al. |
| 8,403,865 B2 | 3/2013 | Halperin et al. |
| 8,408,205 B2 | 4/2013 | Madaus et al. |
| 8,417,351 B2 | 4/2013 | Kilger |
| 8,442,578 B2 | 5/2013 | Kass et al. |
| 8,442,638 B2 | 5/2013 | Libbus et al. |
| 8,449,473 B2 | 5/2013 | Varney et al. |
| 8,454,528 B2 | 6/2013 | Yuen et al. |
| 8,460,159 B2 | 6/2013 | Mikhailenok et al. |
| 8,467,876 B2 | 6/2013 | Tehrani |
| 8,482,418 B1 | 7/2013 | Harman |
| 8,483,807 B2 | 7/2013 | Kurzweil et al. |
| 8,483,811 B2 | 7/2013 | Ueda |
| 8,483,834 B2 | 7/2013 | Lee et al. |
| 8,485,181 B2 | 7/2013 | Daly |
| 8,489,182 B2 | 7/2013 | Duckert et al. |
| 8,491,490 B2 | 7/2013 | Ozaki et al. |
| 8,509,882 B2 | 8/2013 | Albert et al. |
| 8,509,901 B2 | 8/2013 | Tehrani |
| 8,515,529 B2 | 8/2013 | Pu et al. |
| 8,522,779 B2 | 9/2013 | Lee et al. |
| 8,527,028 B2 | 9/2013 | Kurzweil et al. |
| 8,532,737 B2 | 9/2013 | Cervantes |
| 8,538,510 B2 | 9/2013 | Toledo et al. |
| 8,545,416 B1 | 10/2013 | Kayyali et al. |
| 8,551,010 B2 | 10/2013 | Pu et al. |
| 8,554,323 B2 | 10/2013 | Haefner et al. |
| 8,560,044 B2 | 10/2013 | Kurzweil et al. |
| 8,562,526 B2 | 10/2013 | Heneghan et al. |
| 8,565,846 B2 | 10/2013 | Ono et al. |
| 8,566,115 B2 | 10/2013 | Moore |
| 8,568,160 B2 | 10/2013 | Coggins et al. |
| 8,569,374 B2 | 10/2013 | Veasey |
| 8,579,792 B2 | 11/2013 | Pickett et al. |
| 8,595,164 B2 | 11/2013 | Dong et al. |
| 8,600,502 B2 | 12/2013 | Lovett et al. |
| 8,603,010 B2 | 12/2013 | Lange et al. |
| 8,604,066 B2 | 12/2013 | Baud et al. |
| 8,606,356 B2 | 12/2013 | Lee et al. |
| 8,607,793 B2 | 12/2013 | Armitstead et al. |
| 8,616,203 B2 | 12/2013 | Jaffe et al. |
| 8,620,448 B1 | 12/2013 | Delia |
| 8,630,704 B2 | 1/2014 | Pu et al. |
| 8,630,712 B2 | 1/2014 | Moses et al. |
| 8,641,631 B2 | 2/2014 | Sierra et al. |
| 8,644,921 B2 | 2/2014 | Wilson |
| 8,646,447 B2 | 2/2014 | Martin et al. |
| 8,657,756 B2 | 2/2014 | Stahmann et al. |
| 8,666,467 B2 | 3/2014 | Lynn et al. |
| 8,679,034 B2 | 3/2014 | Halperin et al. |
| 8,683,999 B2 | 4/2014 | Douglas et al. |
| 8,684,000 B2 | 4/2014 | Berthon-Jones et al. |
| 8,688,219 B2 | 4/2014 | Ransom |
| 8,696,589 B2 | 4/2014 | Kwok et al. |
| 8,700,137 B2 | 4/2014 | Albert |
| 8,707,953 B2 | 4/2014 | Wickham |
| 8,708,920 B2 | 4/2014 | Delos et al. |
| 8,718,751 B2 | 5/2014 | Hastings et al. |
| 8,721,554 B2 | 5/2014 | Lin et al. |
| 8,721,555 B2 | 5/2014 | Westbrook et al. |
| 8,721,560 B2 | 5/2014 | Koh |
| 8,721,573 B2 | 5/2014 | Hoffmann |
| 8,728,001 B2 | 5/2014 | Lynn |
| 8,731,644 B2 | 5/2014 | Mehrotra et al. |
| 8,731,646 B2 | 5/2014 | Halperin et al. |
| 8,739,789 B2 | 6/2014 | Wickham |

(56) References Cited

U.S. PATENT DOCUMENTS

| | | |
|---|---|---|
| 8,740,806 B2 | 6/2014 | Parfenova et al. |
| 8,740,808 B2 | 6/2014 | Curti et al. |
| 8,750,987 B2 | 6/2014 | Pu et al. |
| 8,752,547 B2 | 6/2014 | Berthon-Jones |
| 8,755,854 B2 | 6/2014 | Addison et al. |
| 8,758,243 B2 | 6/2014 | Wang et al. |
| 8,764,667 B2 | 7/2014 | Avidor et al. |
| 8,768,731 B2 | 7/2014 | Moore |
| 8,771,184 B2 | 7/2014 | Besson et al. |
| 8,781,753 B2 | 7/2014 | Ochs et al. |
| 8,790,270 B2 | 7/2014 | Landesberg et al. |
| 8,794,235 B2 | 8/2014 | Garde et al. |
| 8,794,236 B2 | 8/2014 | Phuah et al. |
| 8,801,620 B2 | 8/2014 | Melker et al. |
| 8,828,386 B2 | 9/2014 | Adair |
| 8,844,525 B2 | 9/2014 | Schindhelm et al. |
| 8,862,196 B2 | 10/2014 | Lynn |
| 8,862,211 B2 | 10/2014 | Toledo et al. |
| 8,868,152 B2 | 10/2014 | Burnes et al. |
| 8,880,207 B2 | 11/2014 | Abeyratne et al. |
| 8,892,194 B2 | 11/2014 | Balji et al. |
| 8,897,870 B2 | 11/2014 | De Ridder |
| 8,905,928 B2 | 12/2014 | Hayes et al. |
| 8,915,741 B2 | 12/2014 | Hatlestad et al. |
| 8,923,971 B2 | 12/2014 | Haefner et al. |
| 8,932,227 B2 | 1/2015 | Lynn |
| 8,938,299 B2 | 1/2015 | Christopherson et al. |
| 8,948,854 B2 | 2/2015 | Friedman et al. |
| 8,954,137 B2 | 2/2015 | Kurzweil et al. |
| 8,971,936 B2 | 3/2015 | Derchak |
| 8,983,587 B2 | 3/2015 | Kurzweil et al. |
| 8,983,611 B2 | 3/2015 | Mokelke et al. |
| 8,985,106 B2 | 3/2015 | Armitstead |
| 8,992,434 B2 | 3/2015 | Halperin et al. |
| 8,992,436 B2 | 3/2015 | Pu et al. |
| 8,999,658 B2 | 4/2015 | Gozal et al. |
| 9,011,341 B2 | 4/2015 | Jensen et al. |
| 9,011,347 B2 | 4/2015 | Addison et al. |
| 9,014,819 B2 | 4/2015 | Lee et al. |
| 9,019,100 B2 | 4/2015 | Sholder |
| 9,022,032 B2 | 5/2015 | Holzrichter |
| 9,024,781 B2 | 5/2015 | Zhang et al. |
| 9,026,202 B2 | 5/2015 | Albert |
| 9,031,793 B2 | 5/2015 | Lynn et al. |
| 9,037,477 B2 | 5/2015 | Bardy et al. |
| 9,042,952 B2 | 5/2015 | Lynn et al. |
| 9,044,362 B2 | 6/2015 | Gozelski, Jr. et al. |
| 9,044,558 B2 | 6/2015 | Baker, Jr. et al. |
| 9,044,565 B2 | 6/2015 | Colman et al. |
| 9,050,024 B2 | 6/2015 | Ujhazy et al. |
| 9,053,222 B2 | 6/2015 | Lynn et al. |
| 9,078,577 B2 | 7/2015 | He et al. |
| 9,084,859 B2 | 7/2015 | Connor |
| 9,089,691 B2 | 7/2015 | Libbus et al. |
| 9,095,307 B2 | 8/2015 | Parfenova et al. |
| 9,095,471 B2 | 8/2015 | Iyer et al. |
| 9,101,277 B2 | 8/2015 | Doerr |
| 9,108,009 B2 | 8/2015 | Rapoport et al. |
| 9,113,788 B2 | 8/2015 | Balji et al. |
| 9,131,892 B2 | 9/2015 | Markel |
| 9,131,902 B2 | 9/2015 | Halperin et al. |
| 9,132,250 B2 | 9/2015 | Allum et al. |
| 9,138,553 B2 | 9/2015 | Wood |
| 9,144,389 B2 | 9/2015 | Srinivasan et al. |
| 9,155,493 B2 | 10/2015 | Addison et al. |
| 9,168,344 B2 | 10/2015 | Rapoport et al. |
| 9,177,459 B2 | 11/2015 | Sholder |
| 9,180,270 B2 | 11/2015 | Kapust et al. |
| 9,192,336 B2 | 11/2015 | Addison et al. |
| 9,198,616 B2 | 12/2015 | Addison et al. |
| 9,198,617 B2 | 12/2015 | Kurzweil et al. |
| 9,199,053 B1 | 12/2015 | Allum et al. |
| 9,202,084 B2 | 12/2015 | Moore |
| 9,215,075 B1 | 12/2015 | Poltorak |
| 9,216,291 B2 | 12/2015 | Lee et al. |
| 9,220,459 B2 | 12/2015 | Addison et al. |
| 9,220,460 B2 | 12/2015 | Addison et al. |
| 9,220,856 B2 | 12/2015 | Martin et al. |
| 9,227,034 B2 | 1/2016 | Kapust et al. |
| 9,238,113 B2 | 1/2016 | Loomas et al. |
| 9,247,885 B2 | 2/2016 | Kirchner et al. |
| 9,259,544 B2 | 2/2016 | Kane et al. |
| 9,259,573 B2 | 2/2016 | Tehrani et al. |
| 9,269,000 B2 | 2/2016 | Korhonen et al. |
| 9,277,867 B2 | 3/2016 | Kurzweil et al. |
| 9,283,341 B2 | 3/2016 | Ujhazy et al. |
| 9,284,333 B2 | 3/2016 | Bialy et al. |
| 9,295,797 B2 | 3/2016 | Shissler et al. |
| 9,302,066 B2 | 4/2016 | Bertinetti et al. |
| 9,302,116 B2 | 4/2016 | Vo-Dinh et al. |
| 9,307,921 B2 | 4/2016 | Friedman et al. |
| 9,314,168 B2 | 4/2016 | Watson et al. |
| 9,333,318 B2 | 5/2016 | Cragg et al. |
| 9,364,180 B2 | 6/2016 | Armitstead |
| 9,370,634 B2 | 6/2016 | Melker et al. |
| 9,386,952 B2 | 7/2016 | Younes |
| 9,392,950 B2 | 7/2016 | Milpied |
| 9,402,563 B2 | 8/2016 | Thakur et al. |
| 9,414,787 B2 | 8/2016 | Montambeau et al. |
| 9,415,182 B2 | 8/2016 | Schneider et al. |
| 9,427,539 B2 | 8/2016 | Rapoport et al. |
| 9,433,356 B2 | 9/2016 | Olde et al. |
| 9,435,814 B2 | 9/2016 | Gozal et al. |
| 9,445,736 B2 | 9/2016 | Kurzweil et al. |
| 9,445,740 B1 | 9/2016 | Crone et al. |
| 9,445,747 B2 | 9/2016 | Rahamim et al. |
| 9,449,493 B2 | 9/2016 | Shinar et al. |
| 9,451,888 B1 | 9/2016 | Bernstein |
| 9,462,975 B2 | 10/2016 | Sackner et al. |
| 9,468,378 B2 | 10/2016 | Lynn et al. |
| 9,468,835 B2 | 10/2016 | Martikka et al. |
| 9,477,812 B2 | 10/2016 | Lin et al. |
| 9,492,106 B2 | 11/2016 | Haveri |
| 9,521,971 B2 | 12/2016 | Lynn et al. |
| 9,526,429 B2 | 12/2016 | Heneghan et al. |
| 9,533,114 B1 | 1/2017 | Kayyali et al. |
| 9,533,115 B2 | 1/2017 | Rapoport et al. |
| 9,538,954 B2 | 1/2017 | Patangay et al. |
| 9,586,048 B2 | 3/2017 | Ternes et al. |
| 9,629,970 B2 | 4/2017 | Matthews et al. |
| 9,669,172 B2 | 6/2017 | Cullen et al. |
| 9,675,264 B2 | 6/2017 | Acquista et al. |
| 9,682,208 B2 | 6/2017 | Ramanan et al. |
| 9,687,177 B2 | 6/2017 | Ramanan et al. |
| 9,706,934 B2 | 7/2017 | Wilson |
| 9,724,020 B2 | 8/2017 | Bowman et al. |
| 9,726,390 B2 | 8/2017 | Miller |
| 9,730,632 B1 | 8/2017 | Kayyali et al. |
| 9,737,258 B2 | 8/2017 | Poon et al. |
| 9,743,841 B2 | 8/2017 | Pittman et al. |
| 9,750,429 B1 | 9/2017 | Sackner et al. |
| 9,764,135 B2 | 9/2017 | De Ridder |
| 9,782,133 B2 | 10/2017 | Wickham |
| 9,788,782 B2 | 10/2017 | Thakur et al. |
| 9,814,429 B2 | 11/2017 | Lee et al. |
| 9,826,903 B2 | 11/2017 | Derchak |
| 9,833,354 B2 | 12/2017 | Loomas et al. |
| 9,839,756 B2 | 12/2017 | Klasek |
| 9,848,820 B2 | 12/2017 | Chen et al. |
| 9,848,831 B2 | 12/2017 | Nonaka et al. |
| 9,867,955 B2 | 1/2018 | Rapoport et al. |
| 9,872,987 B2 | 1/2018 | Libbus et al. |
| 9,878,114 B2 | 1/2018 | Daly |
| 9,884,159 B2 | 2/2018 | Daly |
| 9,884,860 B2 | 2/2018 | Bialy et al. |
| 9,889,267 B2 | 2/2018 | Wells et al. |
| 9,919,121 B2 | 3/2018 | Wood |
| 9,925,086 B2 | 3/2018 | Sanders et al. |
| 9,931,074 B2 | 4/2018 | Ni et al. |
| 9,931,483 B2 | 4/2018 | Knepper et al. |
| 9,932,565 B2 | 4/2018 | Vitalis et al. |
| 9,950,112 B2 | 4/2018 | Melker et al. |
| 9,980,664 B2 | 5/2018 | Fernando et al. |
| 9,987,488 B1 | 6/2018 | Gelfand et al. |

(56) References Cited

U.S. PATENT DOCUMENTS

| | | |
|---|---|---|
| 9,999,768 B2 | 6/2018 | Gelfand et al. |
| 2001/0018557 A1 | 8/2001 | Lynn et al. |
| 2001/0044588 A1 | 11/2001 | Mault |
| 2002/0007126 A1 | 1/2002 | Nissila |
| 2002/0007127 A1 | 1/2002 | Sullivan et al. |
| 2002/0023645 A1 | 2/2002 | Zdrojkowski et al. |
| 2002/0032386 A1 | 3/2002 | Sackner et al. |
| 2002/0043264 A1 | 4/2002 | Wickham |
| 2002/0049479 A1 | 4/2002 | Pitts |
| 2002/0059935 A1 | 5/2002 | Wood |
| 2002/0072685 A1 | 6/2002 | Rymut et al. |
| 2002/0078957 A1 | 6/2002 | Remmers et al. |
| 2002/0086870 A1 | 7/2002 | Radulovacki et al. |
| 2002/0092527 A1 | 7/2002 | Wood |
| 2002/0095076 A1 | 7/2002 | Krausman et al. |
| 2002/0099300 A1 | 7/2002 | Kovtun et al. |
| 2002/0100477 A1 | 8/2002 | Sullivan et al. |
| 2002/0105340 A1 | 8/2002 | Ariav |
| 2002/0124848 A1 | 9/2002 | Sullivan et al. |
| 2002/0161290 A1 | 10/2002 | Chance |
| 2002/0162558 A1 | 11/2002 | Noble |
| 2002/0165462 A1 | 11/2002 | Westbrook et al. |
| 2002/0173707 A1 | 11/2002 | Lynn et al. |
| 2002/0185130 A1 | 12/2002 | Wright et al. |
| 2002/0185131 A1 | 12/2002 | Madaus et al. |
| 2003/0000522 A1 | 1/2003 | Lynn et al. |
| 2003/0023175 A1* | 1/2003 | Arzbaecher ............ A61B 5/0006 600/509 |
| 2003/0024528 A1 | 2/2003 | Graham |
| 2003/0045806 A1 | 3/2003 | Brydon |
| 2003/0095263 A1 | 5/2003 | Varshneya et al. |
| 2003/0111079 A1 | 6/2003 | Matthews et al. |
| 2003/0121519 A1 | 7/2003 | Estes et al. |
| 2003/0130266 A1 | 7/2003 | Radulovacki et al. |
| 2003/0130589 A1 | 7/2003 | Poezevera |
| 2003/0135127 A1 | 7/2003 | Sackner et al. |
| 2003/0145856 A1 | 8/2003 | Zdrojkowski et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0158466 A1 | 8/2003 | Lynn et al. |
| 2003/0161436 A1 | 8/2003 | Boyd et al. |
| 2003/0161440 A1 | 8/2003 | Boyd et al. |
| 2003/0163059 A1 | 8/2003 | Poezevera et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0208130 A1 | 11/2003 | Yotam et al. |
| 2003/0208465 A1 | 11/2003 | Yurko et al. |
| 2003/0209246 A1 | 11/2003 | Schroeder et al. |
| 2003/0213488 A1 | 11/2003 | Remmers et al. |
| 2003/0221689 A1 | 12/2003 | Berthon-Jones |
| 2003/0236228 A1 | 12/2003 | Radulovacki et al. |
| 2003/0236548 A1 | 12/2003 | Hovanes et al. |
| 2004/0002742 A1 | 1/2004 | Florio |
| 2004/0015058 A1 | 1/2004 | Besson et al. |
| 2004/0016433 A1 | 1/2004 | Estes et al. |
| 2004/0020493 A1 | 2/2004 | Wood |
| 2004/0082874 A1 | 4/2004 | Aoki et al. |
| 2004/0103899 A1 | 6/2004 | Noble |
| 2004/0104733 A1 | 6/2004 | Ariav |
| 2004/0123866 A1 | 7/2004 | Berthon-Jones |
| 2004/0127572 A1 | 7/2004 | Carley et al. |
| 2004/0138576 A1 | 7/2004 | Wright et al. |
| 2004/0138719 A1 | 7/2004 | Cho et al. |
| 2004/0158193 A1 | 8/2004 | Bui et al. |
| 2004/0162499 A1 | 8/2004 | Nagai et al. |
| 2004/0176695 A1 | 9/2004 | Poezevara |
| 2004/0186523 A1 | 9/2004 | Florio |
| 2004/0187870 A1 | 9/2004 | Matthews et al. |
| 2004/0194220 A1 | 10/2004 | Price et al. |
| 2004/0207409 A1 | 10/2004 | Ariav et al. |
| 2004/0230105 A1 | 11/2004 | Geva et al. |
| 2004/0254481 A1 | 12/2004 | Brodnick |
| 2004/0254493 A1 | 12/2004 | Chervin et al. |
| 2004/0257233 A1 | 12/2004 | Proebsting |
| 2005/0027204 A1 | 2/2005 | Kligfield et al. |
| 2005/0027206 A1 | 2/2005 | Ariav |
| 2005/0027207 A1 | 2/2005 | Westbrook et al. |
| 2005/0034730 A1 | 2/2005 | Wood |
| 2005/0038353 A1 | 2/2005 | Rapoport et al. |
| 2005/0039745 A1 | 2/2005 | Stahmann et al. |
| 2005/0039750 A1 | 2/2005 | Wickham et al. |
| 2005/0039757 A1 | 2/2005 | Wood |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0053262 A1 | 3/2005 | Szuba |
| 2005/0055060 A1 | 3/2005 | Koh et al. |
| 2005/0061315 A1 | 3/2005 | Lee et al. |
| 2005/0061319 A1 | 3/2005 | Hartley et al. |
| 2005/0061320 A1 | 3/2005 | Lee et al. |
| 2005/0061323 A1 | 3/2005 | Lee et al. |
| 2005/0065447 A1 | 3/2005 | Lee et al. |
| 2005/0065560 A1 | 3/2005 | Lee et al. |
| 2005/0065566 A1 | 3/2005 | Hartley et al. |
| 2005/0065567 A1 | 3/2005 | Lee et al. |
| 2005/0065572 A1 | 3/2005 | Hartley et al. |
| 2005/0074741 A1 | 4/2005 | Lee et al. |
| 2005/0076905 A1 | 4/2005 | Stahmann et al. |
| 2005/0076908 A1 | 4/2005 | Lee et al. |
| 2005/0080348 A1 | 4/2005 | Stahmann et al. |
| 2005/0080461 A1 | 4/2005 | Stahmann et al. |
| 2005/0081847 A1 | 4/2005 | Lee et al. |
| 2005/0085736 A1 | 4/2005 | Ambrose et al. |
| 2005/0085738 A1 | 4/2005 | Stahmann et al. |
| 2005/0085863 A1 | 4/2005 | Brodnick et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0090871 A1 | 4/2005 | Cho et al. |
| 2005/0096559 A1 | 5/2005 | Yanai |
| 2005/0101833 A1 | 5/2005 | Hsu et al. |
| 2005/0103346 A1 | 5/2005 | Noble |
| 2005/0107838 A1 | 5/2005 | Lovett et al. |
| 2005/0113656 A1 | 5/2005 | Chance |
| 2005/0113710 A1 | 5/2005 | Stahmann et al. |
| 2005/0113711 A1 | 5/2005 | Nakatani et al. |
| 2005/0115561 A1 | 6/2005 | Stahmann et al. |
| 2005/0119711 A1 | 6/2005 | Cho et al. |
| 2005/0126574 A1 | 6/2005 | Wood |
| 2005/0148897 A1 | 7/2005 | Cho et al. |
| 2005/0165457 A1 | 7/2005 | Benser et al. |
| 2005/0177051 A1 | 8/2005 | Almen |
| 2005/0197588 A1 | 9/2005 | Freeberg |
| 2005/0211248 A1 | 9/2005 | Lauk et al. |
| 2005/0211249 A1 | 9/2005 | Wagner et al. |
| 2005/0217674 A1* | 10/2005 | Burton ................. A61M 16/10 128/204.23 |
| 2005/0224078 A1 | 10/2005 | Zdrojkowski et al. |
| 2005/0241639 A1 | 11/2005 | Zilberg |
| 2005/0247315 A1 | 11/2005 | Estes et al. |
| 2005/0251218 A1 | 11/2005 | Markowitz et al. |
| 2005/0261600 A1 | 11/2005 | Aylsworth |
| 2005/0267362 A1 | 12/2005 | Mietus et al. |
| 2005/0267380 A1 | 12/2005 | Poezevara |
| 2005/0273361 A1 | 12/2005 | Busch |
| 2005/0277842 A1 | 12/2005 | Silva |
| 2005/0283089 A1 | 12/2005 | Sullivan et al. |
| 2005/0288572 A1 | 12/2005 | Graw |
| 2005/0288728 A1 | 12/2005 | Libbus et al. |
| 2005/0288729 A1 | 12/2005 | Libbus et al. |
| 2006/0000475 A1 | 1/2006 | Matthews et al. |
| 2006/0004245 A1 | 1/2006 | Pickett et al. |
| 2006/0009708 A1 | 1/2006 | Rapoport et al. |
| 2006/0011200 A1 | 1/2006 | Remmers et al. |
| 2006/0025696 A1 | 2/2006 | Kurzweil et al. |
| 2006/0025697 A1 | 2/2006 | Kurzweil et al. |
| 2006/0030894 A1 | 2/2006 | Tehrani |
| 2006/0036294 A1 | 2/2006 | Tehrani |
| 2006/0037615 A1 | 2/2006 | Wilkinson et al. |
| 2006/0039866 A1 | 2/2006 | Rao et al. |

(56) References Cited

U.S. PATENT DOCUMENTS

| | | |
|---|---|---|
| 2006/0039867 A1 | 2/2006 | Rao et al. |
| 2006/0047217 A1 | 3/2006 | Mirtalebi et al. |
| 2006/0050930 A1 | 3/2006 | Szuba |
| 2006/0079802 A1 | 4/2006 | Jensen et al. |
| 2006/0084877 A1 | 4/2006 | Ujhazy et al. |
| 2006/0087325 A1 | 4/2006 | Ariav et al. |
| 2006/0095088 A1 | 5/2006 | De Ridder |
| 2006/0102179 A1 | 5/2006 | Rapoport et al. |
| 2006/0112960 A1 | 6/2006 | Wickham |
| 2006/0118112 A1 | 6/2006 | Cattano et al. |
| 2006/0122127 A1 | 6/2006 | Rao et al. |
| 2006/0122675 A1 | 6/2006 | Libbus et al. |
| 2006/0128605 A1 | 6/2006 | Shibahara et al. |
| 2006/0134106 A1 | 6/2006 | Adair |
| 2006/0135878 A1 | 6/2006 | Wright et al. |
| 2006/0145878 A1 | 7/2006 | Lehrman et al. |
| 2006/0149144 A1 | 7/2006 | Lynn et al. |
| 2006/0154856 A1 | 7/2006 | Veasey |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174889 A1 | 8/2006 | Noble |
| 2006/0179571 A1 | 8/2006 | Newkirk |
| 2006/0189872 A1 | 8/2006 | Arnold |
| 2006/0189880 A1 | 8/2006 | Lynn et al. |
| 2006/0195041 A1 | 8/2006 | Lynn et al. |
| 2006/0212081 A1 | 9/2006 | Suga et al. |
| 2006/0228775 A1 | 10/2006 | Collier et al. |
| 2006/0229489 A1 | 10/2006 | Pickett et al. |
| 2006/0235315 A1 | 10/2006 | Akselrod et al. |
| 2006/0235324 A1 | 10/2006 | Lynn |
| 2006/0241164 A1 | 10/2006 | Radulovacki et al. |
| 2006/0241510 A1 | 10/2006 | Halperin et al. |
| 2006/0258916 A1 | 11/2006 | Pietersen |
| 2006/0258921 A1 | 11/2006 | Addison et al. |
| 2006/0258948 A1 | 11/2006 | Linville |
| 2006/0264770 A1 | 11/2006 | Wellens et al. |
| 2006/0272641 A1 | 12/2006 | Madaus et al. |
| 2006/0275313 A1 | 12/2006 | Clark et al. |
| 2006/0276695 A9 | 12/2006 | Lynn et al. |
| 2006/0276701 A1 | 12/2006 | Ray |
| 2006/0279428 A1 | 12/2006 | Sato et al. |
| 2006/0293604 A1 | 12/2006 | Carlson et al. |
| 2007/0021589 A1 | 1/2007 | Collier et al. |
| 2007/0021795 A1 | 1/2007 | Tehrani |
| 2007/0032733 A1 | 2/2007 | Burton |
| 2007/0044796 A1 | 3/2007 | Zdrojkowski et al. |
| 2007/0051371 A1 | 3/2007 | Sullivan et al. |
| 2007/0055115 A1 | 3/2007 | Kwok et al. |
| 2007/0055168 A1 | 3/2007 | Rapoport et al. |
| 2007/0061393 A1 | 3/2007 | Moore |
| 2007/0062540 A1 | 3/2007 | Murray-Harris |
| 2007/0073177 A1 | 3/2007 | Kontothanassis et al. |
| 2007/0073181 A1 | 3/2007 | Pu et al. |
| 2007/0084464 A1 | 4/2007 | Wickham et al. |
| 2007/0093721 A1 | 4/2007 | Lynn et al. |
| 2007/0100381 A1 | 5/2007 | Snyder et al. |
| 2007/0106536 A1 | 5/2007 | Moore |
| 2007/0106537 A1 | 5/2007 | Moore |
| 2007/0106750 A1 | 5/2007 | Moore |
| 2007/0106751 A1 | 5/2007 | Moore |
| 2007/0106752 A1 | 5/2007 | Moore |
| 2007/0106753 A1 | 5/2007 | Moore |
| 2007/0106754 A1 | 5/2007 | Moore |
| 2007/0116036 A1 | 5/2007 | Moore |
| 2007/0116037 A1 | 5/2007 | Moore |
| 2007/0118180 A1 | 5/2007 | Ni et al. |
| 2007/0123517 A1 | 5/2007 | Radulovacki et al. |
| 2007/0129643 A1 | 6/2007 | Kwok et al. |
| 2007/0129645 A1 | 6/2007 | Hartley et al. |
| 2007/0129647 A1 | 6/2007 | Lynn |
| 2007/0135335 A1 | 6/2007 | Collier et al. |
| 2007/0135724 A1 | 6/2007 | Ujhazy et al. |
| 2007/0137653 A1 | 6/2007 | Wood |
| 2007/0142713 A1 | 6/2007 | Lancaster et al. |
| 2007/0142741 A1 | 6/2007 | Berthon-Jones et al. |
| 2007/0149860 A1 | 6/2007 | Lynn et al. |
| 2007/0150022 A1 | 6/2007 | Ujhazy et al. |
| 2007/0156059 A1 | 7/2007 | Vitali et al. |
| 2007/0156060 A1 | 7/2007 | Cervantes |
| 2007/0161917 A1 | 7/2007 | Ozaki et al. |
| 2007/0167694 A1 | 7/2007 | Causevic et al. |
| 2007/0168461 A1 | 7/2007 | Moore |
| 2007/0173728 A1 | 7/2007 | Pu et al. |
| 2007/0173893 A1 | 7/2007 | Pitts |
| 2007/0191688 A1 | 8/2007 | Lynn |
| 2007/0191697 A1 | 8/2007 | Lynn et al. |
| 2007/0199262 A1 | 8/2007 | Kern et al. |
| 2007/0208235 A1 | 9/2007 | Besson et al. |
| 2007/0213620 A1 | 9/2007 | Reisfeld |
| 2007/0213621 A1 | 9/2007 | Reisfeld et al. |
| 2007/0213622 A1 | 9/2007 | Reisfeld |
| 2007/0213624 A1 | 9/2007 | Reisfeld et al. |
| 2007/0215146 A1 | 9/2007 | Douglas et al. |
| 2007/0221224 A1 | 9/2007 | Pittman et al. |
| 2007/0227539 A1 | 10/2007 | Schwaibold et al. |
| 2007/0239057 A1 | 10/2007 | Pu et al. |
| 2007/0240718 A1 | 10/2007 | Daly |
| 2007/0251527 A1 | 11/2007 | Sleeper |
| 2007/0255160 A1 | 11/2007 | Daly |
| 2007/0255310 A1 | 11/2007 | Hovanes et al. |
| 2007/0265539 A1 | 11/2007 | Hastings et al. |
| 2007/0273366 A1 | 11/2007 | Ansay et al. |
| 2007/0277832 A1 | 12/2007 | Doshi et al. |
| 2007/0282212 A1 | 12/2007 | Sierra et al. |
| 2007/0293907 A1 | 12/2007 | Dubnov et al. |
| 2007/0295338 A1 | 12/2007 | Loomas et al. |
| 2008/0009755 A1 | 1/2008 | Patangay et al. |
| 2008/0015454 A1 | 1/2008 | Gal |
| 2008/0015457 A1 | 1/2008 | Silva |
| 2008/0027502 A1 | 1/2008 | Ransom |
| 2008/0039730 A1 | 2/2008 | Pu et al. |
| 2008/0039904 A1 | 2/2008 | Bulkes et al. |
| 2008/0040151 A1 | 2/2008 | Moore |
| 2008/0041382 A1 | 2/2008 | Matthews et al. |
| 2008/0041383 A1 | 2/2008 | Matthews et al. |
| 2008/0045813 A1 | 2/2008 | Phuah et al. |
| 2008/0045832 A1 | 2/2008 | McGrath |
| 2008/0051845 A1 | 2/2008 | Mentelos |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0058665 A1 | 3/2008 | Scholler et al. |
| 2008/0058873 A1 | 3/2008 | Lee et al. |
| 2008/0058892 A1 | 3/2008 | Haefner et al. |
| 2008/0060138 A1 | 3/2008 | Price et al. |
| 2008/0066753 A1 | 3/2008 | Martin et al. |
| 2008/0071185 A1 | 3/2008 | Beck et al. |
| 2008/0081961 A1 | 4/2008 | Westbrook et al. |
| 2008/0082016 A1 | 4/2008 | Kohls et al. |
| 2008/0082659 A1 | 4/2008 | Haslehurst et al. |
| 2008/0091082 A1 | 4/2008 | Lu |
| 2008/0092898 A1 | 4/2008 | Schneider et al. |
| 2008/0101532 A1 | 5/2008 | Tkaczyk et al. |
| 2008/0139948 A1 | 6/2008 | Stahmann et al. |
| 2008/0142011 A1 | 6/2008 | Aylsworth et al. |
| 2008/0142013 A1 | 6/2008 | Hallett et al. |
| 2008/0153159 A1 | 6/2008 | Clark et al. |
| 2008/0154110 A1 | 6/2008 | Burnes et al. |
| 2008/0154330 A1 | 6/2008 | Tehrani et al. |
| 2008/0161708 A1 | 7/2008 | Kenigsberg et al. |
| 2008/0161878 A1* | 7/2008 | Tehrani .......... A61N 1/3601 607/42 |
| 2008/0163873 A1 | 7/2008 | Berthon-Jones |
| 2008/0167567 A1 | 7/2008 | Bashour et al. |
| 2008/0167695 A1 | 7/2008 | Tehrani et al. |
| 2008/0170654 A1 | 7/2008 | Tkaczyk et al. |
| 2008/0177347 A1 | 7/2008 | Tehrani et al. |
| 2008/0177789 A1 | 7/2008 | Stoval |
| 2008/0183095 A1 | 7/2008 | Austin et al. |
| 2008/0183239 A1 | 7/2008 | Tehrani et al. |
| 2008/0183240 A1 | 7/2008 | Tehrani et al. |
| 2008/0188904 A1 | 8/2008 | Tehrani et al. |
| 2008/0190430 A1 | 8/2008 | Melker et al. |

(56) References Cited

U.S. PATENT DOCUMENTS

| | | |
|---|---|---|
| 2008/0190436 A1 | 8/2008 | Jaffe et al. |
| 2008/0200367 A1 | 8/2008 | Carley et al. |
| 2008/0215106 A1 | 9/2008 | Lee et al. |
| 2008/0221468 A1 | 9/2008 | Stahmann et al. |
| 2008/0243021 A1 | 10/2008 | Causevic et al. |
| 2008/0257349 A1 | 10/2008 | Hedner et al. |
| 2008/0261922 A1 | 10/2008 | Carley et al. |
| 2008/0262360 A1 | 10/2008 | Dalal et al. |
| 2008/0264426 A1 | 10/2008 | Walker |
| 2008/0269583 A1 | 10/2008 | Reisfeld |
| 2008/0269625 A1 | 10/2008 | Halperin et al. |
| 2008/0287769 A1 | 11/2008 | Kurzweil et al. |
| 2008/0287770 A1 | 11/2008 | Kurzweil et al. |
| 2008/0288010 A1 | 11/2008 | Tehrani et al. |
| 2008/0288013 A1 | 11/2008 | Schecter |
| 2008/0288015 A1 | 11/2008 | Tehrani et al. |
| 2008/0289631 A1 | 11/2008 | Schroeder et al. |
| 2008/0300499 A1 | 12/2008 | Strube |
| 2008/0300500 A1 | 12/2008 | Reisfeld |
| 2008/0302364 A1 | 12/2008 | Garde et al. |
| 2008/0308105 A1 | 12/2008 | Alder et al. |
| 2008/0308112 A1 | 12/2008 | Aarts |
| 2008/0312548 A1 | 12/2008 | Hartley et al. |
| 2008/0313816 A1 | 12/2008 | Bohm et al. |
| 2008/0319513 A1 | 12/2008 | Pu et al. |
| 2009/0005357 A1 | 1/2009 | Radulovacki et al. |
| 2009/0030335 A1 | 1/2009 | Kuchler |
| 2009/0036790 A1 | 2/2009 | Landesberg et al. |
| 2009/0038617 A1 | 2/2009 | Berthon-Jones et al. |
| 2009/0050154 A1 | 2/2009 | Strothmann et al. |
| 2009/0062628 A1 | 3/2009 | Yamamoto et al. |
| 2009/0062675 A1 | 3/2009 | Weigand et al. |
| 2009/0069419 A1 | 3/2009 | Jandeleit et al. |
| 2009/0076147 A1 | 3/2009 | Jandeleit et al. |
| 2009/0076364 A1* | 3/2009 | Libbus ............. A61B 5/282 600/391 |
| 2009/0078256 A1 | 3/2009 | Armitstead et al. |
| 2009/0082440 A1 | 3/2009 | Jandeleit et al. |
| 2009/0082464 A1 | 3/2009 | Jandeleit et al. |
| 2009/0082639 A1 | 3/2009 | Pittman et al. |
| 2009/0099253 A1 | 4/2009 | Li et al. |
| 2009/0099462 A1 | 4/2009 | Almen |
| 2009/0099469 A1 | 4/2009 | Flores |
| 2009/0107498 A1 | 4/2009 | Plattner et al. |
| 2009/0112116 A1 | 4/2009 | Lee et al. |
| 2009/0118629 A1 | 5/2009 | Lin et al. |
| 2009/0136444 A1 | 5/2009 | Priest et al. |
| 2009/0142294 A1 | 6/2009 | Priest et al. |
| 2009/0149496 A1 | 6/2009 | Brendel et al. |
| 2009/0149778 A1 | 6/2009 | Naujokat et al. |
| 2009/0155267 A1 | 6/2009 | Priest et al. |
| 2009/0156650 A1 | 6/2009 | Baud et al. |
| 2009/0172773 A1 | 7/2009 | Moore |
| 2009/0173347 A1 | 7/2009 | Berthon-Jones |
| 2009/0175819 A1 | 7/2009 | Priest et al. |
| 2009/0177050 A1 | 7/2009 | Griffiths et al. |
| 2009/0177495 A1 | 7/2009 | Abousy et al. |
| 2009/0177702 A1 | 7/2009 | Stahmann et al. |
| 2009/0183312 A1 | 7/2009 | Price et al. |
| 2009/0202472 A1 | 8/2009 | Priest et al. |
| 2009/0203972 A1 | 8/2009 | Heneghan et al. |
| 2009/0209880 A1 | 8/2009 | Jensen et al. |
| 2009/0221658 A1 | 9/2009 | Radulovacki et al. |
| 2009/0226861 A1 | 9/2009 | Thieberger Ben-Haom et al. |
| 2009/0226862 A1 | 9/2009 | Thieberger Ben-Haom et al. |
| 2009/0226863 A1 | 9/2009 | Thieberger Ben-Haim et al. |
| 2009/0226864 A1 | 9/2009 | Thieberger Ben-Haim et al. |
| 2009/0226865 A1 | 9/2009 | Thieberger Ben-Haim et al. |
| 2009/0232808 A1 | 9/2009 | Priest et al. |
| 2009/0238819 A1 | 9/2009 | Clark et al. |
| 2009/0240126 A1 | 9/2009 | Baker, Jr. et al. |
| 2009/0270773 A1 | 10/2009 | Hoffmann |
| 2009/0306528 A1 | 12/2009 | Curti et al. |
| 2009/0306529 A1 | 12/2009 | Curti et al. |
| 2009/0308395 A1 | 12/2009 | Lee et al. |
| 2009/0311247 A1 | 12/2009 | Priest et al. |
| 2009/0318820 A1 | 12/2009 | Toledo et al. |
| 2009/0326402 A1 | 12/2009 | Addison et al. |
| 2009/0326981 A1 | 12/2009 | Karkanias et al. |
| 2010/0004549 A1 | 1/2010 | Kohls et al. |
| 2010/0010359 A1 | 1/2010 | Kenigsberg et al. |
| 2010/0016694 A1 | 1/2010 | Martin et al. |
| 2010/0016783 A1 | 1/2010 | Bourke, Jr. et al. |
| 2010/0018530 A1 | 1/2010 | Schindhelm et al. |
| 2010/0030085 A1 | 2/2010 | Rojas Ojeda et al. |
| 2010/0031959 A1 | 2/2010 | Avidor et al. |
| 2010/0036209 A1 | 2/2010 | Ferren et al. |
| 2010/0036263 A1 | 2/2010 | Ferren et al. |
| 2010/0036268 A1 | 2/2010 | Ferren et al. |
| 2010/0036269 A1 | 2/2010 | Ferren et al. |
| 2010/0043795 A1 | 2/2010 | Ujhazy et al. |
| 2010/0056850 A1 | 3/2010 | Pickett et al. |
| 2010/0063438 A1 | 3/2010 | Bengtsson |
| 2010/0069762 A1 | 3/2010 | Mietus et al. |
| 2010/0079292 A1 | 4/2010 | Lynn et al. |
| 2010/0081943 A1 | 4/2010 | Watson et al. |
| 2010/0095959 A1 | 4/2010 | Farrell |
| 2010/0099963 A1 | 4/2010 | Kilger |
| 2010/0106211 A1 | 4/2010 | Lee et al. |
| 2010/0113955 A1 | 5/2010 | Colman et al. |
| 2010/0113956 A1 | 5/2010 | Curti et al. |
| 2010/0121207 A1 | 5/2010 | Moersdorf et al. |
| 2010/0130873 A1 | 5/2010 | Yuen et al. |
| 2010/0137251 A1 | 6/2010 | Carley et al. |
| 2010/0137723 A1 | 6/2010 | Patangay et al. |
| 2010/0145201 A1 | 6/2010 | Westbrook et al. |
| 2010/0152553 A1 | 6/2010 | Ujhazy et al. |
| 2010/0152600 A1 | 6/2010 | Droitcour et al. |
| 2010/0159426 A1 | 6/2010 | Thieberger Ben-Haim et al. |
| 2010/0168578 A1 | 7/2010 | Garson, Jr. et al. |
| 2010/0168600 A1 | 7/2010 | Adriance et al. |
| 2010/0168601 A1 | 7/2010 | Adriance et al. |
| 2010/0174154 A1 | 7/2010 | Lee et al. |
| 2010/0174161 A1 | 7/2010 | Lynn |
| 2010/0174207 A1 | 7/2010 | Lee et al. |
| 2010/0174335 A1 | 7/2010 | Stahmann et al. |
| 2010/0179396 A1 | 7/2010 | Lin et al. |
| 2010/0179613 A1 | 7/2010 | Stahmann et al. |
| 2010/0198083 A1 | 8/2010 | Lin et al. |
| 2010/0198289 A1 | 8/2010 | Kameli et al. |
| 2010/0204550 A1 | 8/2010 | Heneghan et al. |
| 2010/0204586 A1 | 8/2010 | Pu et al. |
| 2010/0222655 A1 | 9/2010 | Starr et al. |
| 2010/0222685 A1 | 9/2010 | Berthon-Jones et al. |
| 2010/0222689 A1 | 9/2010 | Kurzweil et al. |
| 2010/0228120 A1 | 9/2010 | Thijs et al. |
| 2010/0228317 A1 | 9/2010 | Libbus et al. |
| 2010/0234705 A1 | 9/2010 | Lynn |
| 2010/0234750 A1 | 9/2010 | Ariav et al. |
| 2010/0240999 A1 | 9/2010 | Droitcour et al. |
| 2010/0242965 A1 | 9/2010 | Berthon-Jones |
| 2010/0249630 A1 | 9/2010 | Droitcour et al. |
| 2010/0249633 A1 | 9/2010 | Droitcour et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0253505 A1 | 10/2010 | Chou |
| 2010/0256460 A1 | 10/2010 | Haveri et al. |
| 2010/0256512 A1 | 10/2010 | Sullivan |
| 2010/0258123 A1 | 10/2010 | Somaiya et al. |
| 2010/0258126 A1 | 10/2010 | Ujhazy et al. |
| 2010/0262035 A1 | 10/2010 | Subramanian |
| 2010/0262205 A1 | 10/2010 | De Ridder |
| 2010/0268093 A1 | 10/2010 | Balji et al. |
| 2010/0292568 A1 | 11/2010 | Droitcour et al. |
| 2010/0297129 A1 | 11/2010 | Adair |
| 2010/0298733 A1 | 11/2010 | Kwok et al. |
| 2010/0307500 A1 | 12/2010 | Armitstead |
| 2010/0319709 A1 | 12/2010 | Goncalves |
| 2010/0326447 A1 | 12/2010 | Loomas et al. |
| 2010/0328075 A1 | 12/2010 | Rahamim et al. |
| 2010/0331715 A1 | 12/2010 | Addison et al. |

(56) References Cited

U.S. PATENT DOCUMENTS

| | | |
|---|---|---|
| 2010/0331716 A1 | 12/2010 | Watson et al. |
| 2011/0004081 A1 | 1/2011 | Addison et al. |
| 2011/0009722 A1 | 1/2011 | Amundson et al. |
| 2011/0011402 A1 | 1/2011 | Berthon-Jones |
| 2011/0015501 A1 | 1/2011 | Lynn et al. |
| 2011/0021928 A1 | 1/2011 | Giovangrandi et al. |
| 2011/0021970 A1 | 1/2011 | Vo-Dinh et al. |
| 2011/0028802 A1 | 2/2011 | Addison et al. |
| 2011/0034820 A1 | 2/2011 | Pietersen |
| 2011/0036352 A1 | 2/2011 | Estes et al. |
| 2011/0040201 A1 | 2/2011 | Pu et al. |
| 2011/0046462 A1 | 2/2011 | Ono et al. |
| 2011/0046500 A1 | 2/2011 | Haveri |
| 2011/0054270 A1 | 3/2011 | Derchak |
| 2011/0054279 A1 | 3/2011 | Reisfeld et al. |
| 2011/0054290 A1 | 3/2011 | Derchak |
| 2011/0060380 A1 | 3/2011 | Gelfand et al. |
| 2011/0061647 A1 | 3/2011 | Stahmann et al. |
| 2011/0067709 A1 | 3/2011 | Doshi et al. |
| 2011/0087115 A1 | 4/2011 | Sackner et al. |
| 2011/0097333 A1 | 4/2011 | Clark et al. |
| 2011/0105869 A1 | 5/2011 | Wilson et al. |
| 2011/0105921 A1 | 5/2011 | Wang |
| 2011/0130249 A1 | 6/2011 | Mikhailenok et al. |
| 2011/0131057 A1 | 6/2011 | Newkirk |
| 2011/0137197 A1 | 6/2011 | Stahmann et al. |
| 2011/0137367 A1 | 6/2011 | Carlson et al. |
| 2011/0152706 A1 | 6/2011 | Christopherson et al. |
| 2011/0160601 A1 | 6/2011 | Wang et al. |
| 2011/0166470 A1 | 7/2011 | Rapoport et al. |
| 2011/0172552 A1 | 7/2011 | Rothman et al. |
| 2011/0184298 A1 | 7/2011 | De Marchena et al. |
| 2011/0184304 A1 | 7/2011 | Koh |
| 2011/0186050 A1 | 8/2011 | Daly |
| 2011/0190594 A1 | 8/2011 | Heit et al. |
| 2011/0190651 A1 | 8/2011 | Ota et al. |
| 2011/0192400 A9 | 8/2011 | Burton et al. |
| 2011/0208082 A1 | 8/2011 | Madaus et al. |
| 2011/0208539 A1 | 8/2011 | Lynn |
| 2011/0214676 A1 | 9/2011 | Allum et al. |
| 2011/0217719 A1 | 9/2011 | Gozal et al. |
| 2011/0230727 A1 | 9/2011 | Sanders et al. |
| 2011/0230932 A1 | 9/2011 | Tehrani et al. |
| 2011/0245628 A1 | 10/2011 | Baker, Jr. et al. |
| 2011/0245706 A1 | 10/2011 | Lu |
| 2011/0264164 A1 | 10/2011 | Christopherson et al. |
| 2011/0270114 A1 | 11/2011 | Addison et al. |
| 2011/0284003 A1 | 11/2011 | Douglas et al. |
| 2011/0288609 A1 | 11/2011 | Tehrani et al. |
| 2011/0297156 A1 | 12/2011 | Shelly et al. |
| 2011/0301435 A1 | 12/2011 | Albert et al. |
| 2011/0301439 A1 | 12/2011 | Albert et al. |
| 2011/0301484 A1 | 12/2011 | Curti et al. |
| 2011/0301487 A1 | 12/2011 | Abeyratne et al. |
| 2011/0303223 A1 | 12/2011 | Kane et al. |
| 2011/0306850 A1 | 12/2011 | Hatlestad et al. |
| 2011/0313689 A1 | 12/2011 | Holley et al. |
| 2011/0319777 A1 | 12/2011 | Mehrotra et al. |
| 2012/0004523 A1 | 1/2012 | Richter et al. |
| 2012/0004749 A1 | 1/2012 | Abeyratne et al. |
| 2012/0010198 A1 | 1/2012 | Carley et al. |
| 2012/0017904 A1 | 1/2012 | Ratto et al. |
| 2012/0022348 A1 | 1/2012 | Droitcour et al. |
| 2012/0028504 A1 | 2/2012 | Coggins et al. |
| 2012/0029362 A1 | 2/2012 | Patangay et al. |
| 2012/0032778 A1 | 2/2012 | Nakano et al. |
| 2012/0035436 A1 | 2/2012 | Kirchner et al. |
| 2012/0041037 A1 | 2/2012 | Baud et al. |
| 2012/0046709 A1 | 2/2012 | Lee et al. |
| 2012/0053480 A1 | 3/2012 | Ueda |
| 2012/0056746 A1 | 3/2012 | Kaigler et al. |
| 2012/0065533 A1 | 3/2012 | Carrillo, Jr. et al. |
| 2012/0078319 A1 | 3/2012 | De Ridder |
| 2012/0088998 A1 | 4/2012 | Bardy et al. |
| 2012/0101690 A1 | 4/2012 | Srinivasan et al. |
| 2012/0108570 A1 | 5/2012 | Radulovacki et al. |
| 2012/0109027 A1 | 5/2012 | Gozelski, Jr. et al. |
| 2012/0116187 A1 | 5/2012 | Hayes et al. |
| 2012/0125337 A1 | 5/2012 | Asanoi |
| 2012/0130204 A1 | 5/2012 | Basta et al. |
| 2012/0130205 A1 | 5/2012 | Burton et al. |
| 2012/0130445 A1 | 5/2012 | Lee et al. |
| 2012/0130446 A1 | 5/2012 | Haefner et al. |
| 2012/0132202 A1 | 5/2012 | Burton et al. |
| 2012/0136231 A1 | 5/2012 | Markel |
| 2012/0136405 A1 | 5/2012 | Burton et al. |
| 2012/0145153 A1 | 6/2012 | Bassin et al. |
| 2012/0152252 A1 | 6/2012 | Matthews et al. |
| 2012/0157900 A1 | 6/2012 | Iyer et al. |
| 2012/0158091 A1 | 6/2012 | Tehrani et al. |
| 2012/0160243 A1 | 6/2012 | Berthon-Jones et al. |
| 2012/0165711 A1 | 6/2012 | Pickett et al. |
| 2012/0172689 A1 | 7/2012 | Albert et al. |
| 2012/0172730 A1 | 7/2012 | Delos et al. |
| 2012/0173470 A1 | 7/2012 | Bashour et al. |
| 2012/0179061 A1 | 7/2012 | Ramanan et al. |
| 2012/0189632 A1 | 7/2012 | Adair |
| 2012/0190998 A1 | 7/2012 | Armitstead et al. |
| 2012/0197144 A1 | 8/2012 | Christ et al. |
| 2012/0203491 A1 | 8/2012 | Sun et al. |
| 2012/0209096 A1 | 8/2012 | Jaffe et al. |
| 2012/0209127 A1 | 8/2012 | Jensen et al. |
| 2012/0227740 A1 | 9/2012 | Berthon-Jones et al. |
| 2012/0232398 A1 | 9/2012 | Roham et al. |
| 2012/0232416 A1 | 9/2012 | Gilham et al. |
| 2012/0234323 A1 | 9/2012 | Connor |
| 2012/0240934 A1 | 9/2012 | Holzrichter |
| 2012/0245437 A1 | 9/2012 | Lovett et al. |
| 2012/0252709 A1 | 10/2012 | Felts et al. |
| 2012/0253249 A1 | 10/2012 | Wilson |
| 2012/0255553 A1 | 10/2012 | Wood |
| 2012/0272429 A1 | 11/2012 | Porporino et al. |
| 2012/0283527 A1 | 11/2012 | Pu et al. |
| 2012/0283581 A1 | 11/2012 | Olde et al. |
| 2012/0291785 A1 | 11/2012 | Ramanan et al. |
| 2012/0302845 A1 | 11/2012 | Lynn et al. |
| 2012/0304998 A1 | 12/2012 | Wickham et al. |
| 2012/0323104 A1 | 12/2012 | Burnes et al. |
| 2012/0323293 A1 | 12/2012 | Tehrani et al. |
| 2012/0330118 A1 | 12/2012 | Lynn et al. |
| 2012/0330123 A1 | 12/2012 | Doerr |
| 2013/0012827 A1 | 1/2013 | Kurzweil et al. |
| 2013/0012830 A1* | 1/2013 | Leininger .......... A61B 5/02055 600/546 |
| 2013/0019870 A1 | 1/2013 | Collazo et al. |
| 2013/0030257 A1 | 1/2013 | Nakata et al. |
| 2013/0030711 A1 | 1/2013 | Korhonen |
| 2013/0046151 A1 | 2/2013 | Bsoul et al. |
| 2013/0046156 A1 | 2/2013 | Addison et al. |
| 2013/0046157 A1 | 2/2013 | Addison et al. |
| 2013/0046160 A1 | 2/2013 | Addison et al. |
| 2013/0046161 A1 | 2/2013 | Addison et al. |
| 2013/0046184 A1 | 2/2013 | Addison et al. |
| 2013/0046185 A1 | 2/2013 | Addison et al. |
| 2013/0046186 A1 | 2/2013 | Addison et al. |
| 2013/0046187 A1 | 2/2013 | Addison et al. |
| 2013/0046188 A1 | 2/2013 | Addison et al. |
| 2013/0053674 A1 | 2/2013 | Volker |
| 2013/0060110 A1 | 3/2013 | Lynn et al. |
| 2013/0060149 A1 | 3/2013 | Song et al. |
| 2013/0060150 A1 | 3/2013 | Song et al. |
| 2013/0060480 A1 | 3/2013 | Korhonen et al. |
| 2013/0079842 A1 | 3/2013 | Mokelke et al. |
| 2013/0081479 A1 | 4/2013 | Miller et al. |
| 2013/0085688 A1 | 4/2013 | Miller et al. |
| 2013/0096442 A1 | 4/2013 | Stahmann et al. |
| 2013/0096447 A1 | 4/2013 | Dhawan et al. |
| 2013/0096450 A1 | 4/2013 | Duckert et al. |
| 2013/0104898 A1 | 5/2013 | Berthon-Jones |
| 2013/0118494 A1 | 5/2013 | Ujhazy et al. |
| 2013/0123654 A1 | 5/2013 | Rahimim et al. |
| 2013/0131028 A1 | 5/2013 | Snyder et al. |
| 2013/0131522 A1 | 5/2013 | Patangay et al. |
| 2013/0137998 A1 | 5/2013 | Lange et al. |

(56) References Cited

U.S. PATENT DOCUMENTS

| | | |
|---|---|---|
| 2013/0144178 A1 | 6/2013 | Halperin et al. |
| 2013/0146056 A1 | 6/2013 | Baker, Jr. et al. |
| 2013/0158625 A1 | 6/2013 | Gelfand et al. |
| 2013/0165809 A1 | 6/2013 | Abir |
| 2013/0172720 A1 | 7/2013 | Yamamori et al. |
| 2013/0172759 A1 | 7/2013 | Melker et al. |
| 2013/0174847 A1 | 7/2013 | Berthon-Jones |
| 2013/0178719 A1 | 7/2013 | Balji et al. |
| 2013/0178761 A1 | 7/2013 | Alder et al. |
| 2013/0197321 A1 | 8/2013 | Wilson |
| 2013/0197601 A1 | 8/2013 | Tehrani et al. |
| 2013/0199532 A1 | 8/2013 | Shissler et al. |
| 2013/0211210 A1 | 8/2013 | Freeman |
| 2013/0218030 A1 | 8/2013 | Barroso et al. |
| 2013/0231713 A1 | 9/2013 | De Ridder |
| 2013/0234535 A1 | 9/2013 | Sako et al. |
| 2013/0238052 A1 | 9/2013 | Libbus et al. |
| 2013/0239960 A1 | 9/2013 | Bertinetti et al. |
| 2013/0255683 A2 | 10/2013 | Kapust et al. |
| 2013/0261485 A1 | 10/2013 | Ishikawa et al. |
| 2013/0268030 A1 | 10/2013 | Lee et al. |
| 2013/0276785 A1 | 10/2013 | Melker et al. |
| 2013/0281815 A1 | 10/2013 | Varadan |
| 2013/0281874 A1 | 10/2013 | Nishida |
| 2013/0281883 A1 | 10/2013 | Nishida |
| 2013/0291060 A1 | 10/2013 | Moore |
| 2013/0291869 A1 | 11/2013 | Daly |
| 2013/0296660 A1 | 11/2013 | Tsien et al. |
| 2013/0296823 A1 | 11/2013 | Melker et al. |
| 2013/0296964 A1 | 11/2013 | Tehrani |
| 2013/0300575 A1 | 11/2013 | Kurzweil et al. |
| 2013/0307685 A1 | 11/2013 | Sholder |
| 2013/0310657 A1 | 11/2013 | Sullivan et al. |
| 2013/0312752 A2 | 11/2013 | Kapust et al. |
| 2013/0312757 A1 | 11/2013 | Cragg et al. |
| 2013/0324877 A1 | 12/2013 | Nonaka et al. |
| 2013/0331663 A1 | 12/2013 | Albert et al. |
| 2013/0331722 A1 | 12/2013 | Rodriguez-Villegas et al. |
| 2013/0333696 A1 | 12/2013 | Lee et al. |
| 2013/0338459 A1 | 12/2013 | Lynn et al. |
| 2013/0340500 A1 | 12/2013 | Miller et al. |
| 2014/0012099 A1 | 1/2014 | Halperin et al. |
| 2014/0012145 A1 | 1/2014 | Kurzweil et al. |
| 2014/0018779 A1 | 1/2014 | Worrell et al. |
| 2014/0020687 A1 | 1/2014 | Cullen et al. |
| 2014/0025141 A1 | 1/2014 | Haefner et al. |
| 2014/0031705 A1 | 1/2014 | Kurzweil et al. |
| 2014/0031709 A1 | 1/2014 | Toledo et al. |
| 2014/0045755 A1 | 2/2014 | Carley et al. |
| 2014/0051938 A1 | 2/2014 | Goldstein et al. |
| 2014/0053846 A1 | 2/2014 | Wood |
| 2014/0058274 A1 | 2/2014 | Landesberg et al. |
| 2014/0066741 A1 | 3/2014 | Peterson et al. |
| 2014/0066798 A1 | 3/2014 | Albert |
| 2014/0069428 A1 | 3/2014 | Sears et al. |
| 2014/0073969 A1 | 3/2014 | Zou et al. |
| 2014/0094669 A1 | 4/2014 | Jaffe et al. |
| 2014/0100628 A1 | 4/2014 | Pu et al. |
| 2014/0107501 A1 | 4/2014 | Komanduri et al. |
| 2014/0107506 A1 | 4/2014 | Lee et al. |
| 2014/0109909 A1 | 4/2014 | Shelly et al. |
| 2014/0116442 A1 | 5/2014 | Martin et al. |
| 2014/0128697 A1 | 5/2014 | Parfenova et al. |
| 2014/0128761 A1 | 5/2014 | Cline et al. |
| 2014/0142457 A1 | 5/2014 | Armitstead et al. |
| 2014/0144438 A1 | 5/2014 | Klasek |
| 2014/0148720 A1 | 5/2014 | Younes |
| 2014/0150793 A1 | 6/2014 | Douglas et al. |
| 2014/0152467 A1 | 6/2014 | Spencer et al. |
| 2014/0152673 A1 | 6/2014 | Lynn et al. |
| 2014/0158124 A1 | 6/2014 | L'her et al. |
| 2014/0163343 A1 | 6/2014 | Heneghan et al. |
| 2014/0163386 A1 | 6/2014 | He et al. |
| 2014/0163897 A1 | 6/2014 | Lynn et al. |
| 2014/0171769 A1 | 6/2014 | Ochs et al. |
| 2014/0171783 A1 | 6/2014 | Schmidt et al. |
| 2014/0178350 A1 | 6/2014 | Vitalis et al. |
| 2014/0180148 A1 | 6/2014 | Coggins et al. |
| 2014/0180154 A1 | 6/2014 | Sierra et al. |
| 2014/0194705 A1 | 7/2014 | Kwok et al. |
| 2014/0194793 A1 | 7/2014 | Nakata et al. |
| 2014/0200476 A1 | 7/2014 | Wickham |
| 2014/0207204 A1 | 7/2014 | Halperin et al. |
| 2014/0213913 A1 | 7/2014 | Parfenova et al. |
| 2014/0213919 A1 | 7/2014 | Poon et al. |
| 2014/0218210 A1 | 8/2014 | De Jong et al. |
| 2014/0221859 A1 | 8/2014 | Albert |
| 2014/0228651 A1 | 8/2014 | Causevic et al. |
| 2014/0238399 A1 | 8/2014 | Daly |
| 2014/0243934 A1 | 8/2014 | Vo-Dinh et al. |
| 2014/0246024 A1 | 9/2014 | Cragg et al. |
| 2014/0246025 A1 | 9/2014 | Cragg et al. |
| 2014/0258743 A1 | 9/2014 | Nool et al. |
| 2014/0261425 A1 | 9/2014 | Connor |
| 2014/0275928 A1 | 9/2014 | Acquista et al. |
| 2014/0276120 A1 | 9/2014 | Starr et al. |
| 2014/0276287 A1 | 9/2014 | Pickett et al. |
| 2014/0283831 A1 | 9/2014 | Foote et al. |
| 2014/0288953 A1 | 9/2014 | Lynn et al. |
| 2014/0309540 A1 | 10/2014 | Morikawa et al. |
| 2014/0309568 A1 | 10/2014 | Pickett et al. |
| 2014/0309943 A1 | 10/2014 | Grundlehner et al. |
| 2014/0320309 A1 | 10/2014 | Zhang et al. |
| 2014/0323946 A1 | 10/2014 | Bourke, Jr. et al. |
| 2014/0326253 A1 | 11/2014 | Baratier et al. |
| 2014/0330155 A1 | 11/2014 | Brewer et al. |
| 2014/0330156 A1 | 11/2014 | Bowman et al. |
| 2014/0330540 A1 | 11/2014 | Lin et al. |
| 2014/0345060 A1 | 11/2014 | Ribble et al. |
| 2014/0363740 A1 | 12/2014 | Holme et al. |
| 2014/0364706 A1 | 12/2014 | Schindhelm et al. |
| 2014/0371635 A1 | 12/2014 | Shinar et al. |
| 2015/0005646 A1 | 1/2015 | Balakrishnan et al. |
| 2015/0005658 A1 | 1/2015 | Nonaka et al. |
| 2015/0018342 A1 | 1/2015 | Bialy et al. |
| 2015/0018660 A1 | 1/2015 | Thomson et al. |
| 2015/0034081 A1 | 2/2015 | Tehrani et al. |
| 2015/0035643 A1 | 2/2015 | Kursun |
| 2015/0038867 A1 | 2/2015 | Armitstead et al. |
| 2015/0039110 A1 | 2/2015 | Abeyratne et al. |
| 2015/0045686 A1 | 2/2015 | Lynn |
| 2015/0057555 A1 | 2/2015 | Milpied |
| 2015/0059755 A1 | 3/2015 | Bassin |
| 2015/0065891 A1 | 3/2015 | Wiesel |
| 2015/0073240 A1 | 3/2015 | Huang et al. |
| 2015/0073285 A1 | 3/2015 | Albert et al. |
| 2015/0088212 A1 | 3/2015 | De Ridder |
| 2015/0101609 A1 | 4/2015 | Melker et al. |
| 2015/0105632 A1 | 4/2015 | Melker et al. |
| 2015/0107594 A1 | 4/2015 | Rapoport et al. |
| 2015/0112202 A1 | 4/2015 | Abir |
| 2015/0114396 A1 | 4/2015 | Ramanan et al. |
| 2015/0115483 A1 | 4/2015 | Miller |
| 2015/0119739 A1 | 4/2015 | Kurzweil et al. |
| 2015/0119740 A1 | 4/2015 | Hernandez et al. |
| 2015/0120067 A1 | 4/2015 | Wing et al. |
| 2015/0122260 A1 | 5/2015 | Daly |
| 2015/0122685 A1 | 5/2015 | Wakeham et al. |
| 2015/0126847 A1 | 5/2015 | Balji et al. |
| 2015/0126879 A1 | 5/2015 | Hoskuldsson et al. |
| 2015/0128941 A1 | 5/2015 | Holley et al. |
| 2015/0136146 A1 | 5/2015 | Hood et al. |
| 2015/0139935 A1 | 5/2015 | Braley et al. |
| 2015/0141766 A1 | 5/2015 | Fine |
| 2015/0141862 A1 | 5/2015 | Montambeau et al. |
| 2015/0141879 A1 | 5/2015 | Harper et al. |
| 2015/0150485 A1 | 6/2015 | Fernando et al. |
| 2015/0150500 A1 | 6/2015 | Armitstead |
| 2015/0151094 A1 | 6/2015 | Lewer |
| 2015/0164322 A1 | 6/2015 | Derchak |
| 2015/0164375 A1 | 6/2015 | Schindhelm et al. |
| 2015/0164433 A1 | 6/2015 | Halperin et al. |
| 2015/0164682 A1 | 6/2015 | Remmers et al. |
| 2015/0165140 A1 | 6/2015 | Cappelli et al. |

(56) References Cited

U.S. PATENT DOCUMENTS

| | | |
|---|---|---|
| 2015/0165147 A1 | 6/2015 | Rapoport et al. |
| 2015/0173672 A1 | 6/2015 | Goldstein |
| 2015/0177264 A1 | 6/2015 | Gozal et al. |
| 2015/0182132 A1 | 7/2015 | Harris et al. |
| 2015/0182713 A1 | 7/2015 | Phuah et al. |
| 2015/0182842 A1 | 7/2015 | Martikka et al. |
| 2015/0190088 A1 | 7/2015 | Chen et al. |
| 2015/0190089 A1 | 7/2015 | Christopherson et al. |
| 2015/0199479 A1 | 7/2015 | Semen et al. |
| 2015/0216448 A1 | 8/2015 | Lotan et al. |
| 2015/0217074 A1 | 8/2015 | Wells et al. |
| 2015/0228176 A1 | 8/2015 | Sholder |
| 2015/0230750 A1 | 8/2015 | McDarby et al. |
| 2015/0238107 A1 | 8/2015 | Acquista et al. |
| 2015/0246195 A1 | 9/2015 | Baker, Jr. et al. |
| 2015/0250963 A1 | 9/2015 | Ramanan et al. |
| 2015/0251016 A1 | 9/2015 | Vo-Dinh et al. |
| 2015/0257653 A1 | 9/2015 | Hyde et al. |
| 2015/0265796 A1 | 9/2015 | Miller et al. |
| 2015/0272934 A1 | 10/2015 | Stein et al. |
| 2015/0282738 A1 | 10/2015 | Thakur et al. |
| 2015/0283383 A1 | 10/2015 | Ternes et al. |
| 2015/0290415 A1 | 10/2015 | Dunn |
| 2015/0290416 A1 | 10/2015 | Klasek |
| 2015/0305634 A1 | 10/2015 | Stergiou |
| 2015/0314098 A1 | 11/2015 | Allum et al. |
| 2015/0320588 A1 | 11/2015 | Connor |
| 2015/0321022 A1 | 11/2015 | Sullivan et al. |
| 2015/0335507 A1 | 11/2015 | Emmons et al. |
| 2015/0335851 A1 | 11/2015 | Cullen et al. |
| 2015/0343161 A1 | 12/2015 | Knepper et al. |
| 2015/0352306 A1 | 12/2015 | Scheiner et al. |
| 2015/0352308 A1 | 12/2015 | Cullen et al. |
| 2015/0352312 A1 | 12/2015 | Wood |
| 2015/0359964 A1 | 12/2015 | Walker et al. |
| 2015/0366468 A1* | 12/2015 | Levy ............... A61B 5/0205 600/526 |
| 2015/0366511 A1 | 12/2015 | Addison et al. |
| 2015/0370320 A1 | 12/2015 | Connor |
| 2015/0374328 A1 | 12/2015 | Ginestet et al. |
| 2016/0004820 A1 | 1/2016 | Moore |
| 2016/0008565 A1 | 1/2016 | Wood |
| 2016/0022145 A1 | 1/2016 | Mostov |
| 2016/0022204 A1 | 1/2016 | Mostov |
| 2016/0029949 A1 | 2/2016 | Landesberg et al. |
| 2016/0029971 A1 | 2/2016 | Sachdev et al. |
| 2016/0030689 A1 | 2/2016 | Landesberg et al. |
| 2016/0045134 A1 | 2/2016 | Jensen et al. |
| 2016/0045166 A1 | 2/2016 | Gheeraert et al. |
| 2016/0045167 A1 | 2/2016 | Gheeraert et al. |
| 2016/0045654 A1 | 2/2016 | Connor |
| 2016/0045695 A1 | 2/2016 | Kapust et al. |
| 2016/0058964 A1 | 3/2016 | Doemer et al. |
| 2016/0066805 A1 | 3/2016 | Scherf et al. |
| 2016/0066809 A1 | 3/2016 | Luo et al. |
| 2016/0067433 A1 | 3/2016 | Martin et al. |
| 2016/0074606 A1 | 3/2016 | Whiting et al. |
| 2016/0089540 A1 | 3/2016 | Bolea |
| 2016/0093196 A1 | 3/2016 | Shinar et al. |
| 2016/0095997 A1 | 4/2016 | Kapust et al. |
| 2016/0100798 A1 | 4/2016 | Markel |
| 2016/0120430 A1 | 5/2016 | Bayasi et al. |
| 2016/0120431 A1 | 5/2016 | Habte et al. |
| 2016/0120433 A1 | 5/2016 | Hughes et al. |
| 2016/0120434 A1 | 5/2016 | Park et al. |
| 2016/0120465 A1 | 5/2016 | Parfenova et al. |
| 2016/0120716 A1 | 5/2016 | Ribble et al. |
| 2016/0128209 A1 | 5/2016 | Yoon et al. |
| 2016/0128863 A1 | 5/2016 | Loomas et al. |
| 2016/0135706 A1 | 5/2016 | Sullivan et al. |
| 2016/0135734 A1 | 5/2016 | Schindhelm |
| 2016/0143594 A1 | 5/2016 | Moorman et al. |
| 2016/0144144 A1 | 5/2016 | Smith et al. |
| 2016/0151014 A1 | 6/2016 | Ujhazy et al. |
| 2016/0151593 A1 | 6/2016 | Rapoport et al. |
| 2016/0151595 A1 | 6/2016 | Rapoport et al. |
| 2016/0158091 A1 | 6/2016 | Amblard et al. |
| 2016/0158092 A1 | 6/2016 | Amblard et al. |
| 2016/0158478 A1 | 6/2016 | Bertinetti et al. |
| 2016/0159793 A1 | 6/2016 | Bialy et al. |
| 2016/0166796 A1 | 6/2016 | Orr |
| 2016/0166797 A1 | 6/2016 | Orr |
| 2016/0169930 A1 | 6/2016 | Korhonen et al. |
| 2016/0174857 A1 | 6/2016 | Eggers et al. |
| 2016/0175552 A1 | 6/2016 | Harrington |
| 2016/0193437 A1 | 7/2016 | Bao et al. |
| 2016/0210747 A1 | 7/2016 | Hay et al. |
| 2016/0220197 A1 | 8/2016 | Rantala |
| 2016/0228024 A1 | 8/2016 | Batzer et al. |
| 2016/0228060 A1 | 8/2016 | Mazar et al. |
| 2016/0232321 A1 | 8/2016 | Silverman |
| 2016/0256063 A1 | 9/2016 | Friedman et al. |
| 2016/0256644 A1 | 9/2016 | Armitstead |
| 2016/0256655 A1 | 9/2016 | Mah et al. |
| 2016/0263376 A1 | 9/2016 | Yoo et al. |
| 2016/0263393 A1 | 9/2016 | Vo-Dinh et al. |
| 2016/0270718 A1 | 9/2016 | Heneghan et al. |
| 2016/0270719 A1 | 9/2016 | Liu et al. |
| 2016/0278658 A1 | 9/2016 | Bardy et al. |
| 2016/0287122 A1 | 10/2016 | Heneghan |
| 2016/0296124 A1 | 10/2016 | Wegerich et al. |
| 2016/0296165 A1 | 10/2016 | Moore et al. |
| 2016/0296720 A1 | 10/2016 | Henry et al. |
| 2016/0302704 A9 | 10/2016 | Lynn et al. |
| 2016/0302726 A1 | 10/2016 | Chang |
| 2016/0310046 A1 | 10/2016 | Heinrich et al. |
| 2016/0310085 A1 | 10/2016 | Delia |
| 2016/0310103 A1 | 10/2016 | Liu et al. |
| 2016/0324467 A1 | 11/2016 | Thakur et al. |
| 2016/0336841 A1 | 11/2016 | Nagorny et al. |
| 2016/0338597 A1 | 11/2016 | Melker et al. |
| 2016/0345897 A1 | 12/2016 | Ni et al. |
| 2016/0354063 A1 | 12/2016 | Ward et al. |
| 2016/0361067 A9 | 12/2016 | Cline et al. |
| 2016/0375209 A1 | 12/2016 | Shadie et al. |
| 2017/0007798 A1 | 1/2017 | Salmon et al. |
| 2017/0014587 A1 | 1/2017 | Whiting et al. |
| 2017/0020919 A1 | 1/2017 | Theus |
| 2017/0035303 A1 | 2/2017 | Sullivan et al. |
| 2017/0035304 A1 | 2/2017 | Shiau |
| 2017/0035978 A1 | 2/2017 | Holley et al. |
| 2017/0128002 A1 | 5/2017 | Christopherson et al. |
| 2017/0135604 A1 | 5/2017 | Kent et al. |
| 2017/0135629 A1 | 5/2017 | Kent et al. |
| 2017/0143257 A1 | 5/2017 | Kent et al. |
| 2017/0143259 A1 | 5/2017 | Kent et al. |
| 2017/0143280 A1 | 5/2017 | Kent et al. |
| 2017/0143960 A1 | 5/2017 | Kent et al. |
| 2017/0143973 A1 | 5/2017 | Tehrani |
| 2017/0164871 A1 | 6/2017 | Ramanan |
| 2017/0164906 A1 | 6/2017 | Ramanan |
| 2017/0172459 A1 | 6/2017 | Bernstein et al. |
| 2017/0181663 A1 | 6/2017 | Hansen et al. |
| 2017/0182358 A1 | 6/2017 | Zavrel |
| 2017/0188940 A9 | 7/2017 | Goldstein |
| 2017/0204386 A1 | 7/2017 | Vitalis et al. |
| 2017/0209657 A1 | 7/2017 | Levings et al. |
| 2017/0224943 A1 | 8/2017 | Creusot et al. |
| 2017/0231504 A1 | 8/2017 | Heneghan et al. |
| 2017/0238812 A1 | 8/2017 | Atlas |
| 2017/0238867 A1 | 8/2017 | Javed et al. |
| 2017/0239433 A1 | 8/2017 | Martin et al. |
| 2017/0258365 A1 | 9/2017 | Ramanan et al. |
| 2017/0274165 A1 | 9/2017 | Ramanan et al. |
| 2017/0311879 A1 | 11/2017 | Armitstead et al. |
| 2017/0321914 A1 | 11/2017 | Miller |
| 2017/0326025 A1 | 11/2017 | Hernandez |
| 2017/0326316 A1 | 11/2017 | Rapoport et al. |
| 2017/0326320 A1 | 11/2017 | Baigent et al. |
| 2017/0347904 A1 | 12/2017 | Wilson |
| 2017/0347951 A1 | 12/2017 | Gollakota et al. |
| 2017/0361041 A1 | 12/2017 | Scheerer et al. |
| 2017/0361044 A1 | 12/2017 | Armitstead et al. |
| 2017/0361045 A1 | 12/2017 | Fu et al. |

(56) References Cited

U.S. PATENT DOCUMENTS

| | | |
|---|---|---|
| 2017/0361103 A1 | 12/2017 | Hadjiyski |
| 2017/0363096 A1 | 12/2017 | Fleming et al. |
| 2017/0367619 A1 | 12/2017 | Zhan |
| 2017/0368339 A1 | 12/2017 | De Ridder |
| 2018/0000427 A1 | 1/2018 | Wickham |
| 2018/0003723 A1 | 1/2018 | Rai et al. |
| 2018/0015282 A1 | 1/2018 | Waner et al. |
| 2018/0028770 A1 | 2/2018 | Parrish |
| 2018/0036533 A1 | 2/2018 | Yoo et al. |
| 2018/0043125 A1 | 2/2018 | Bencke et al. |
| 2018/0049678 A1 | 2/2018 | Hoskuldsson et al. |
| 2018/0064390 A1 | 3/2018 | Thakur et al. |
| 2018/0070890 A1 | 3/2018 | Bradley et al. |
| 2018/0071471 A1 | 3/2018 | Kirollos |
| 2018/0085246 A1 | 3/2018 | Loomas et al. |
| 2018/0103860 A1 | 4/2018 | Christopherson et al. |
| 2018/0103896 A1 | 4/2018 | Shin et al. |
| 2018/0106897 A1 | 4/2018 | Shouldice et al. |
| 2018/0116588 A1 | 5/2018 | Wang |
| 2018/0117270 A1 | 5/2018 | Bassin |
| 2018/0133430 A1 | 5/2018 | Orr |
| 2018/0140795 A1 | 5/2018 | Wells et al. |
| 2018/0153427 A1 | 6/2018 | Al-Jumaily et al. |
| 2018/0168502 A1 | 6/2018 | Cho et al. |
| 2018/0168852 A1 | 6/2018 | Sanders et al. |
| 2018/0169361 A1 | 6/2018 | Dennis et al. |
| 2018/0185599 A1 | 7/2018 | Wood |
| 2018/0200467 A1 | 7/2018 | Finch |
| 2018/0206762 A1 | 7/2018 | Huang |
| 2018/0228399 A1 | 8/2018 | Orr et al. |
| 2018/0236191 A1 | 8/2018 | Martin et al. |
| 2018/0236200 A1 | 8/2018 | Goldspink et al. |
| 2018/0242903 A1 | 8/2018 | Zhuang |
| 2018/0250486 A1 | 9/2018 | Amarasinghe et al. |
| 2018/0256069 A1 | 9/2018 | McMahon |
| 2018/0256096 A1 | 9/2018 | Galeev et al. |
| 2018/0256843 A1 | 9/2018 | Eves et al. |

OTHER PUBLICATIONS

U.S. Appl. No. 10/004,438, filed Jun. 26, 2018, Huang et al.
U.S. Appl. No. 10/004,862, filed Jun. 26, 2018, Armitstead et al.
U.S. Appl. No. 10/022,084, filed Jul. 17, 2018, Nonaka et al.
U.S. Appl. No. 10/029,058, filed Jul. 24, 2018, Foote et al.
U.S. Appl. No. 10/032,526, filed Jul. 24, 2018, Lynn et al.
U.S. Appl. No. 10/045,907, filed Aug. 14, 2018, Harper et al.
U.S. Appl. No. 10/046,127, filed Aug. 14, 2018, Berthon-Jones.
U.S. Appl. No. 10/047,964, filed Aug. 14, 2018, Miller.
U.S. Appl. No. 10/052,449, filed Aug. 21, 2018, Miller et al.
U.S. Appl. No. 10/058,269, filed Aug. 28, 2018, Lynn.
U.S. Appl. No. 10/058,272, filed Aug. 28, 2018, Heinrich et al.
U.S. Appl. No. 10/065,008, filed Sep. 4, 2018, Cullen et al.
PCT/US2017/061099 IPER.
PCT/US2017/061099 ISR.

* cited by examiner

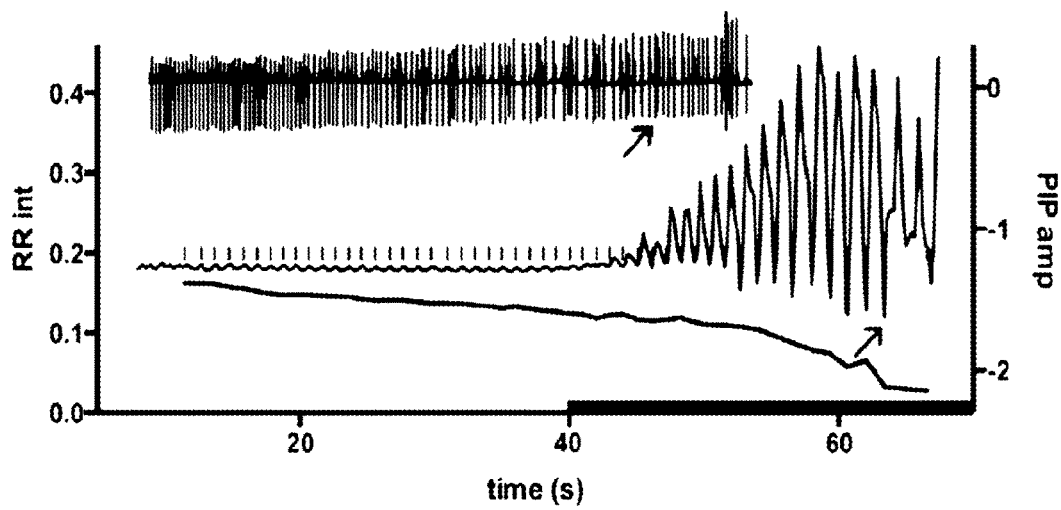
Fig. 1B
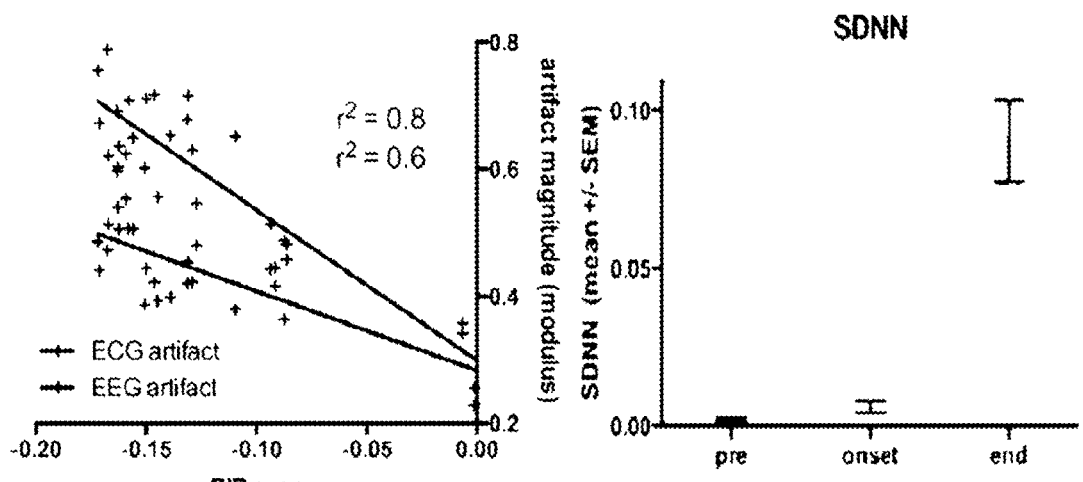
Fig. 1C
Fig. 1D
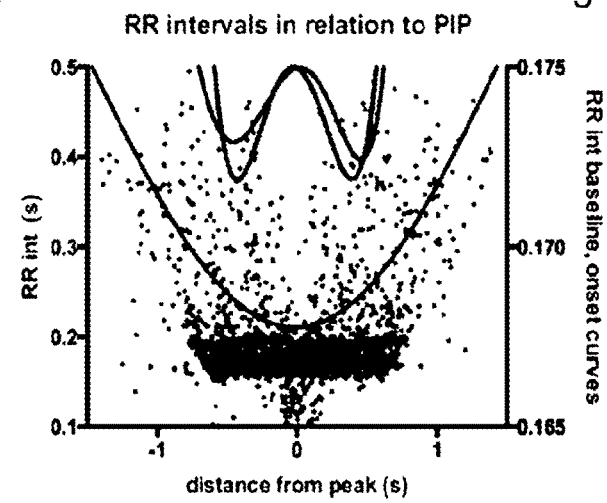
Fig. 1E

Plethysmograph volume vs. Time (min)
Non-intubated Baseline

Plethysmograph volume vs. Time (min)
Intubated Baseline

Flow (ml/sec) vs. Volme (ml)
Non-intubated Baseline

Flow (ml/sec) vs. Volme (ml)
Intubated Baseline

Plethysmograph volume vs. Time (min)
Non-intubated Seizure

Plethysmograph volume vs. Time (min)
Intubated Seizure

Flow (ml/sec) vs. Volme (ml)
Non-intubated Seizure

PF(i)/PF(e) = 1.11

Flow (ml/sec) vs. Volme (ml)
Intubated Seizure

PF(i)/PF(e) = 1.16

SYSTEM, METHOD AND BIOMARKERS FOR AIRWAY OBSTRUCTION

FIELD OF THE INVENTION

The present invention relates to the field of systems and methods for detecting obstructive apnea or dyspnea, and biomarkers for obstructive apnea or dyspnea.

BACKGROUND OF THE INVENTION

Airway obstruction can be a critical health emergency, leading to death within minutes. Partial obstruction is also possible.

Apnea is suspension of breathing. During apnea, the volume of the lungs initially remains unchanged. Depending on how blocked the airways are (patency), there may or may not be a flow of gas between the lungs and the environment; gas exchange within the lungs and cellular respiration is not acutely affected.

In obstructive apnea, breathing is attempted, which causes increased activation of the diaphragm and other muscles of respiration, including the intercostal muscles. After a few minutes of prolonged apnea, blood oxygen falls, and various secondary responses occur.

Epileptic seizure is associated with obstructive apnea. Seizure activity spreads to laryngeal motor neurons to cause laryngospasm. Laryngospasm results in partial or complete airway occlusion. Seizure activity changes breathing frequency, amplitude, variability, and can cause central apnea. Only obstructive apnea was associated with rapid, severe arterial oxygen desaturation, bradycardia, and death. Sudden death is the result of respiratory arrest during airway obstruction and nearly simultaneous LV dilatation and asystole. Sudden death in epilepsy can be the result of seizure induced laryngospasm sufficient to cause obstructive apnea, which leads to respiratory arrest and cardiac asystole within tens of seconds.

The recurrent laryngeal nerve (RLN) is a branch of the vagus nerve (cranial nerve X) that supplies all the intrinsic muscles of the larynx, with the exception of the cricothyroid muscles. These muscles act to open and close the vocal cords, and include the posterior cricoarytenoid muscles, the only muscle to open the vocal cords. The nerves supply muscles on the same side of the body, with the exception of the interarytenoid muscle, which is innervated from both sides. See, en.wikipedia.org/wiki/Recurrent_laryngeal_nerve. The recurrent laryngeal nerves supply sensation to the larynx below the vocal cords, gives cardiac branches to the deep cardiac plexus, and branches to the trachea, esophagus and the inferior constrictor muscles. The posterior cricoarytenoid muscles, the only muscles that can open the vocal cords, are innervated by this nerve. The nerves also carry sensory information from the mucous membranes of the larynx below the lower surface of the vocal fold, as well as sensory, secretory and motor fibers to the cervical segments of the esophagus and the trachea.

The MORTality in Epilepsy Monitoring Unit Study (MORTEMUS) identified a consistent sequence of events in epilepsy patients beginning with a generalized tonic clonic seizure and ending in death [Ryvlin et al., Lancet Neurol. 12:966, 2013]. Ten cases were used to establish that the end of the seizure was followed within minutes by terminal apnea and ultimately cardiac arrest. Most importantly, this study established a singular pattern for their SUDEP cases.

U.S. Pat. No. 5,800,470, expressly incorporated herein by reference, discloses a respiratory muscle electromyographic rate responsive implantable pacemaker. The directly detected electromyogram (EMG) signal is amplified and band passed filtered, processed to remove any electrocardiogram (ECG) or pacing impulse signal, full-wave rectified, processed to develop a moving time average signal from which the peak, the maximal slope, and the average slope of the EMG moving time average may be calculated and processed in conjunction with the inspiratory and expiratory times between successive slope detections of the moving time average EMG to develop a rate control signal representative of ventilation rate. The EMG may be selectively picked up from electrodes implanted in or near the parasternal intercostal muscles, the external intercostal muscles, the internal intercostal muscles, the diaphragm, or any other respiratory muscle such as the scalenes, or the sternocleidomastoid, and coupled to conventionally designed or special configuration pacemaker pulse generators and cardiac pace/sense lead systems.

U.S. Pat. No. 4,961,423, expressly incorporated herein by reference, proposes to employ specific electromyogram or EMG (a graph of electrical signals associated with muscle activity) signal processing circuitry in conjunction with a conventional cardiac pacing lead system to derive a control signal which reflects the patient's respiration as reflected across the electrodes in contact with the patient's heart. By use of specific filtration and signal processing, it is proposed to separate the EMG signal from the electrocardiogram (ECG) signal and pacing stimulation impulse from the aggregate signal picked up across the pacing tip and can electrode pair or across separate electrodes devoted to the detection of the EMG.

Getzel et al., "Variation of Cardiac Pacemaker Rate Relative to Respiration," IEEE Proceedings of 32nd CEMB, 1979, p. 123, and "Variation of Cardiac Pacemaker Rate Relative to Respiration," IEEE Trans. on Biomed. Eng., Vol. BME-26, No. 9, September 1979, p. 526., expressly incorporated orated herein by reference, describe the electronic integration of the diaphragm electromyogram to generate a control signal proportional to respiratory minute volume for use as the controlling physiological input for a pacemaker.

US 2016/0089540, expressly incorporated herein by reference, a method of treating a patient, comprising: sensing a biological parameter indicative of respiration; analyzing the biological parameter to identify a respiratory cycle; identifying an inspiratory phase of the respiratory cycle; and delivering stimulation to a hypoglossal nerve of the patient, wherein stimulation is delivered if a duration of the inspiratory phase of the respiratory cycle is greater than a predetermined portion of a duration of the entire respiratory cycle.

It is thus known that there is a respiration artifact in the ECG signal. It is also known that the intrinsic ECG signal is respiratory responsive, including R-R interval.

Nakase et al., "Laryngospasm, central and obstructive apnea during seizures: Defining pathophysiology for sudden death in a rat model, Epilepsy Research, Volume 128, 126-139 (December 2016), DOI:dx.doi.org/10.1016/j.eplepsyres.2016.08.004; www.epires-journal.com/article/S0920-1211(16)30124-3/abstract, describes the pathophysiology of sudden death in epilepsy using an animal model, and has several figures that illustrate laryngospasm, obstructive apnea, desaturation during obstructive apnea, direct measures of the forces developed during attempts to inspire against a closed airway, and evidence of artifacts in ECG records.

Seizure spread into the autonomic nervous system is thought to play an important role in sudden unexpected death in epilepsy (SUDEP; (Bermeo-Ovalle et al., 2015;

Devinsky, 2011; Lathers et al., 2008; Sakamoto et al., 2008; Shorvon and Tomson, 2011; Stewart, 2011; Surges and Sander, 2012; Tolstykh and Cavazos, 2013)). Approximately 1% of the US population lives with epilepsy; depending on how one defines sudden death, 2%-17% of deaths in these patients are labeled SUDEP (e.g. (Nei and Hays, 2010)). Among adults with epilepsy, mortality rates are 2-3 times greater than among their non-epileptic counterparts (Langan, 2000; Thurman et al., 2014), and SUDEP is the single most common cause of death (Lathers et al., 1998; Wannamaker, 1985).

Seizures are known to produce significant respiratory changes (reviewed in (Massey et al., 2014; Sowers et al., 2013)). Ictal apnea (Blum, 2009) is implicated in oxygen desaturation during seizures (Bateman et al., 2008; Seyal et al., 2010). Indeed, animal research established the importance of ictal hypoxemia in seizure-induced death, as studies in sheep have shown that ictal hypoventilation leads to severe bradycardia and death (Johnston et al., 1995; Johnston et al., 1997). Similar findings have been noted in rats (Sakamoto et al., 2008; Stewart, 2011), cats (Schraeder and Lathers, 1983), and mice (Faingold et al., 2010; Uteshev et al., 2010). The physiological mechanisms, however, that link seizures to respiratory dysfunction have not been fully resolved.

One possible cause of ictal respiratory distress is laryngospasm, a tonic adduction of the vocal folds that partially or fully obstructs the upper airway. Laryngospasm has been observed during seizures or postictally, evidenced by stridor and a narrowed airway when attempting to place an endotracheal tube (Tavee and Morris, 2008) or intensive inspiratory effort with severe air hunger (Amir et al., 1983). Cats and piglets experienced hypoventilation and glottal obstruction during chemically-induced seizures (Learning et al., 1999; Terndrup et al., 1995a; Terndrup et al., 1995b). That pulmonary edema is the most common single finding at autopsy in SUDEP cases is also indirect evidence of laryngospasm (Antoniuk et al., 2001; Morentin and Alcaraz, 2002; Salmo and Connolly, 2002). Pulmonary edema can occur when "pulling" against a closed airway—the inspiratory effort increases pulmonary capillary pressure (Ead, 2003; Murray-Calderon and Connolly, 1997; Umbrain and Camu, 1993). Seizures could cause ictal laryngospasms by spreading via autonomic medullary motor regions to the laryngeal branches of the vagus nerve, the efferent innervation of the vocal folds.

A urethane/kainate rat model (reviewed in (Naggar and Stewart, 2015; Stewart, 2011)) was used to permit detailed study of laryngospasm during seizure activity. This model allows invasive monitoring during seizure activity. Recordings are obtained from the recurrent laryngeal nerve, the principal motor output to the larynx (Bartlett, 2011; Brancatisano et al., 1991; Kuna et al., 1991; Kuna et al., 1988; Kuna et al., 1990), along with simultaneous laryngoscopy (Mor et al., 2014) to define the patterns of RLN activity during seizures, the impact of seizure activity on laryngeal function, and the impact of laryngeal dysfunction on breathing. These data highlight the complexity of laryngospasm during seizures, and how changes in laryngeal function can contribute to death.

In order to monitor heart signals in an ambulatory environment, a number of options are available. Bioelectric signals may be acquired from the chest wall, limbs, and digits. Heart rate and pulse variability can also be acquired using pulse information, which can be acquired by plethysmography and optical sensors on the skin, wrist, ankle, and digits.

See: www.vitalconnect.com/upload/Documents/EngeryExpenditure2014_MobiHealth_published.pdf; www.vitalconnect.com/upload/Documents/Longterm-Remote-Monitoring_HealthInnovations_2014_published.pdf; www.vitalconnect.com/upload/Documents/AutomatedPrediction_2014_IEEE_published.pdf; www.vitalconnect.com/upload/Documents/2014-Sleep-Abstract.pdf; www.vitalconnect.com/upload/press/Chan2013EMBC_VitalConnectPatch.pdf; www.vitalconnect.com/upload/press/Selvaraj2013EMBC_OSAeventDetectionRespiratorySignals pdf; www.vitalconnect.com/upload/press/Chan2013EMBC_RespirationECGandAccelerometer.pdf; Rosenberg M., Samuel M., Thosani A, Zimetbaum P., "Use of a noninvasive continuous monitoring device in the management of atrial fibrillation: a pilot study", Pacing Clin Electrophysiol. 2013; 36(3): 328-333.

See also, U.S. Patent and Pub. Patent App. Nos. 3942513; 3950799; 4033332; 4169462; 4197856; 4289142; 4350166; 4381788; 4387722; 4391279; 4403215; 4422458; 4446869; 4474185; 4475559; 4506626; 4558708; 4595016; 4630614; 4657026; 4686975; 4694839; 4715367; 4724844; 4732159; 4736749; 4745925; 4757824; 4757825; 4765340; 4802485; 4802486; 4803997; 4806112; 4838279; 4889116; 4895162; 4924860; 4928692; 4928703; 4958638; 4961423; 4982738; 5005234; 5005571; 5016636; 5036852; 5052400; 5095900; 5099836; 5107855; 5131387; 5133346; 5206807; 5271412; 5295490; 5307817; 5309921; 5311875; 5353793; 5360008; 5395301; 5485850; 5495242; 5603316; 5645053; 5671733; 5704345; 5765554; 5769084; 5779631; 5782240; 5792068; 5800360; 5800470; 5825293; 5853005; 5873821; 5879313; 5913826; 5928157; 5954053; 5961447; 5964720; 6017315; 6019732; 6029665; 6045514; 6062216; 6064910; 6134460; 6138675; 6150104; 6150941; 6168568; 6208897; 6223064; 6241683; 6248068; 6261238; 6267730; 6286508; 6290654; 6342039; 6342040; 6363933; 6368287; 6375621; 6390987; 6450168; 6454724; 6470888; 6477710; 6498652; 6510339; 6537228; 6544192; 6549795; 6550478; 6553242; 6553256; 6574507; 6580943; 6580944; 6621278; 6675797; 6721980; 6773404; 6785568; 6816266; 6849049; 6856141; 6881192; 6915705; 6920877; 6970737; 6984993; 6989744; 7020511; 7035432; 7039152; 7074177; 7080554; 7092755; 7117036; 7126467; 7129833; 7148797; 7166123; 7168429; 7170404; 7173525; 7179229; 7225021; 7269459; 7315760; 7320320; 7330127; 7340302; 7363086; 7391316; 7403110; 7415093; 7431700; 7435221; 7460899; 7467012; 7473227; 7477142; 7477143; 7477144; 7508307; 7515059; 7522035; 7533571; 7593764; 7597659; 7611472; 7656287; 7661426; 7667624; 7678058; 7711579; 7715905; 7716767; 7725181; 7730886; 7734335; 7794716; 7800505; 7811234; 7818058; 7827988; 7884735; 7894849; 7899521; 7909764; 7938114; 7942822; 7976470; 7988640; 8011365; 8031080; 8050765; 8106781; 8119134; 8121692; 8136521; 8142343; 8155735; 8161971; 8204580; 8219185; 8226570; 8226571; 8238996; 8255029; 8258973; 8262578; 8273053; 8301219; 8301232; 8360060; 8360983; 8381722; 8393233; 8396537; 8403861; 8417351; 8442578; 8449473; 8482418; 8483807; 8483811; 8483834; 8489182; 8509882; 8527028; 8538510; 8551010; 8554323; 8560044; 8562526; 8566115; 8568160; 8579792; 8595164; 8616203; 8630704; 8641631; 8683999; 8700137; 8718751; 8721554; 8721560; 8721573; 8731644; 8750987; 8752547; 8768731; 8790270; 8801620; 8828386; 8844525; 8862211; 8868152; 8880207; 8892194; 8923971; 8948854; 8954137; 8983587; 8985106; 9019100; 9022032; 9024781; 9026202; 9037477; 9044362; 9078577; 9089691; 9101277; 9113788; 9131892; 9132250; 9144389; 9177459; 9180270; 9192336; 9198616; 9198617; 9199053; 9202084; 9215075; 9216291;

9220459; 9220460; 9227034; 9269000; 9277867; 9302116; 9307921; 9333318; 9364180; 9370634; 9414787; 9415182; 9445736; 9445740; 9445747; 9451888; 9468835; 9477812; D284697; RE32180; 20010018557; 20010044588; 20020007126; 20020078957; 20020099300; 20020105340; 20020161290; 20020173707; 20030024528; 20030111079; 20030161436; 20030161440; 20030163059; 20030199945; 20030208130; 20030213488; 20030236548; 20040002742; 20040082874; 20040104733; 20040123866; 20040158193; 20040186523; 20040187870; 20040194220; 20040207409; 20040257233; 20050027204; 20050027206; 20050053262; 20050085736; 20050085863; 20050085865; 20050101833; 20050113656; 20050177051; 20050211248; 20050211249; 20050273361; 20050277842; 20050288572; 20060000475; 20060004245; 20060011200; 20060025696; 20060025697; 20060030894; 20060050930; 20060087325; 20060122675; 20060134106; 20060179571; 20060229489; 20060258916; 20060258921; 20060264770; 20070061393; 20070062540; 20070073177; 20070100381; 20070106536; 20070106537; 20070106750; 20070106751; 20070106752; 20070106753; 20070106754; 20070116036; 20070116037; 20070142713; 20070142741; 20070167694; 20070168461; 20070199262; 20070215146; 20070255310; 20070265539; 20070282212; 20080009755; 20080015454; 20080015457; 20080039730; 20080040151; 20080041382; 20080041383; 20080045832; 20080051845; 20080058873; 20080058892; 20080060138; 20080071185; 20080082016; 20080091082; 20080092898; 20080101532; 20080154110; 20080161708; 20080163873; 20080167567; 20080170654; 20080177789; 20080183095; 20080183239; 20080190430; 20080190436; 20080243021; 20080262360; 20080287769; 20080287770; 20080288013; 20080300499; 20080308112; 20080313816; 20080319513; 20090036790; 20090099462; 20090099469; 20090118629; 20090149778; 20090172773; 20090177050; 20090177495; 20090183312; 20090203972; 20090226861; 20090226862; 20090226863; 20090226864; 20090226865; 20090270773; 20090318820; 20090326981; 20100004549; 20100010359; 20100016783; 20100018530; 20100036209; 20100036263; 20100036268; 20100036269; 20100056850; 20100063438; 20100099963; 20100137723; 20100159426; 20100168578; 20100179396; 20100198083; 20100198289; 20100204550; 20100222685; 20100222689; 20100228120; 20100242965; 20100252037; 20100252039; 20100252040; 20100252041; 20100252042; 20100253505; 20100258123; 20100262035; 20100268093; 20100297129; 20100307500; 20100328075; 20110009722; 20110011402; 20110021970; 20110034820; 20110105921; 20110131057; 20110160601; 20110172552; 20110184298; 20110184304; 20110190651; 20110214676; 20110245706; 20110284003; 20110301435; 20110301439; 20110319777; 20120004749; 20120028504; 20120029362; 20120032778; 20120046709; 20120056746; 20120088998; 20120101690; 20120109027; 20120130204; 20120130446; 20120136231; 20120152252; 20120160243; 20120165711; 20120172689; 20120173470; 20120189632; 20120197144; 20120203491; 20120209096; 20120232398; 20120232416; 20120240934; 20120252709; 20120272429; 20120283527; 20120323104; 20120330123; 20130012827; 20130030711; 20130046151; 20130046156; 20130046157; 20130046160; 20130046161; 20130046184; 20130046185; 20130046186; 20130046187; 20130046188; 20130053674; 20130060480; 20130081479; 20130085688; 20130096447; 20130096450; 20130123654; 20130131522; 20130165809; 20130174847; 20130178719; 20130211210; 20130218030; 20130234535; 20130255683; 20130261485; 20130268030; 20130281815; 20130291060; 20130296660; 20130300575; 20130307685; 20130312752; 20130312757; 20130331663; 20130340500; 20140012145; 20140018779; 20140025141; 20140031705; 20140031709; 20140058274; 20140066741; 20140066798; 20140073969; 20140094669; 20140100628; 20140107501; 20140150793; 20140152467; 20140163343; 20140163386; 20140171783; 20140180148; 20140180154; 20140218210; 20140221859; 20140228651; 20140243934; 20140246024; 20140246025; 20140258743; 20140276287; 20140309568; 20140309943; 20140320309; 20140323946; 20140330155; 20140330540; 20140363740; 20140364706; 20150005646; 20150018660; 20150035643; 20150038867; 20150039110; 20150065891; 20150073285; 20150101609; 20150112202; 20150119739; 20150126847; 20150141766; 20150141862; 20150150500; 20150173672; 20150182132; 20150182842; 20150216448; 20150228176; 20150251016; 20150257653; 20150305634; 20150314098; 20150320588; 20150321022; 20150359964; 20150366511; 20150370320; 20150374328; 20160004820; 20160022145; 20160022204; 20160030689; 20160045134; 20160045166; 20160045167; 20160045654; 20160045695; 20160066805; 20160066809; 20160074606; 20160089540; 20160095997; 20160100798; 20160120430; 20160120431; 20160120433; 20160120434; 20160128209; 20160135706; 20160143594; 20160169930; 20160174857; 20160220197; 20160228024; 20160228060; 20160256063; 20160256644; 20160263393; 20160278658; 20160296124; 20160302726; and 20160310103.

A fingertip electrometer-based cardiac cycle sensors is disclosed in US 2012/0004523.

SUMMARY OF THE INVENTION

Seizures are known to produce significant respiratory changes and seizure spread into the autonomic nervous system can result in life-threatening cardiovascular and respiratory dysfunction. Ictal apnea and/or ictal bradycardia has been well recognized as a part of the autonomic manifestation in epileptic seizures. Prolonged peri-ictal apnea and bradycardia are both regarded as risk factors for sudden death in epilepsy (SUDEP). SUDEP is the major cause of death among persons with epilepsy. However, the physiological mechanisms of SUDEP are poorly understood and no specific indicator of SUDEP events is known. One possible cause of ictal respiratory distress is laryngospasm, a tonic adduction of the vocal folds that partially or fully obstructs the upper airway. Using a rat model, sudden death due to seizure and hypoxemia-induced conditions was studied. Based on findings of the inventors, some seizures cause laryngospasm that is sufficiently severe to produce complete airway obstruction. Once occluded, attempts to inspire against a closed airway get progressively stronger until attempts stop (the point of respiratory arrest). These attempts produce clear artifacts in recordings of electrocardiogram (ECG) and electroencephalogram (EEG) signals whose amplitudes highly correlate with the force of attempted inspiration. Late in the occlusion, the RR interval variability is dramatically increased due to an overall slower heart rate in combination with additional very short RR intervals closely associated with attempts to inspire.

Artifacts in the ECG and EEG during obstructive apnea caused by laryngospasm correspond in time and correlate in size with a direct measure of inspiratory effort in experimental animals. Likewise, these inspiration efforts cause strong electromyography (EMG) signals from muscles of respiration, including diaphragm and intercostal muscles while the resulting hypoxemia leads to bradycardia and an abrupt increase in heart rate variability with very short RR intervals at the time of each attempted inspiration.

R waves in ECG can be automatically identified through RR interval analyses and artifact detection and quantification from ECG and EEG records.

These physiological effects detected by these signals and analyzed can be used as practical biomarkers of obstructive apnea (e.g. laryngospasm). Two particular biomarkers that are specific for upper airway occlusion include:
- a high frequency EMG signal superimposed on the ECG signal
- a variation in R-R wave intervals The high frequency signal has an amplitude that corresponds to inspiratory effort, and therefore by monitoring respiration artifacts over time, an adaptive baseline may be established. When an obstructive apnea occurs, the respiratory artifacts are altered in a distinctive way. The amplitude increases on successive attempts, and the timing of these attempts differs from a normal respiratory rate. Both the high frequency signal and the variation in R-R wave intervals are responsive to obstructive apnea and indicative of an apnea activity pattern of muscles of respiration, including diaphragm and intercostal muscles.

Because these biomarkers do not require ECG analysis per se, they may be detected from electrodes in non-standard locations for cardiac monitoring, such as fingers or wrist. As such, the monitoring device may take the form of a wristband, ring(s), or other convenient form. Of course, traditional chest electrodes may also be employed.

The R-R interval is the basic heart rate, and therefore the rate and its variability can be determined in an alternate manner, e.g., without electrocardiographic electrodes. For example, physical or optical pulse sensors, acoustic sensors, ballistocardiographic sensors, etc.

On the other hand, the high frequency electromyographic signal from muscles of respiration, including diaphragm and intercostal muscles, superimposed on the electrocardiographic signal would generally require an electronic sensor for detection. However, other types of respiratory sensors and detection may be employed, though when directly measuring respiration, the need for a biomarker or indirect measurement for apnea is diminished.

The combination of these biomarkers clearly indicates when a person's breathing is obstructed, attempting to breathe, and generating large breathing forces in these attempts. An alarm sounded at this point to alert a caretaker will permit enough time to ensure that respiratory arrest does not occur or that, if respiratory arrest does occur, resuscitation steps can be taken to save a life. These biomarkers can also be applied to past cases and used to monitor patients to improve outcomes.

These biomarkers may have application in various types of obstructive apnea. While a preferred system and method target ictal obstructive apneas, asthmatic conditions may produce similar biomarkers. Thus, when an asthmatic attack occurs, airways are restricted, leading to reduced chest pressure and large inspiratory efforts. Asthmatic apnea tends to be an incomplete blockage, and therefore the pattern over time may differ from a laryngospasm-induced apnea, but the biomarkers are sufficiently broad to permit application in various uses.

In the case of asthma, one might seek to determine the extent of blockage, which is not always directly apparent, especially in exercise induced-asthma, where increased demand is superimposed on the airway restriction. However, the restriction will increase the efforts required, and increase the pressure differentials, and thus the asthmatic restriction may be distinguished from the mere increased respiratory rate due to exertion.

Based on these biomarkers, a system and method is provided that can detect the period of obstructive apnea and be used to sound an alarm in time to prevent respiratory arrest or in time to permit resuscitation.

A particular aspect of the system and method is the extraction of one or both of the biomarkers from ECG data, EEG data, or other bioelectric signals. The data used for biomarker extraction can thus come from multiple sources. In circumstances where ECG data or EEG data is already collected and available for analysis, e.g. any continuous ECG recording or EEG recording in a hospital setting, such as that used in Critical Care Units, Epilepsy Monitoring Units, etc., the biomarker identification algorithms can be added to the existing instrumentation. In an ambulatory or home setting, ECG can be obtained by a minimally intrusive "bracelet" such as those used for popular HR monitoring, with the exception that a telemetry component would generally be added to the bracelet and the receiving station, e.g., smartphone, would house the biomarker detection software and the hardware used for the alarm. A hat or scalp monitor with electrodes can also provide EEG data.

Of course, the data analysis can be provided within the sensor module, and an audible and/or visual alarm sounded from the module. Sensing obstruction may incur a latency, of approximately 10-30 seconds, and the time before permanent damage occurs to the patient is only a few minutes, providing only a small window of opportunity to prevent a complete laryngeal obstruction of the patients airway, and therefore a local caregiver would need to provide immediate assistance, and remote monitoring would likely be ineffective. However, within a hospital or other facility, a remote, wireless alarm may be useful. Similarly, in cases of incomplete obstruction, such as bronchial constriction, the onset and resolution of the apnea provide a larger window of opportunity for intervention.

Biomarker extraction involves taking the ECG signal and processing it in different ways for each of the two biomarkers.

Biomarker 1

The algorithm for biomarker 1 (Artifact Growth) involves the following steps applied to ECG recorded with a bandwidth of approximately 10 Hz to >1 kHz:
1. Secondary filter applied to data to pass approximately 300 Hz to 1 kHz.
2. Detect and measure breathing artifacts by methods such as rectification and integration or signal "envelope" quantification.
3. Compare values to amplitude threshold.
4. Hold value and time of events above threshold.
5. Compare interval between successive events with window established for respiratory rate.
6. Sound alarm if:
   a) 3 successive events are above threshold, and
   b) the interval between events is appropriate for respiratory rate, and
   c) the event amplitude is steady or increasing.

More generally, a bioelectric signal is obtained which includes a contribution from activity of muscles of respiration, including diaphragm and intercostal muscles activity. The bioelectric signal is processed to represent amplitude and timing of inspiratory efforts. The respiratory rate is compared with a normal pre-detection rate, and the amplitude of the bioelectric signal is compared with a pre-detection normal amplitude. The obstructive apnea is likely present if a series of inspiratory efforts are above a normal amplitude and with increasing amplitude, but at a normal rate.

Biomarker 2

The algorithm for biomarker 2 (Ultrashort RR Intervals) involves analysis of the acquired ECG signal with the following steps:

1. Detect R waves.
2. Measure RR intervals.
3. Compare interval to baseline range.
4. If ultrashort interval detected (RR interval is below threshold), store value and time of event.
5. Immediately successive short intervals are stored as a single event.
6. Compare time between successive events to the window established for respiratory rate.
7. Sound alarm if:
   a) 3 sets of short intervals are spaced by the respiratory interval.

More generally, the heart rate is determined, and compared to a baseline average. A normal lower threshold is established, and if subthreshold events occur (short RR intervals), a commencement of each sequence of subthreshold events is compared for a respiratory rate-normalized window. If the number of subthreshold events exceeds a minimum for the window, obstructive apnea is likely present.

The technology may be implemented in any device that receives a bioelectric signal that includes electromygraphic signals emanating from muscles of respiration. For example, an automated external defribrillator (AED) device may be provided with program instructions that permit the ECG electrodes to read the electromygraphic signals, and provide obstructive apnea indication, in addition to the normal defribrillator functionality. As noted, the present system seeks to compare a current bioelectric signal with a baseline signal, which may not be available in an acute emergency. Likewise, the AED tends to be employed with a human user in attendance, who can observe the patient. However, the user may be untrained, and therefore automatically monitoring the patient for apnea, and to distinguish different types of apnea, may be useful, especially for differential diagnosis where a patient hooked to the AED has a normal sinus rhythm, and yet is in distress.

It is therefore an object to provide a method for detecting obstructive apnea, comprising: receiving a bioelectric signal from a mammal comprising electromyographic activity of muscles of respiration, including diaphragm and intercostal muscles; processing the bioelectric signal to isolate the electromyographic activity; determining a timing and amplitude of inspiratory efforts based on the isolated electromyographic activity; determining a baseline amplitude of inspiratory efforts; comparing an amplitude of inspiratory efforts with the determined baseline amplitude of inspiratory efforts; and determining occurrence of obstructive apnea if a series of inspiratory efforts have increasing amplitude over time, above the baseline amplitude.

The method may further comprise determining a baseline timing of inspiratory efforts, and comparing the timing of inspiratory efforts with the determined baseline timing of inspiratory efforts, wherein the occurrence of obstructive apnea is determined if a series of inspiratory efforts have increasing amplitude above the baseline amplitude over time, and a baseline timing.

The timing and amplitude of inspiratory efforts may be determined over a series of three inspiratory efforts before the occurrence of obstructive apnea is determined.

The bioelectric signal may be an electrocardiographic signal. The bioelectric signal may be an electroencephalographic signal. The bioelectric signal may be acquired from a single extremity.

The method may further comprise generating an audible alarm in response to determining the occurrence of obstructive apnea. The method may further comprise generating a wireless communication in response to determining the occurrence of obstructive apnea.

The bioelectric signal may be received from a mammal comprising electromyographic activity of muscles of respiration, including diaphragm and intercostal muscles comprises receiving at least one of an electrocardiographic signal, an electroencephalographic signal, and an electromyographic signal. The processing of the bioelectric signal may be used to isolate electromyographic activity comprises subjecting the bioelectric signal to a bandpass filter having a passband between about 300 Hz and 1 kHz. The processing of the bioelectric signal may be used to isolate electromyographic activity comprises determining a signal power within a passband over time.

The comparing of an amplitude of inspiratory efforts with the determined baseline amplitude of inspiratory efforts may comprise comparing a series of amplitudes and timings of inspiratory efforts with a baseline window representing a normal range of amplitudes and timings of inspiratory efforts.

The occurrence of obstructive apnea may be determined if a series of inspiratory efforts have increasing amplitude over time, above the baseline amplitude, comprises determining if three successive inspiratory efforts have an amplitude above a threshold with at least one of a steady amplitude and an increasing amplitude, while an interval between inspiratory efforts is within a normal range.

It is also an object to provide a method of determining obstructive apnea, comprising: determining a baseline inter-heartbeat interval and a normal range of variation for a respective respiratory rate within a respiratory interval; determining an inter-heartbeat interval and a respiratory rate of a patient; determining a commencement of a series of inter-heartbeat intervals which is outside the normal range of variation below the baseline inter-heartbeat interval for the respective respiratory rate; and determining commencement of obstructive apnea if a number of commencements of the series of at least one inter-heartbeat interval which is below the baseline inter-heartbeat interval for the respective respiratory rate within the respiratory interval is above a threshold. The threshold may be three.

The inter-heartbeat interval and the respiratory rate may be determined based on a bioelectric signal.

The bioelectric signal may be an electrocardiographic signal, an electroencephalographic signal, and/or an electromyographic signal. The bioelectric signal may be acquired from a single extremity.

The method may further comprise generating an audible alarm in response to determining the commencement of obstructive apnea. The method may further comprise generating a wireless communication in response to determining the commencement of obstructive apnea. The method may further comprise automatically generating an e911 (enhanced 911) call through a telephone network in response to determining the commencement of obstructive apnea. The inter-heartbeat interval may be determined by determining an R-R interval of an electrocardiogram.

The method may further comprise establishing a window distinguishing a normal inter-heartbeat interval from a short inter-heartbeat interval for the respective respiratory rate;

and recording a time of an inter-heartbeat interval which is outside the window for the respective respiratory rate.

It is a further object to provide a system for detecting obstructive apnea, comprising: an input configured to receive a bioelectric signal from a mammal comprising electromyographic activity of muscles of respiration, including diaphragm and intercostal muscles; at least one processor configured to: process the bioelectric signal to isolate electromyographic activity; determine a timing and amplitude of inspiratory efforts based on the isolated electromyographic activity; determine a baseline amplitude of inspiratory efforts; compare an amplitude of inspiratory efforts with the determined baseline amplitude of inspiratory efforts; and determine occurrence of obstructive apnea if a series of inspiratory efforts have increasing amplitude over time, above the baseline amplitude; and an output for communicating an alarm dependent on the determined occurrence.

It is another object to provide a system for of determining obstructive apnea, comprising: an input configured to receive information defining am inter-heartbeat interval; at least one processor configured to: determine a baseline inter-heartbeat interval and a normal range of variation for a respective respiratory rate within a respiratory interval; determine an inter-heartbeat interval and a respiratory rate of a patient; determine a commencement of a series of inter-heartbeat intervals which is outside the normal range of variation below the baseline inter-heartbeat interval for the respective respiratory rate; and determine commencement of obstructive apnea if a number of commencements of the series of at least one inter-heartbeat interval which is below the baseline inter-heartbeat interval for the respective respiratory rate within the respiratory interval is above a threshold; and an output for communicating an alarm dependent on the determined commencement.

These and other objects will become apparent through a review of the description hereof.

BRIEF DESCRIPTION OF THE FIGURES

FIG. 1B shows correlations of ECG and EEG artifacts with peak inspiratory pressure (PIP).

FIG. 1C shows a plot of RR over time (bottom), PIP during obstruction (middle) and PIP peak markers (top). RR variance increases late in the occlusion.

FIG. 1D shows the standard deviation of the RR intervals (n=16 animals).

FIG. 1E shows plots of RR intervals as function of the time relative to the PIP (n=16 animals).

DETAILED DESCRIPTION OF THE PREFERRED EMBODIMENTS

Example 1

Figure 1A:
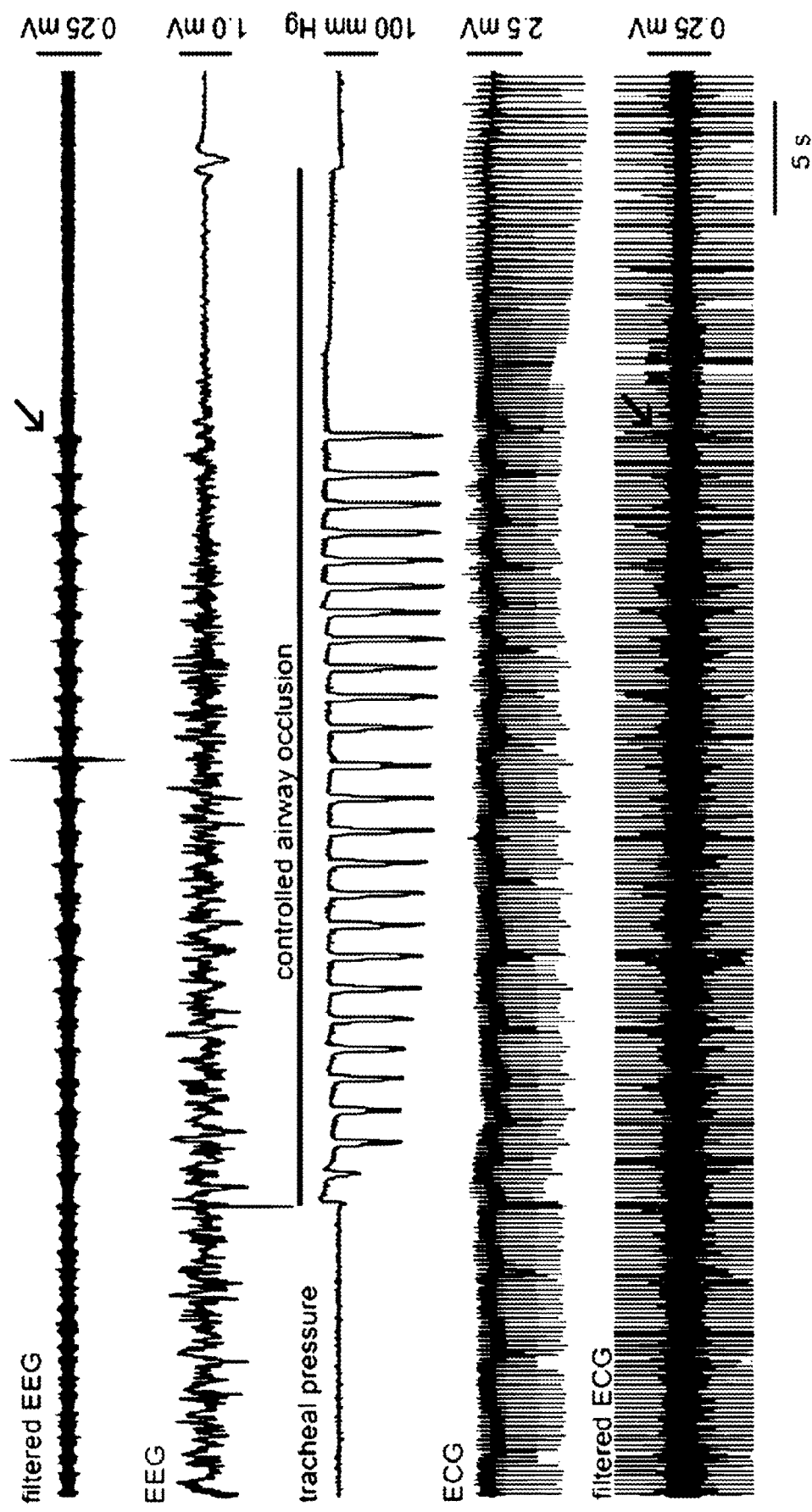
FIG. 1A shows artifacts enhanced in EEG and ECG by highpass filtering. Arrows indicate last breath attempt.

Parenteral kainic acid was used to induce recurring seizures in urethane-anesthetized Sprague Dawley rats. EEG recordings and combinations of cardiopulmonary monitoring, including video laryngoscopy, were performed during multi-unit recordings of recurrent laryngeal nerve (RLN) activity or head-out plethysmography with or without endotracheal intubation. Controlled occlusions of a tracheal tube were used to study the kinetics of cardiac and respiratory changes after sudden obstruction. Seizure activity caused significant firing increases in the RLN that were associated with abnormal, high-frequency movements of the vocal folds. Partial airway obstruction from laryngospasm was evident in plethysmograms and was prevented by intubation. Complete glottic closure (confirmed by laryngoscopy) occurred in a subset of non-intubated animals in association with the largest increases in RLN activity, and cessation of airflow was followed in all obstructed animals within tens of seconds by ST-segment elevation, bradycardia, and death.

Periods of central apnea occurred in both intubated and non-intubated rats during seizures for periods up to 33 seconds and were associated with modestly increased RLN activity, minimal cardiac derangements, and an open airway on laryngoscopy.

For controlled airway occlusion, a T-tube was inserted into the distal trachea of urethane-anesthetized rats. EEG, ECG, and inspiratory pressure at the sidearm of the T-tube were bandpass-filtered from 1 Hz to 1 kHz. The open port of the T-tube was occluded for 100 seconds or until respiratory arrest. Inspiration artifacts in the EEG and EEG records were isolated with a digital high-pass filter (corner frequency 367 Hz, rolloff −3 dB/octave) and quantified by full-wave rectification. Inspiration artifacts matched the inspiratory pressure extrema during airway occlusion. Correlations (r) of peak inspiratory pressure to artifact amplitude in a within-animal comparison were −0.88 (ECG) and −0.75 (EEG), suggesting that artifacts extracted from ECG records may be better than those derived from EEG records. The average correlation of artifact magnitude (ECG) with peak inspiratory pressure was −0.89±0.04 (N=5 rats). The results suggest that a sudden increase in the amplitude of the inspiratory artifact in EEG and ECG recordings indicates an occluded airway, and a very high correlation of increasing inspiration artifact size with increasing inspiratory effort was observed. This artifact pattern could serve as a biomarker in two important ways: First, to review existing records for the possible contribution of obstructive apnea to documented SUDEP cases. Second, to warn about obstructive apnea in patients being monitored in real time. The specificity of the biomarker would be further enhanced by marking decreases in seizure activity and heart rate. To maximize the sensitivity of the biomarker, EEG and ECG should be recorded at the highest bandwidth possible (within the capability of the available equipment, e.g., up to 10 kHz bandwidth). The most attractive feature of this biomarker is that it can be derived from commonly-used measures in epilepsy-monitoring units and even potentially portable devices outside of the hospital.

Using a rat model that permits simultaneous autonomic, cardiovascular, and respiratory monitoring, it was demonstrated that seizure-induced laryngospasm caused obstructive apnea, which stopped the seizure and persisted until respiratory arrest, followed by cardiac arrest. The MORTEMUS study used artifacts in EEG recordings as evidence of respiration. A critical finding herein is that attempts to breathe during obstruction generated artifacts in EEG and ECG recordings that resembled artifacts associated with actual breaths.

The electrical artifacts of attempts to inspire during airway obstruction can be used as a practical biomarker of obstructive apnea. In FIG. 1A, artifacts related to respiration in ECG and EEG recordings are shown in conjunction with tracheal pressure. Highpass filtered artifact size was highly correlated with peak inspiratory pressure ($r^2$=0.85; n=14 animals). The size of the artifact itself cannot discriminate between effective breaths and attempts to breathe. The specific biomarker is the upward trend in artifact size as a marker for increasing effort during airway obstruction.

Bradyarrhythmia is present in most patients [Ryvlin et al.] and animals. [Nakase et al.; Hotta et al. Epilepsia 50: 923, 2009]. An abrupt change in the ECG RR interval variability (SDNN; ECG and filtered ECG) and that the normal lengthening of the RR interval during inspiration could be reversed during the late occlusion period. This pattern represents a second biomarker for airway obstruction, even with short time samples. Abnormally short RR intervals associated with inspiration occurred in no animals at baseline, 4/16 animals during early occlusion, and 15/16 during late occlusion.

FIGS. 1A-1E show a demonstration of inspiration associated artifacts and changes in RR interval length during obstruction as biomarkers for obstructive apnea.

FIG. 1A shows artifacts enhanced in EEG and ECG by highpass filtering. Arrows indicate last breath attempt.

FIG. 1B shows correlations of ECG and EEG artifacts with peak inspiratory pressure (PIP).

FIG. 1C shows a plot of RR over time (black), PIP during obstruction (blue) and PIP peak markers (red). RR variance increases late in the occlusion. Relative minima in RR intervals are ONLY shorter than baseline during extreme inspiratory effort. Arrows point to the artifact or RR plot minimum for the breath just before a missed breath. Heavy black line at the bottom of the graph is the time shown in the inset.

FIG. 1D shows the standard deviation of the RR intervals (n=16 animals).

FIG. 1E shows plots of RR intervals as function of the time relative to the PIP (n=16 animals). Fitted curves for baseline and onset use right ordinate. Note the reverse relation of RR to inspiratory peak.

Example 2

The spread of seizure activity over the principal motor nerve of the larynx, RLN, was studied in one set of experiments aimed at characterizing RLN activity during normal quiet breathing (baseline) and during seizure activity induced by kainic acid. A tracheal opening or T-shaped tracheal tube that preserved RLN bilaterally was used to protect animals from laryngospasm. In animals with a tracheal tube, periods of complete glottic closure could be studied with laryngoscopy without concern about oxygen desaturation. RLN recordings were also made during other experiments with the goal of capturing RLN activity during specific events such as periods of central and obstructive apnea. EEG, multi-unit RLN activity, and ECG were recorded in all animals. Laryngoscopy was performed at intervals during experiments.

The impact of laryngospasm and seizure activity on ventilation was assessed with head-out plethysmography in a second set of experiments. One group of animals was intubated with an endotracheal tube prior to seizure induction and these animals were compared with non-intubated animals. The non-intubated animals comprised two subgroups: one with no treatment other than kainic acid to induce seizures, and a second with bilateral superior laryngeal nerve transection to prevent reflex laryngospasm performed in the pre-seizure condition.

Figure 2:
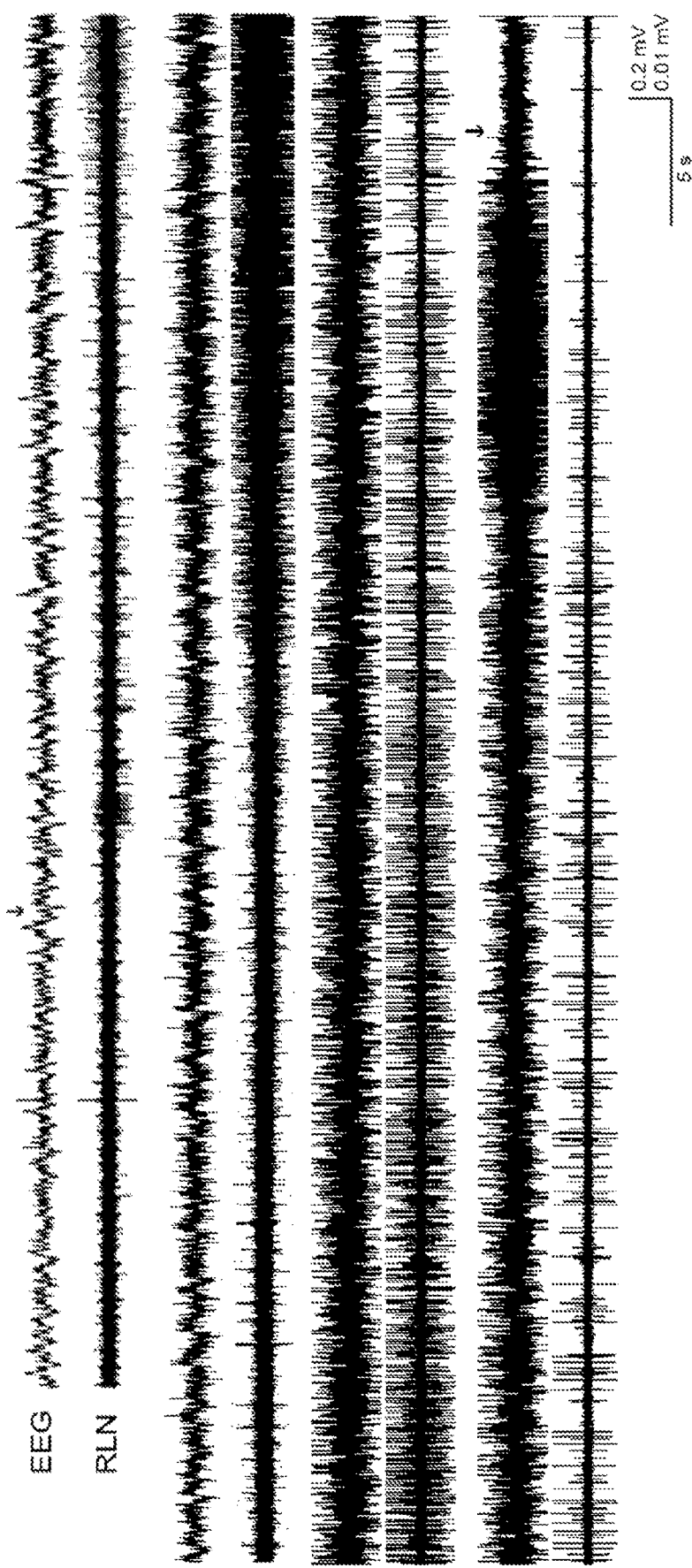
FIG. 2 shows extreme increases in RLN activity during a seizure.
Figure 3A:
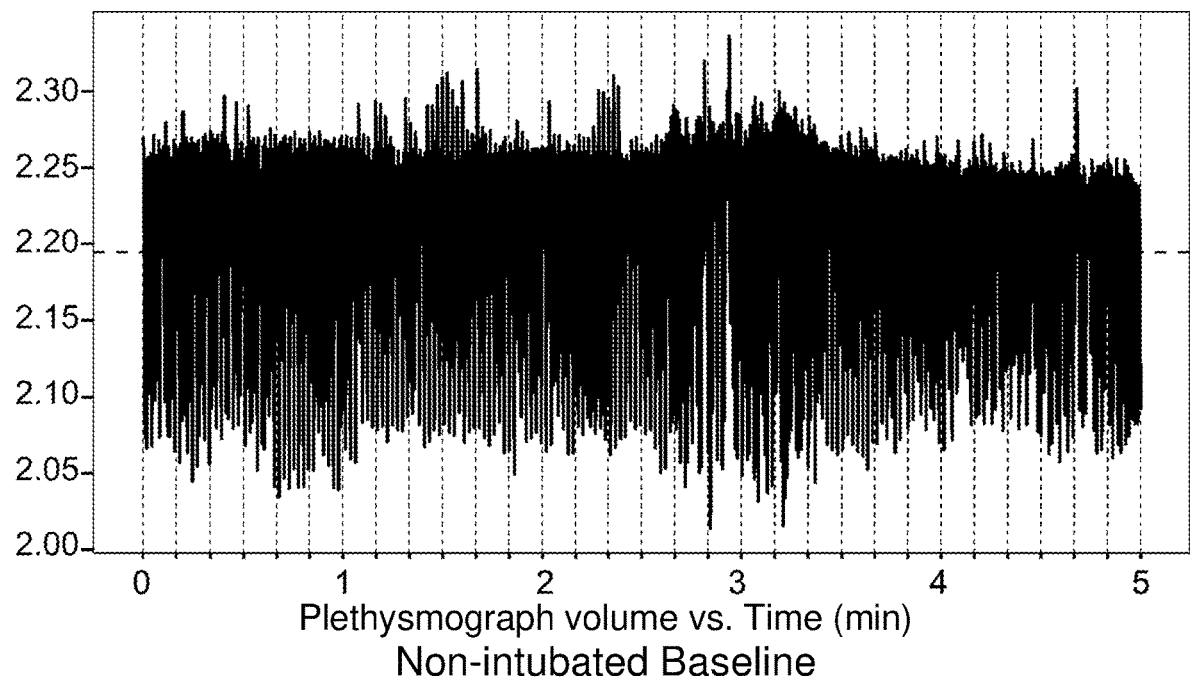
FIGS. 3A-3H show plethysmography during kainic acid-induced seizure activity.
Figure 3B:
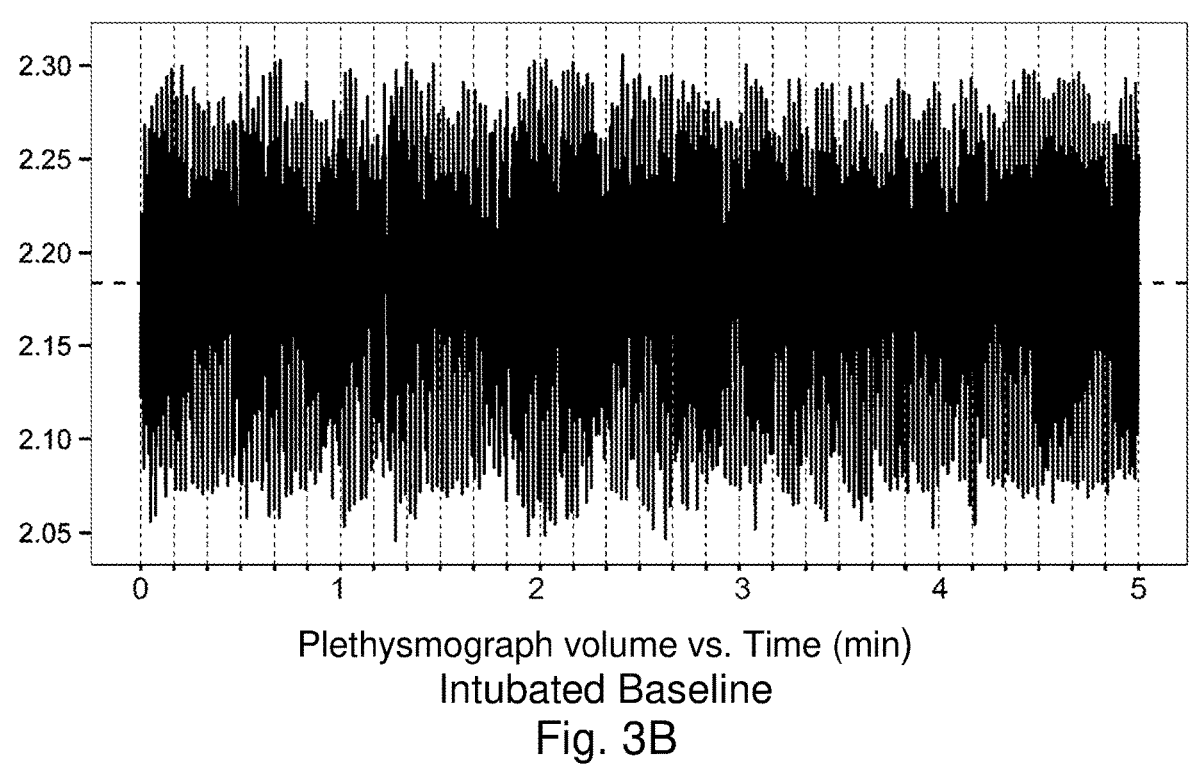
Figure 3C:
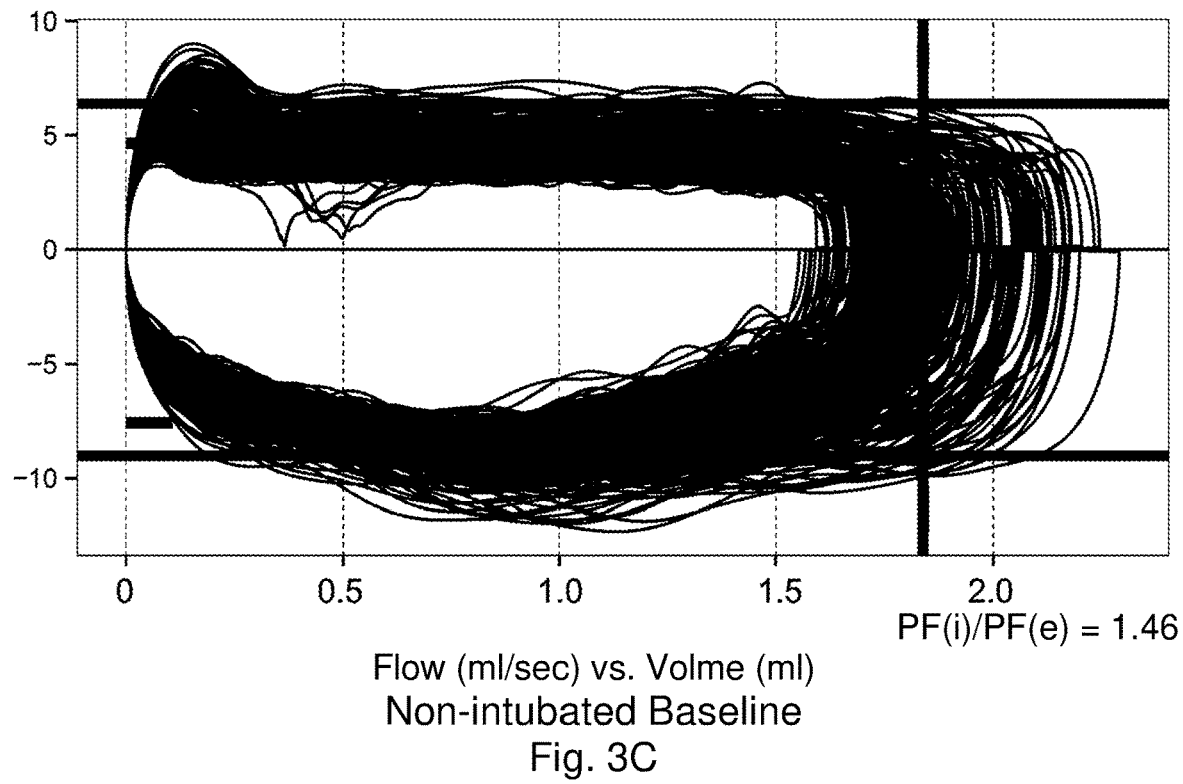
Figure 3D:
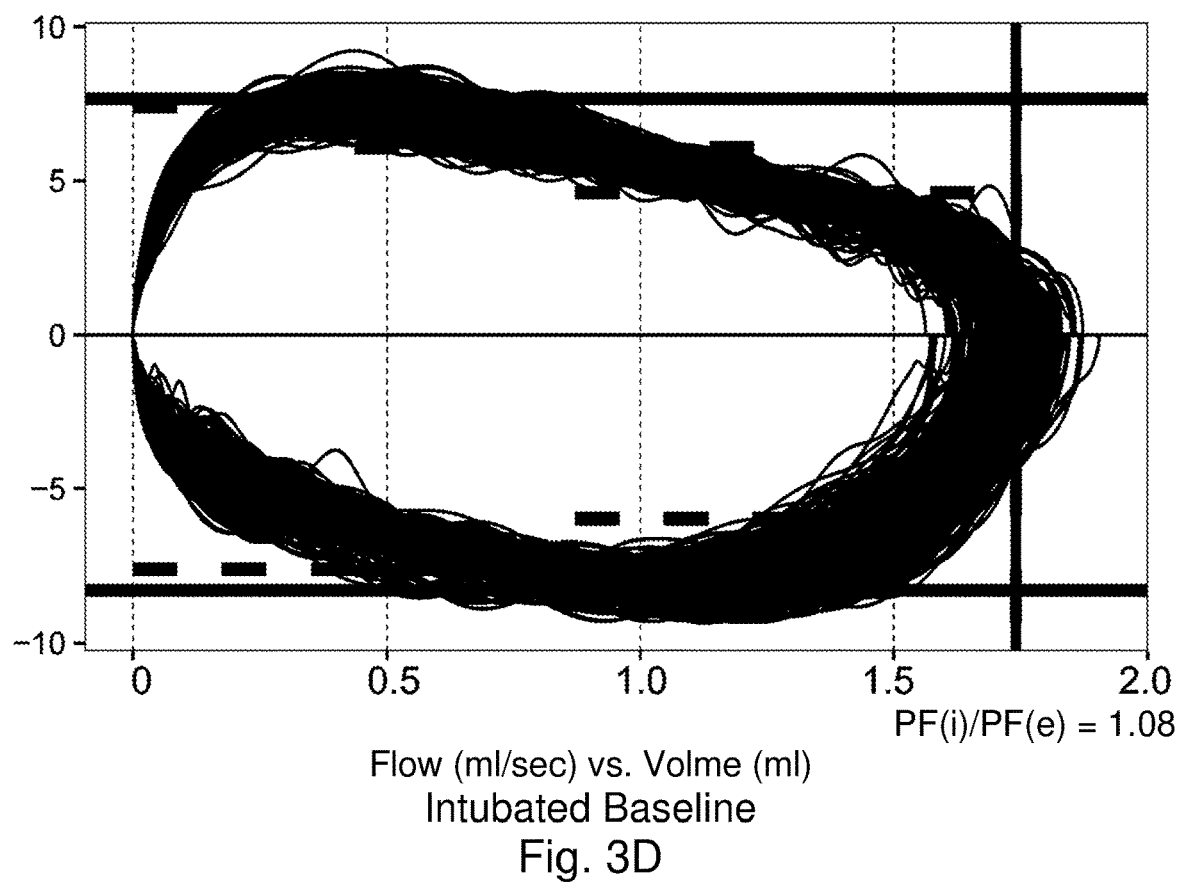
Figure 3E:
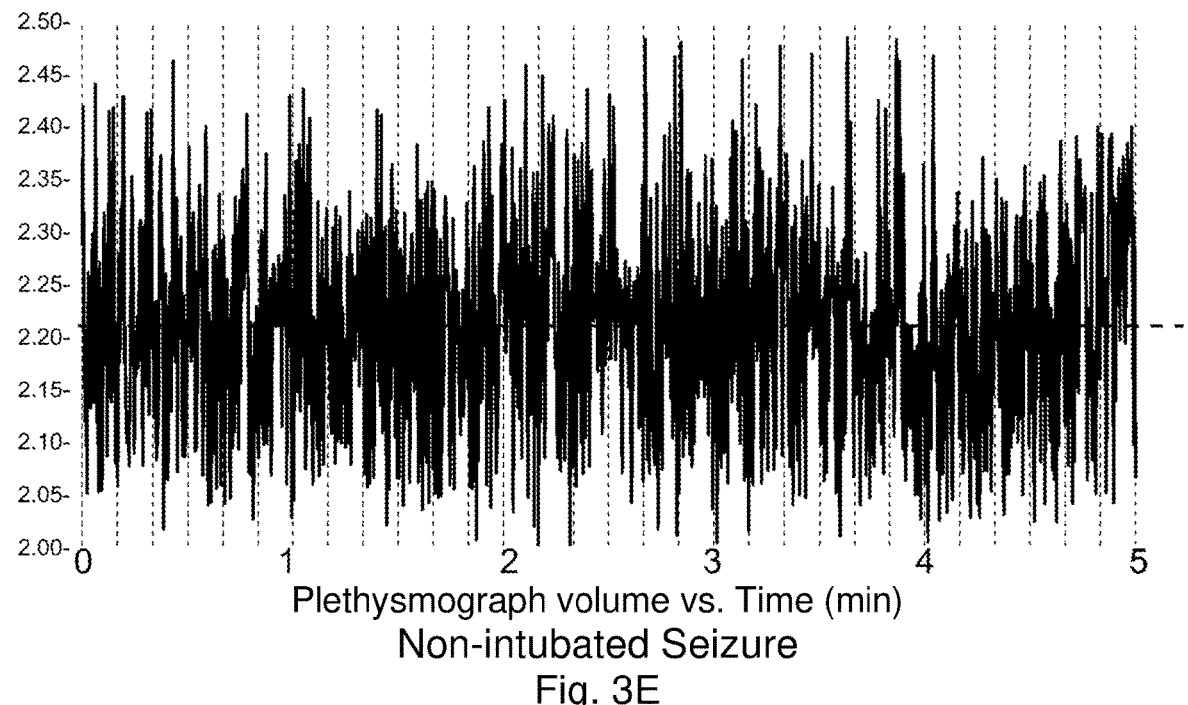
Figure 3F:
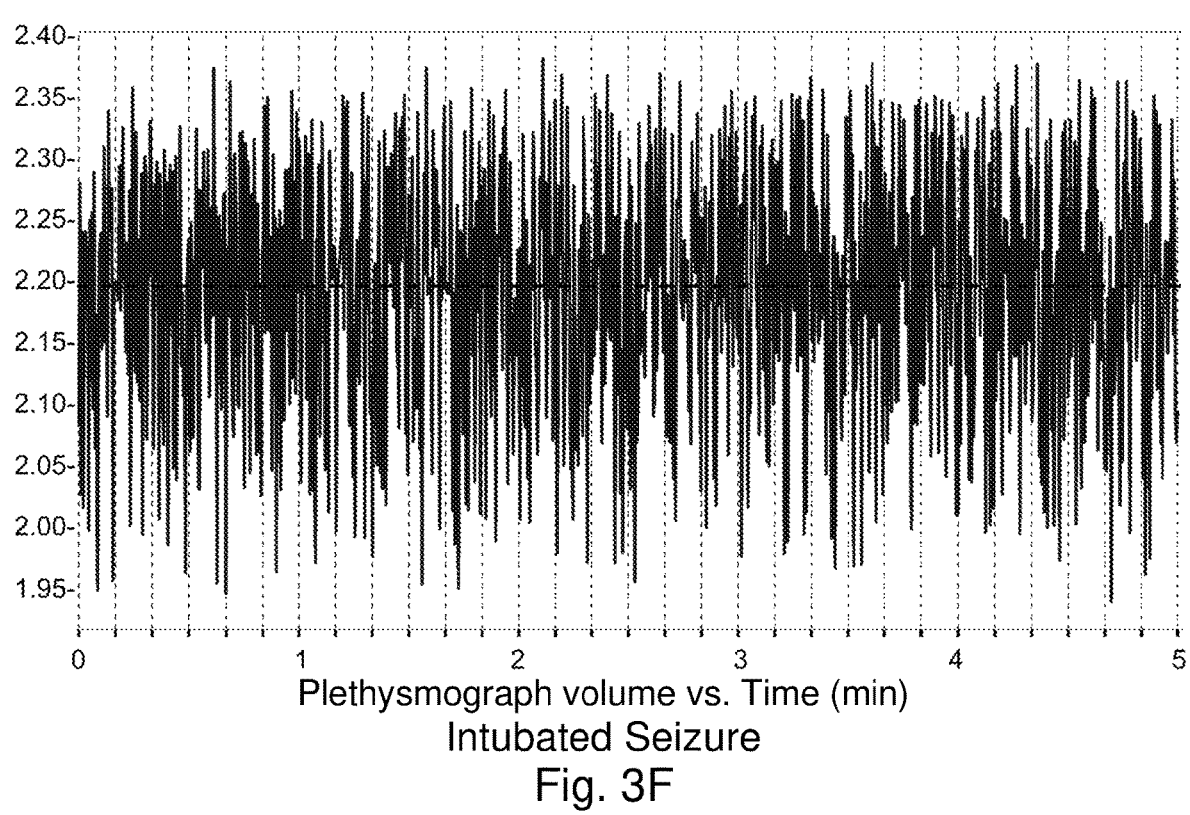
Figure 3G:
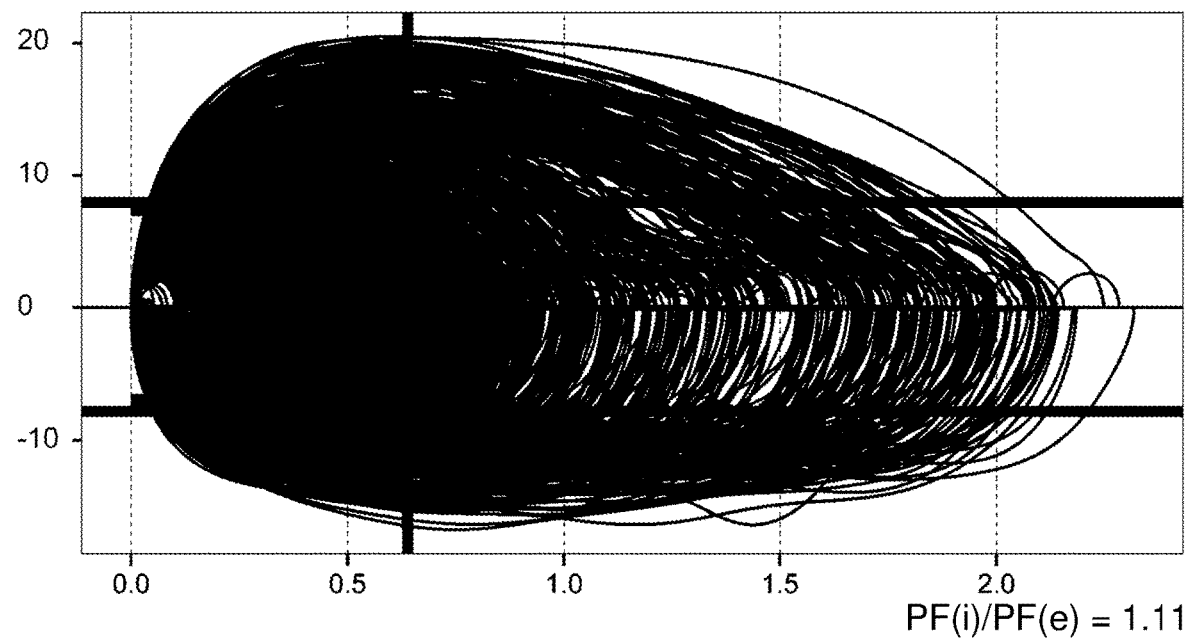
Figure 3H:
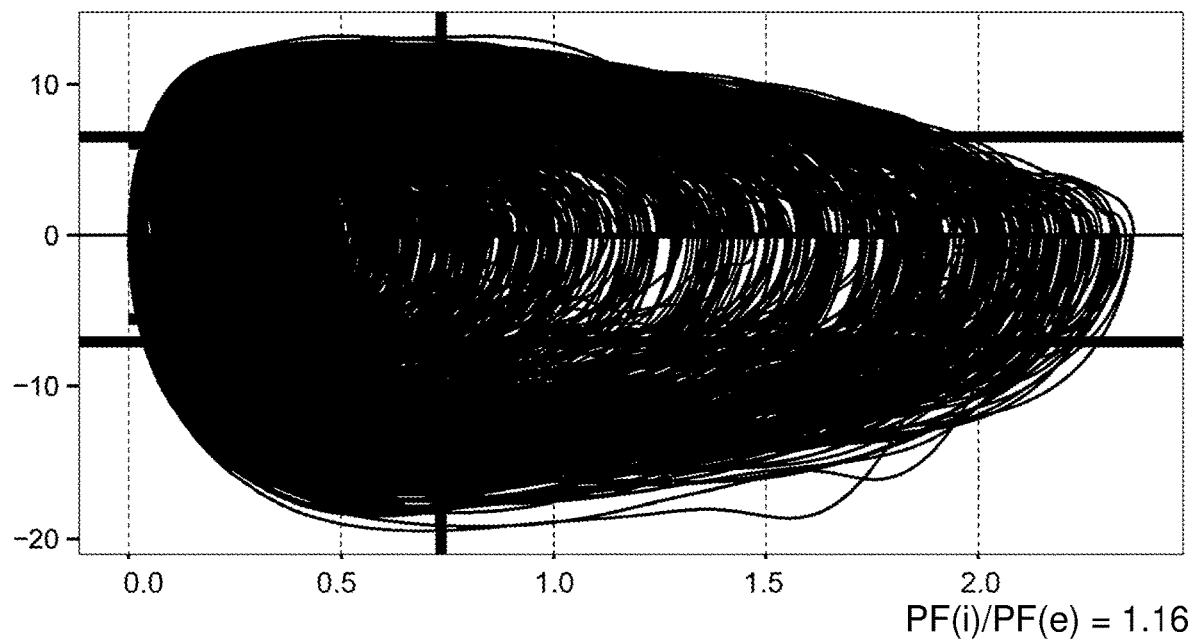

Seizure activity was associated with increases in RLN activity and abnormal, high frequency movements of vocal folds. Within a single seizure, RLN activity progressively increased, with the highest levels of activity most commonly observed near the end of the seizure. The full pattern of an RLN activity increase during a single seizure and its decrease to baseline at the end of the seizure could be observed when the airway was protected by a tracheal tube or window (FIG. 2). Laryngospasm during seizure activity had a significant impact on respiration FIG. 2 shows extreme increases in RLN activity during a seizure. Segments from a complete seizure are shown with normal respiratory bursting on RLN (top left, even lines) giving way to significantly increased firing (right side of top trace with maximum on right side of second trace) with eventual firing reductions (bottom trace). EEG is shown on odd lines. Estimates of seizure onset and offset (based on changes in low frequency activity and spiking) are marked with arrows. In these animals, the airway was protected with a tracheal implant or opening cut through the tracheal cartilage so that the entire profile of RLN activity during individual seizures might be captured.

During normal tidal breathing under urethane anesthesia, the early expiratory peak in rats resembles human breathing (Arito et al., 1997). Three of 14 non-intubated rats and 1 of 6 intubated rats had seizure activity mainly characterized by low frequency, repetitive gasping breaths and were not included in the summary data. Plethysmograph recordings were taken before and after SLN lesions in this subgroup, and before and after intubation in intubated animals. None of the measured parameters showed a difference due to SLN lesion or intubation. Pre-seizure values used for comparison with seizure values were the baseline condition for KA-only animals, the post-intubation condition for intubated animals, and the post-lesion condition for SLN lesioned animals. There were no differences between the two subgroups of non-intubated rats and their measures were pooled for statistics except when these two groups were compared with each other. Examples of flow-volume loops for non-intubated and intubated rats are shown in FIGS. 3A-3H.

FIGS. 3A-3H show plethysmography during baseline (FIGS. 3A-3D) and kainic acid-induced seizure activity (FIGS. 3E-3H). Head plethysmography examples are from one non-intubated (FIGS. 3A, 3C, 3E, and 3G) and one intubated (FIGS. 3B, 3D, 3F, and 3H) rat. The pre-seizure baseline condition for each animal is shown in FIGS. 3A, 3B, 3C and 3D and the corresponding seizure-associated condition is shown in FIGS. 3E, 3F, 3G, and 3H. For each figure, 5 minutes' worth of continuous breathing was analyzed to produce the flow-volume graph loops (FIGS. 3C-3D, FIGS. 3G-3H) in each case. The upper horizontal dotted line on each flow-volume graph (FIGS. 3C-3D, FIGS. 3G-3H) is the mean peak expiratory flow, the lower horizontal dotted line is the mean peak inspiratory flow, and the vertical dotted line is the mean tidal volume. Several key features are evident: 1) tidal volumes during seizure activity are lower for both animals; 2) the variability of breath flows and volumes during seizures are increased for both animals; 3) the ratio of peak inspiratory flow to peak expiratory flow is decreased for the non-intubated rat and increased for the intubated rat (calculated average shown at the upper right of each flow-volume (FIGS. 3C, 3D, 3G, and 3H) graph).

Seizure activity was associated with large increases in respiratory rate in all remaining rats (11 non-intubated and 5 intubated), irrespective of treatment, from mean pre-seizure rates of 85±11 and 98±17 breaths/min for non-intubated and intubated rats, respectively to seizure associated rates of 371±54 and 295±43 breaths/min. Increases were significant (p<0.0001) after Scheffe post hoc correction of multi-variate ANOVA. Pre-seizure mean rates of 89 and 81 breaths/min were observed in the 5 KA-only rats and the 6 non-intubated SLN lesioned animals, with seizure-associated mean rates of 371 breaths/min for both groups (p<0.0001 for both comparisons).

Other details are given in Table 1, which shows a summary of first and second order plethysmography variables. The full set of plethysmography variables measured are shown with details for baseline, post manipulation (intubation or SLN lesion) and during seizure activity. The manipulations (intubation or SLN lesion) did not change baseline values significantly for any parameter, but seizure activity changed many parameters related to durations and volumes in all animals. The principal measure to discriminate between non-intubated and intubated animals was the ratio of inspiratory peak flow to expiratory peak flow. Scheffe post-hoc corrections applied to one-way ANOVAs. A p value of 0 is used to indicate p<0.0001.

Tidal volume decreased significantly in the non-intubated rats. Mean pre-seizure tidal volumes of 1.50±0.36 ml/breath decreased to 0.46±0.14 ml/breath (p<0.0001). Subgroup tidal volumes were each significantly decreased: 1.2 to 0.46, p=0.008 for KA-only rats and 1.7 to 0.46, p<0.0001 for SLN lesioned rats). The difference in pre-seizure (1.03±0.69 ml/breath) vs. seizure (0.53±0.26 ml/breath) tidal volume in intubated animals did not reach statistical significance.

Given that ventilation rates increased approximately 3-fold and tidal volumes decreased approximately 3-fold during seizure activity, the average minute ventilation during seizure activity did not differ significantly from baseline, but tended toward lower values. Mean pre-seizure values of 124.8±27.3 and 124.2±61.8 ml/min were associated with mean seizure values of 100.8±35.7 and 93.2±42.3 ml/min (NS, NS) for non-intubated and intubated rats. Only the SLN lesioned subgroup showed a significant decrease in minute ventilation from 138.8±13.2 to 106±22.4 ml/min (p<0.0001). Mean pre-seizure and seizure values for the KA-only rats were not significantly different (108.0±25.0 vs. 94.4±49.7 ml/min; NS).

The most dramatic differences were seen in the ratio of peak flow during inspiration to peak flow during expiration. This parameter is used to identify upper airway obstruction. Normally, this ratio is ≥1, and values <1 are indicative of extrathoracic (e.g. upper airway) obstruction (Blitzer and Meyer, 2006; Miller et al., 1987). Mean pre-seizure ratios were 1.04±0.25 for non-intubated rats and 1.02±0.10 for intubated rats. These values changed in opposite directions for intubated (increasing to 1.56±0.38; p=0.011) and non-intubated rats (decreasing to 0.52±0.32; p<0.001). The individual subgroups of non-intubated animals each showed decreases in the ratio of peak flows during inspiration and expiration: 0.95 to 0.60 for KA-only rats (NS) and 1.11 to 0.46 for SLN lesioned rats (p=0.001). Whereas the decrease in PF(i)/PF(e) is consistent with partial airway obstruction from laryngospasm, the increase in PF(i)/PF(e) is clearly not from one of the typical causes of variable intrathoracic obstruction. Since there was no obstruction in the intubated animals, the flow-volume characteristics of the intubated animals reflect seizure-induced disordered ventilation without contribution from airway narrowing. If this is true, the decreased PF(i)/PF(e) seen in non-intubated rats should be considered an underestimate, more properly compared with the intubated rats' seizure condition than with their own pre-seizure condition.

Values are summarized in Table 2, which shows summary statistics from plethysmography data. To compensate for multiple ANOVAs, a difference score (seizure condition minus pre-seizure condition) was computer for each animal on the 4 variables derived from the plethysmograph (respiratory rate, tidal volume, minute ventilation, and the ratio of inspiratory peak flow to expiratory peak flow). A 2-tailed Mann-Whitney test was conducted of the difference of distribution of these change-scores between intubated and pooled non-intubated study arms. Bootstrapping (20,000 replications) was used (SAS 9.4 Proc Multtest) to arrive at corrected p-values for the four measures, based on independent samples 2-tailed t-tests performed on ranked scores.

Figure 4A:
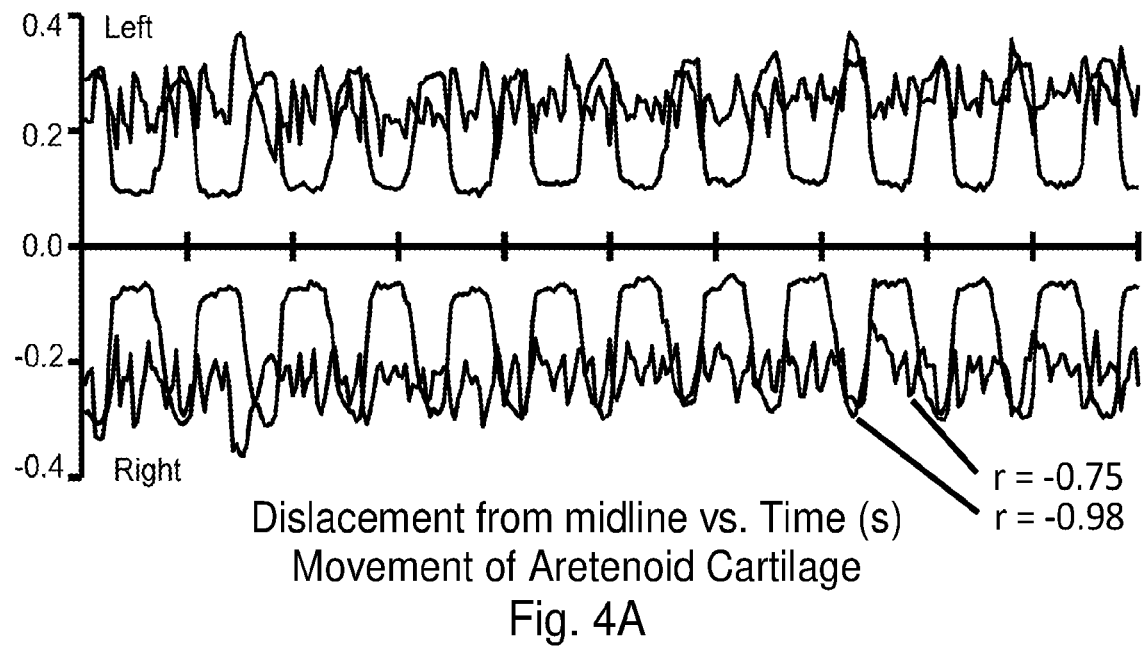
FIG. 4A shows a graph of movement of arytenoid cartilage over time.
Figure 4B:
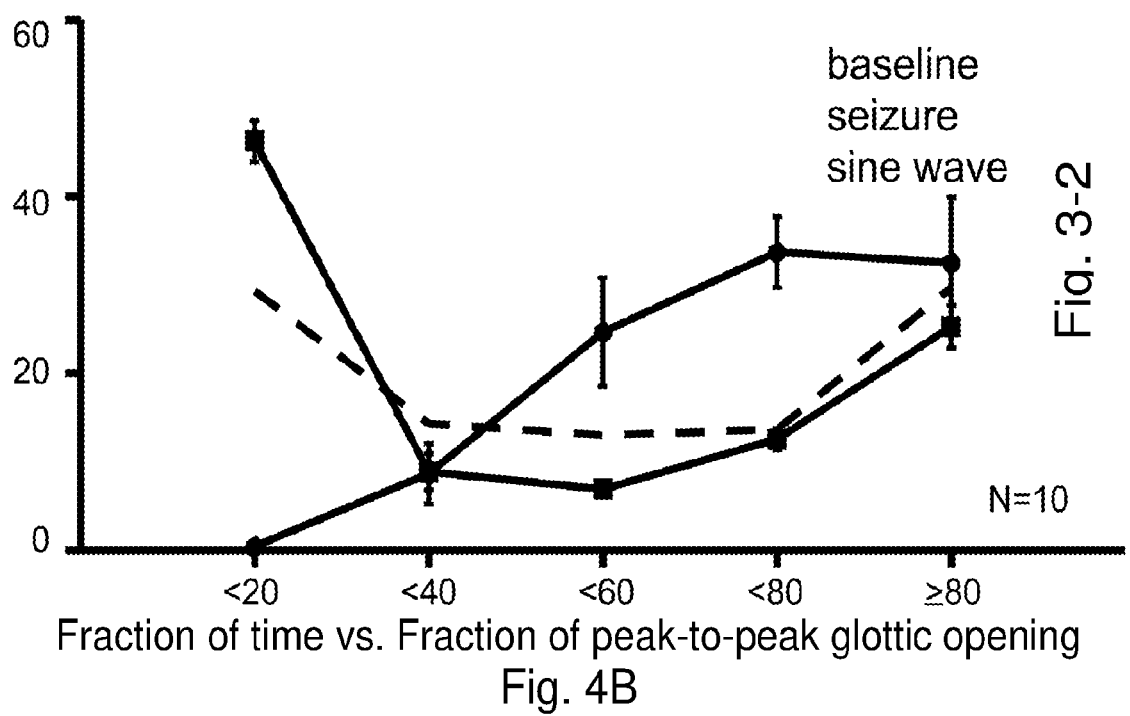
FIG. 4B shows a graph of average glottis opening during seizures over time, demonstrating show irregular vocal fold movement during seizure activity.

FIGS. 4A and 4B show irregular vocal fold movement during seizure activity. Laryngoscopy during seizure activity revealed "shaking" movements of the arytenoid cartilages consistent with the findings of partial obstruction from plethysmography and abnormal RLN activity. In analyses of video recordings of laryngeal vocal fold and arytenoid cartilage movements, the highly correlated movements of the left and right arytenoid cartilages uncouple partially from an average Pearson correlation of −0.95±0.04 to −0.79±0.11 (n=10; p=0.0007), as shown in FIG. 4A. Frame-by-frame analysis of vocal fold and arytenoid cartilage position during video recordings of laryngoscopy show the typical coordinated abduction and adduction (periodic low frequency trace of upper graph of FIG. 4A) of the vocal folds during respiration. The position of the left arytenoid cartilage relative to the midline is shown as an upward deflection in the top graph, and the right arytenoid cartilage position is shown as a downward deflection. The correlation is high (0.98). During seizure activity (high frequency trace), the total displacement is less, the frequency is higher, and the correlation is decreased (0.75).

The distributions of time in quintiles of the peak-to-peak glottic opening (measured at baseline) is shown in FIG. 4B. The distribution of times across degrees of glottic opening (bin sizes=20% of minimum to maximum opening in the baseline condition) were shifted toward larger openings, but with less variation in glottic opening. In fact, the average total normalized glottic opening over 10 seconds was larger during seizure activity than during baseline (0.36±0.03 baseline, 0.47±0.06 seizure; p=0.00005). At baseline (squares), the largest fraction of time is in the closed position, with rapid cycling through open angles. The distribution of times for a sine wave are shown for reference (dotted line). During seizure activity, the profile is changed significantly (circles) with a larger fraction of time in relatively open states, which would seem to mitigate the relatively stationary opening. Data are shown as means±standard deviations.

Whereas clear evidence of partial airway obstruction due to laryngospasm was routinely observed, the modest decreases in minute ventilation suggested that respiratory derangements during seizures were adequately compensated. However, complete glottic closure (confirmed with laryngoscopy) occurred in a subset of non-intubated animals during discrete seizures in association with the largest increases in RLN activity, and cessation of airflow was followed in all animals within tens of seconds with ST segment elevations in ECG, bradycardia, and eventually death. Complete obstructive apnea occurred in 7 of 11 non-intubated and 0 of 5 intubated rats (p=0.03, Fisher exact test, two-tailed). All 7 animals died. The start of the obstructive apneic period was taken as the time from the point at which peak-to-peak airflow reached <10% of the pre-apneic peak-to-peak airflow, and the endpoint was the time at which the recording was stopped and the animal removed from the plethysmography chamber with evidence of severe bradycardia on ECG that, upon removal from the plethysmography chamber, was associated with apparent cardiopulmonary arrest. Only when an artificial airway was present was a period of complete glottic closure due to laryngospasm seen to terminate on its own with a reversion to the normal pattern of opening and closing with each breath.

Figure 5:
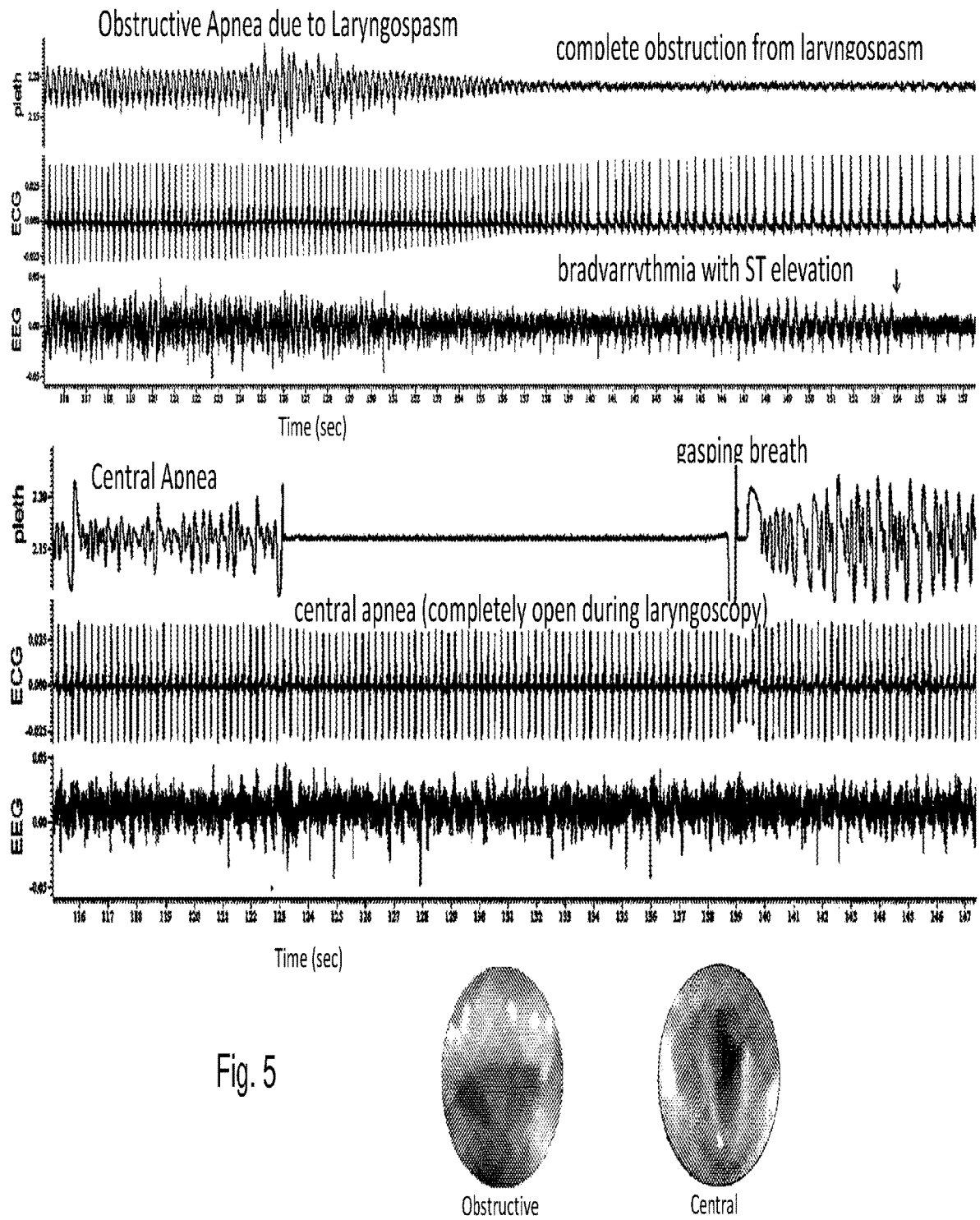
FIG. 5 shows obstructive and central apnea during seizures.

FIG. 5 shows obstructive and central apnea during seizures. The top panel illustrates an episode of obstructive apnea due to laryngospasm with hypoxic cardiac arrhythmia. Each set of traces consists of plethysmography (top); ECG (middle); EEG (bottom). The obstructive apnea develops as a rapid, but continuous (several seconds) reduction in the amount of air per breath until that amount is negligible. At the time indicated as complete obstruction (confirmed by simultaneous laryngoscopy—single frames shown at the right), the ECG develops clear bradyarrhythmia with ST segment elevation from hypoxemia develops. The recording is taken from the end of a seizure; seizure activity is present from the beginning of the illustrated data and an estimate of seizure offset (based on a complete flat-lining of EEG) is marked by an arrow. Episodes of central apnea, by contrast, were characterized by an abrupt cessation of breathing and air flow, but the vocal folds arrested in an open position (video frame at right). There were no cardiac derangements over the same time period. The entire record, taken from the middle of a seizure, displays seizure activity.

On plethysmography records, airflow declined rapidly to zero or near zero flow (FIG. 5, top). In every case, ST-segment elevation on ECG recordings was clear evidence of hypoxemia. Laryngoscopy revealed complete glottic closure. The shortest duration period of obstructive apnea to produce apparent cardiopulmonary arrest was 56 seconds. RLN activity recorded with laryngoscopic confirmation of glottic closure (n=2) showed intense firing associated with the laryngospasm and ECG evidence of hypoxia (FIG. 5, top). The occurrence of laryngospasm in SLN-lesioned animals is further evidence that laryngospasm was not mediated by pharyngeal/laryngeal reflexes that might have been activated by the laryngoscope or salivation.

Figure 6:
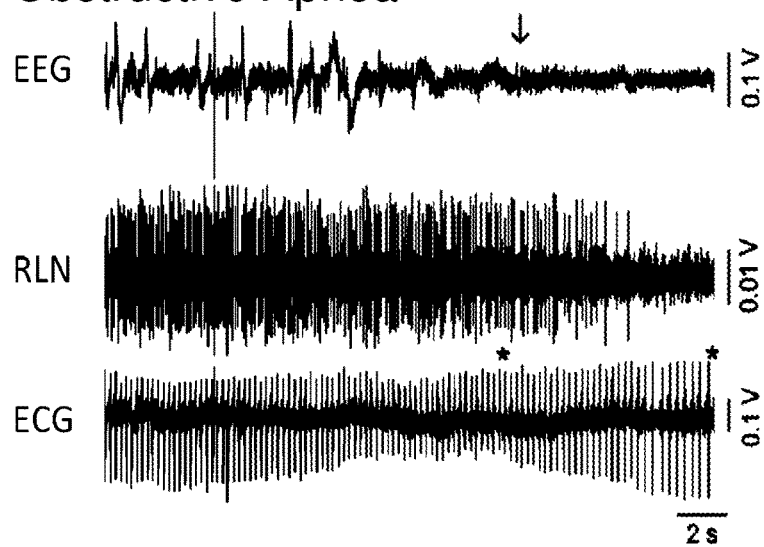
FIG. 6 shows recurrent laryngeal nerve activity during obstructive and central apnea.
Figure 6:
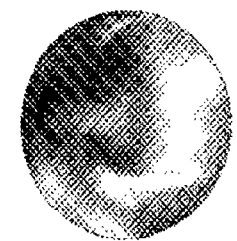
Figure 6:
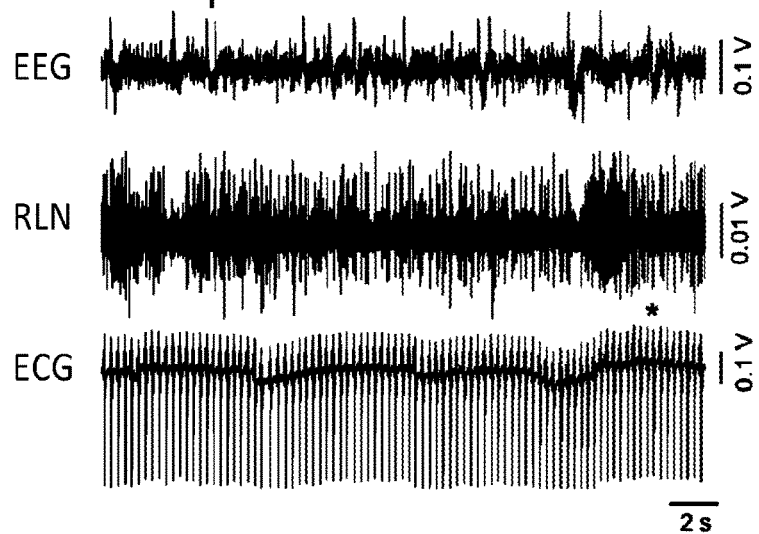
Figure 6:
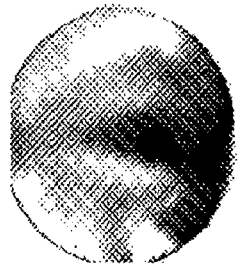
Figure 6:
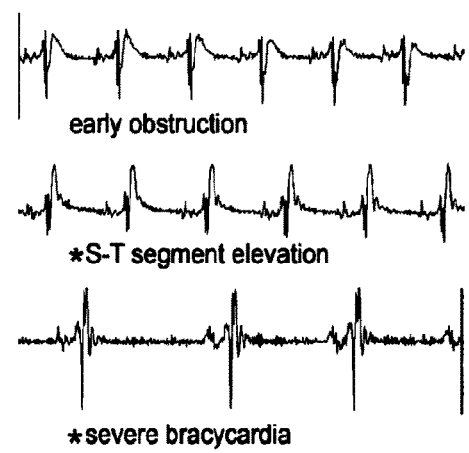
Figure 6:
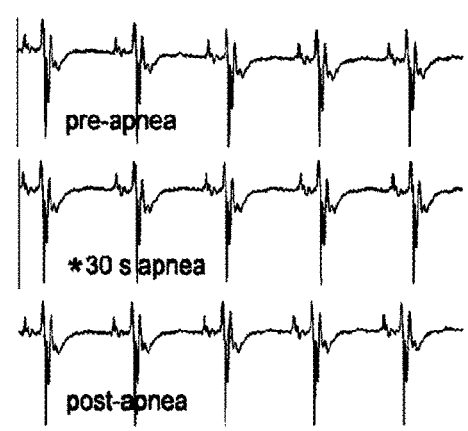

FIG. 6 shows recurrent laryngeal nerve activity during obstructive and central apnea. RLN firing (middle trace of each panel) during obstructive apnea (top panel) and central apnea (bottom panel) show that the RLN is active during both types of apnea. The RLN carries motor output for both laryngeal abductors and adductors. The multi-unit recordings do not permit discrimination of nerve activity for abductors or adductors, but adduction dominates during obstructive apnea and abduction dominates during central apnea. Video frames are shown to the right. Also shown to the right are three ECG sweeps for each type of apnea to illustrate the pronounced ST segment elevation and slowing during obstructive apnea and the uniform PQRST complexes during central apnea. The recording illustrating obstructive apnea is taken from the end of a seizure; seizure activity is present from the beginning of the illustrated data and an estimate of seizure offset (based on a complete flat-lining of EEG) is marked by an arrow. In contrast to systemic impact of obstructive apnea, periods of central apnea, characterized by an abrupt cessation of breathing effort, a completely open glottis, moderate RLN firing, and no air flow on plethysmography, were never associated with ST segment elevation in ECG or any other evidence that these episodes might be life threatening (FIG. 5, bottom and FIG. 6, bottom; Table 3).

Table 3 shows contrasts between obstructive apnea and central apnea. Details of obstructive and central apneic periods captured in non-intubated and intubated rats. Obstructive apnea appeared only in non-intubated rats, a difference that was significant (p=0.034). Central apneic periods averaged durations <10 seconds, but some periods exceeded 30 seconds in duration. To compare the impact of apnea of either type on cardiac activity, HR and the presence or absence of ST segment elevation were compared over equivalent 10 second periods from the onset of apnea based on plethysmography records. ST segment changes were only seen during obstructive apnea periods. Taking the minimum HR over this period in comparison with baseline, both obstructive and central apneic periods were associated with significant bradycardia, but the changes associated with obstructive apnea were greater. All comparisons were two-tailed unpaired t-tests.

Figure 7:
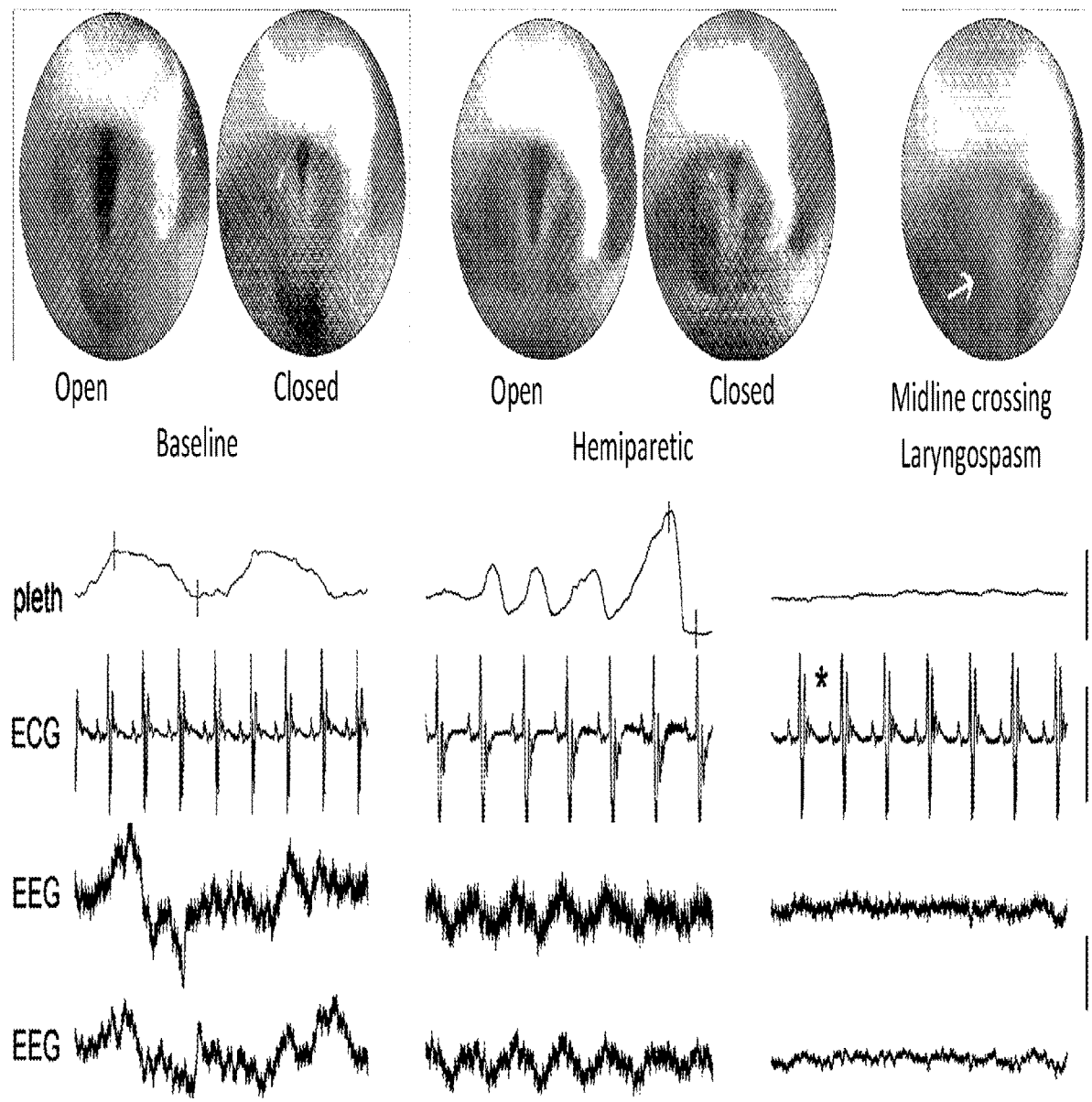
FIG. 7 shows a laryngoscope view, plethysmograph trace, ECG, and EEG (×2) tracings in a baseline state (left), hemiparetic (middle), and laryngospasm (right) states.

As further evidence that the glottic closure was active and not passive (e.g. resembling vocal fold paralysis (Mor et al., 2014)), plethysmography was performed, and recorded vocal fold motion in an animal whose right vocal fold was paralyzed by RLN damage (FIG. 7, hemiparetic). During a seizure-induced period of obstructive apnea, the ECG shows ST-segment elevation and the plethysmograph shows an absence of air movement. The force of contraction of the left vocal fold actually pushed the arytenoid cartilage across the midline in the absence of resistance from the right vocal fold.

FIG. 7 also shows a demonstration of the force of contraction during laryngospasm. In this example, the normal open and closed states of the arytenoid cartilages are illustrated in the baseline panel (left) together with plethysmography, ECG, and EEG records taken simultaneously. The tick marks on the plethysmography records indicate the time of the video snapshots. Note that the glottis is not completely closed, even at the minimum of arytenoid excursions from the midline. In the center panel, the right vocal fold was paralyzed by crushing the right RLN to cause hemiparesis. Breathing is changed from regular large breaths to more frequent smaller breaths mixed with large gasps. The far right panel shows a segment taken from the same rat during seizure induced laryngospasm sufficient to produce obstructive apnea. The glottis is completely closed, but note how left side of the larynx actually crosses the midline when not opposed by an active right side (white arrow in video snapshot). Also note the ST-segment elevations are prominent (asterisk on ECG trace) in contrast with the other two states. (Calibrations: 0.5 sec, 0.25 ml (pleth), 0.5 mV (ECG), and 0.1 mV (EEG)).

The lethality of obstructive apnea periods is contrasted with the minimal impact of central apnea periods in the same animals. That these transient periods of central apnea are separate from the central apnea that characterizes respiratory arrest. Periods of central apnea were defined by an abrupt cessation of breathing for periods ≥1 second as evidenced in plethysmography records. These were recorded during seizure activity in animals of all groups with no differences in the frequency or duration of central apneic periods between groups. No central apneic periods were ever seen in baseline, pre-seizure/post-intubation, or pre-seizure/post-SLN transection conditions. Three of 6 KA-only animals showed central apneic periods, compared with 3/5 SLN-lesioned animals, and 5/5 intubated animals. Central apneic periods as long as 33 seconds were recorded. The mean durations and counts of central apneic periods ≥1 s, and the subset of periods whose durations were ≥5 s are detailed in Table 3.

Two findings highlight the contrast between obstructive and central apnea. First, on laryngoscopy during central apneic periods, the vocal folds were abducted and immobile and held the glottis in a completely open configuration for the entirety of the apneic period (FIGS. 5, 6). The open state of the larynx is an active state, as shown by RLN activity during central apneic periods. Second, bradycardia developed to a much greater extent, plus ST-segment elevation was prominent, during periods of obstructive apnea, but not central apnea. While it is true that the obstructive apnea periods lasted longer than central apnea periods (all central apnea periods ended spontaneously with a return to pre-apneic respiratory patterns), at the same time from apnea onset, only obstructive apnea impacted cardiac function. Taking all central apneic periods of 15 seconds or greater from all groups into a single pool (n=9 apneic periods from 6 animals), the change in heart rate within the time window of 5-15 seconds was examined for comparison with the mean heart rate pre-apnea. The mean and minimum heart rate measures during the 5-15 second time window of obstructive apnea were significantly decreased compared to pre-apnea rates. For central apneic periods, the minimum heart rate during 5-15 seconds was significantly decreased, but not the mean rate for the 10 second epoch. In comparing the relative changes, heart rate decreases during obstructive apnea (−31.4±13.9% change, n=7) were significantly greater than central apnea (−17.3±9.7% change, n=9) over the same time frames (Table 3). The average minimum heart rate for periods of obstructive apnea before stopping the recordings was 0.86±0.38 beats/s (down from >6 beats/s at baseline).

A series of experiments were conducted in which a controlled complete occlusion of the airway was used to study response kinetics without the uncertainty of when complete obstruction would occur during seizure activity. A T-shaped tracheal tube was implanted after dissecting the RLN free bilaterally. This enabled securing the tracheal tube in place without disturbing normal laryngeal function. A pressure transducer on the tracheal tube sidearm recorded forces developed during either normal breathing with the tracheal tube open to the atmosphere or during complete closure of the open port with an airtight cap. Complete obstruction of the airway was performed for 100 seconds or until 20 s after respiratory arrest occurred, whichever was earlier. In addition to tracheal sidearm pressures, ECG and pulse oximetry were recorded continuously. In subsets of animals, echocardiography and/or continuous arterial blood pressure monitoring were performed.

During occlusion, respiratory effort to inspire progressively increased, then ceased, usually in less than 1 minute (60.4±24.0 s; median=54.4 s; n=16). Respiratory arrest was associated with cardiac dilatation and asystole, an increase of systemic blood pressure (which collapsed without resuscitation), and laryngospasm sufficient for complete glottic closure. This is a type of central apnea that differs from the central apneic episodes reported earlier that were associated with an actively open airway. The LV diastolic cavity size became dilated by about 40% (0.47±0.07 at baseline to 0.64±0.22 cm 10 sec after respiratory arrest) and the end systolic LV cavity size became dilated by nearly 300% (0.12±0.03 at baseline and 0.44±0.23 cm 10 seconds after respiratory arrest). The LV ejection fraction fell from 94±2 to 49±23 percent.

Figure 8:
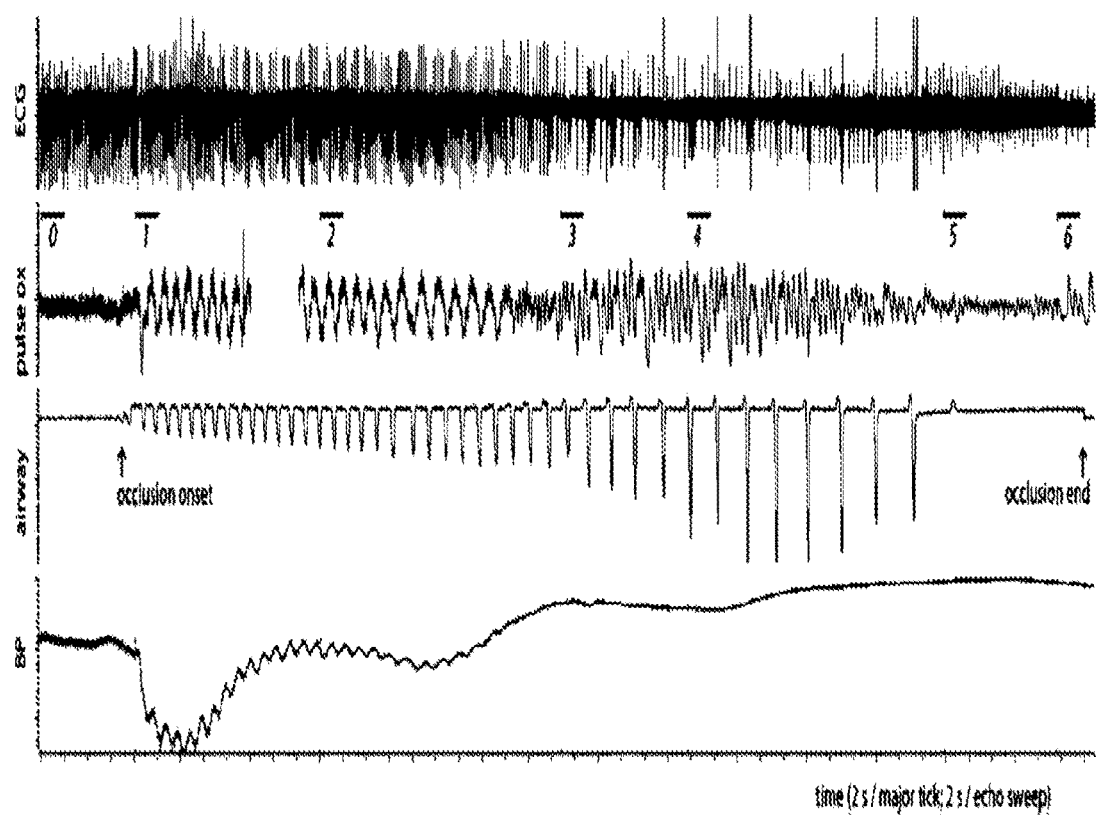
FIG. 8 shows concurrent tracings of ECG (top), pulse oximeter (second from top), airway pressure (second from bottom), and blood pressure (bottom) during upper airway occlusion.
Figure 9:
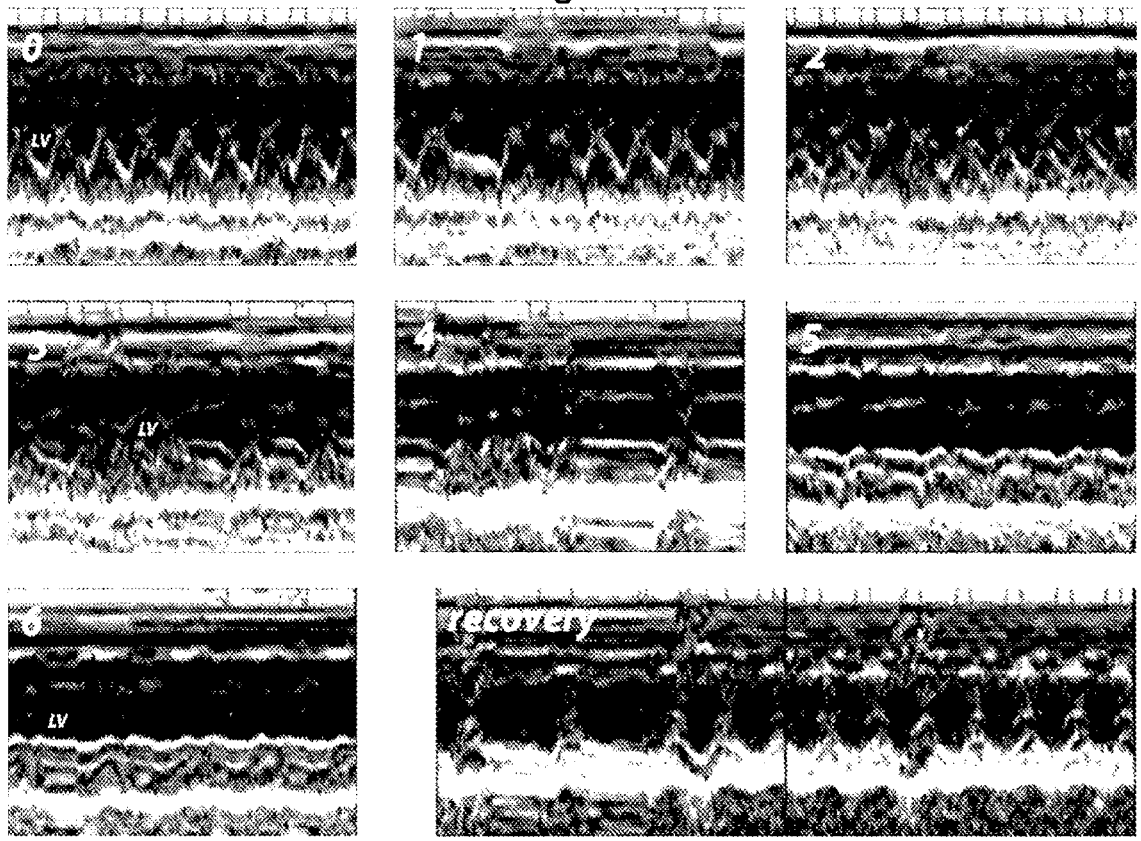
FIG. 9 shows echocardiography during controlled airway occlusion.

An example experiment is illustrated in FIG. 7 and the cardiac and respiratory function parameters are summarized in FIGS. 8 and 9, which show echocardiography during controlled airway occlusion. FIG. 8 shows ECG, pulse oximetry, airway pressure transducer, and arterial blood pressure records during a 100 second occlusion of the trachea (onset and end marked with arrows). The development of bradyarrhythmia and the progressive inspiratory effort are clearly visible. The inspiratory effort is sufficient to significantly impact blood flow as evidenced by the larger pulse oximetry waves associated with each attempt to breathe. FIG. 9 shows a series of M-mode echocardiogram panels, each representing a respective 2-second period which has a reference number corresponding to the markings in the ECG trace of FIG. 8. Normal cardiac function is visible in the pre-occlusion record (panel 0 of FIG. 9). Panels 1-6 of FIG. 9 occur at points during the period of occlusion and show rhythm abnormalities and progressive left ventricular dilation. By the time respiration has arrested (echo panel 5 of FIG. 9), the heart is nearly akinetic. The recovery panel shows the abrupt return of cardiac performance after the airway obstruction has been removed and breathing has recovered. Major ticks on each plot in top panel: ECG=0.25 mV; pulse ox=5% variation (high pass filtered); airway transducer=25 mmHg; BP=10 mm Hg.

Example 3

Figure 10:
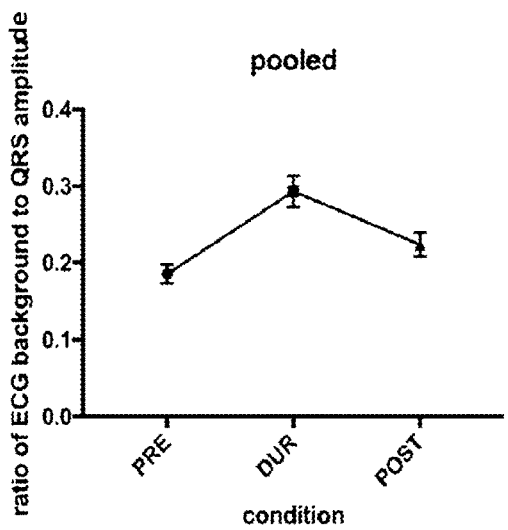
FIG. 10 shows a graph of a pilot test in human subjects of biomarker 1 (the increased peak-to-peak amplitude of an ECG recording's background activity, which is due to increase thoracic muscular EMG getting included in the ECG signal) during attempts to inspire against an occluded upper airway.

FIG. 10 shows results of a pilot human trial showing the use of biomarker 1 (the increased peak-to-peak amplitude of an ECG recording's background activity, which is due to increase thoracic muscular EMG getting included in the ECG signal) to detect obstructive apnea. The preliminary human subject data shows that biomarker 1 appears in a simple setting where patients try to inspire by drawing air out of closed 500 ml container. Significant increases in ECG background amplitude relative to QRS amplitude (simple ratio of peak-to-peak ECG signal to the peak-to-peak amplitude of the QRS complex) occur during the inspiratory effort.

This demonstrates that biomarker 1 has utility in any condition where EMG associated with inspiratory effort can be increased.

In FIG. 10, a statistical analysis of the results showed:
ANOVA: F (1.487, 43.13)=22.42 P<0.0001
Multiple Comparisons:
PRE vs. DUR p=0.0001
PRE vs. POST p=0.0128

Example 4

Tracheal tubes were placed in four rats, and strong seizure activity induced with kainic acid. In three rats, systemic variables to describe the sequence of events leading to death were monitored. During the period continuous seizure activity (status epilepticus), shallow, irregular breathing was mixed with gasping breaths that occurred at a rate of 1/s, but dropped abruptly to $\frac{1}{15}$ s before apparently stopping completely. Although the airway was completely open, oxygen saturations of 54 or 77% (no data for 3rd rat) preceded the transition to very slow or arrested breathing. The rate of change of oxygen saturation over time was well fitted with a straight line (slope=−0.07±0.05 pulse oximetry percentage points per second, R2 v=0.93±0.04). From these values, an average 10% drop in oxygen saturation took 135 seconds (2.25 minutes)—compared with times of <10 seconds after onset of laryngospasm-induced obstructive apnea or controlled occlusion. Whereas these animals demonstrated that, during periods of sustained seizure activity, very low oxygen saturations and death could occur with an intact airway, the times for desaturation were so long that this mechanism is unlikely to be the principal mechanism for desaturation during discrete seizures. Rather, this mechanism is likely a distinct feature of status epilepticus.

Figure 11:
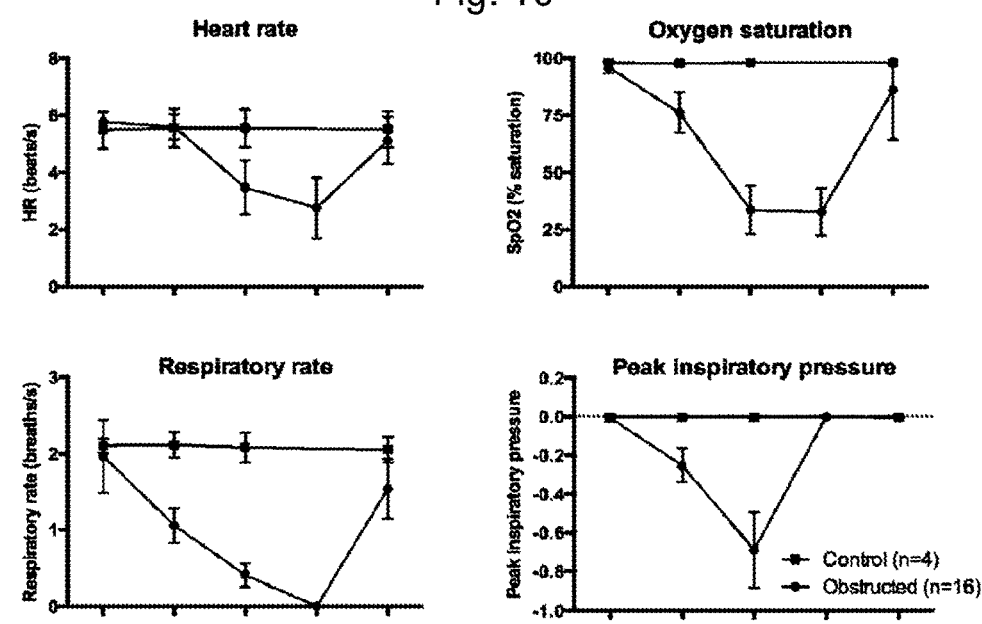
FIG. 11 shows a summary of cardiac and respiratory parameters during controlled airway occlusion.
Figure 11:
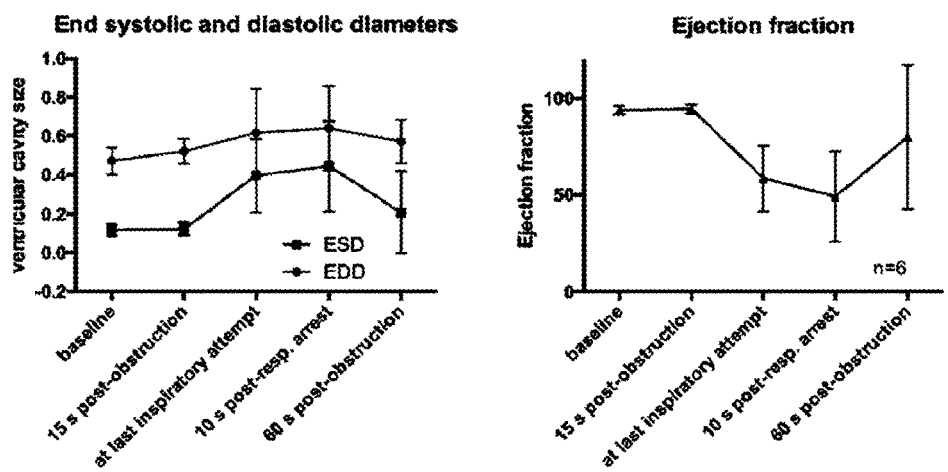

FIG. 11 shows a summary of cardiac and respiratory parameters during controlled airway occlusion. Changes in heart rate derived from ECG, arterial oxygen saturation based on pulse oximetry, respiratory rate and peak inspiratory pressure derived from a pressure transducer on the sidearm of a tracheal implant, and left ventricular cavity size and ejection fraction derived from echocardiography. A pre-occlusion baseline point is compared with three time points during controlled airway occlusion (15 s after onset, at the time of respiratory arrest, and 10 s after respiratory arrest), and recovery (60 s after the end of resuscitation efforts). Each point is shown as its mean and standard deviation. Obstructed animals (squares) are also compared with unobstructed control animals (circles) for some measures. Changes in respiratory parameters and oxygen saturation occur, in general, earlier than changes in cardiac parameters as evidenced by statistically significant decreases in these parameters by 15 s after the onset of airway occlusion. By the time of respiratory arrest, left ventricular performance is significantly impaired as illustrated with significant dilatation (enlarged end systolic dimension) and decreased ejection fraction. Units for plots: HR (beats/s), oxygen saturation (% saturation), respiratory rate (breaths/s), peak inspiratory pressure (mmHg/100), ventricular cavity size (cm), and ejection fraction (% diastolic volume ejected during systole).

Unlike laryngospasm-mediated obstruction where the vocal folds were continuously adducted, during the period of vocal fold obstruction, each attempted inspiration was associated with an opening and closing of the airway by vocal fold movements such that the degree of opening increased as the inspiratory effort increased. Each glottic opening was followed by a complete closure of the airway due to fully apposed arytenoid cartilages and vocal folds. The maximal opening angle during the last breath attempt was 56.7±5.3° compared to baseline values of 27.6±4.6° (p<0.00001). After the last breath attempt, the airway stayed in this closed position for an additional 20-60 seconds before normal breathing and vocal fold motion resumed after resuscitation or a small glottic opening became evident when the vocal folds appeared to relax in animals that were not resuscitated.

From the point of the last apparent breath, a minimum in heart rate was reached in 30, 70, or 140 seconds. In two animals, laryngospasm was recorded only after the appearance of bradycardia because the larynx was not being continuously monitored. For the third rat, first evidence of laryngospasm was captured on video. This showed that breathing appeared to stop 18 seconds before laryngospasm and cessation of seizure activity as evidenced by flattening of the EEG. Whereas hypoxia-induced laryngospasm such as that described in the controlled occlusion experiments might account for the laryngospasm observed in the first two rats, laryngospasm in the third rat was uncoupled from the respiratory pattern and apparently still driven by seizure activity.

The key findings of these studies are that: 1) seizure activity causes large increases in RLN activity; 2) seizure activity changes breathing frequency, amplitude, variability, and can cause central apnea; 3) seizure activity causes laryngospasm that can result in partial or complete airway occlusion (obstructive apnea); 4) only obstructive apnea was associated with rapid, severe arterial oxygen desaturation, bradycardia, respiratory arrest, and death; 5) hypoxemia itself can cause laryngospasm, significantly prolonging complete airway closure; and 6) sudden death is the result of respiratory arrest during airway obstruction and nearly simultaneous left-ventricle dilatation and asystole. From this set of findings, it is concluded that sudden death in any animal or person experiencing a seizure can be the result of seizure-induced laryngospasm sufficient to cause obstructive apnea, which leads to respiratory arrest and cardiac asystole within tens of seconds, and which can only be reversed by cardiopulmonary resuscitation (i.e. spontaneous recovery is highly unlikely).

Seizures clearly disrupt normal breathing. Respiratory frequency, tidal volume, and cycle variability were all changed by seizure activity. More severe outcomes were marked by periods of no airflow at all, either because the drive to breathe ceased while the glottis was fully open (central apnea) or because the glottis was closed due to laryngospasm (obstructive apnea). The most significant impact on oxygen status and cardiac and respiratory function was from obstructive apnea secondary to seizure-induced laryngospasm. A straightforward interpretation of these observations is a spread of seizure activity along the pathway from subiculum to paraventricular nucleus (PVN) of the hypothalamus (Canteras and Swanson, 1992) and from PVN to medullary regions (e.g. (Geerling et al., 2010)), where it impacts medullary autonomic nuclei, respiratory centers, and laryngeal motor neurons.

What is it about seizure-induced obstructive apnea that resulted in such rapid and severe cardiopulmonary dysfunction? The lack of airflow could not have been the problem since the periods of central apnea did not cause the same deterioration. The remarkable feature of the obstructive apneas was that the airway was completely shut. The forces of vocal fold contractions during seizure-induced laryngospasm were illustrated by the fact that an active vocal fold actually crossed the midline when it was not opposed by a paralyzed vocal fold and the fact that the usual opening of the vocal folds during attempts to gasp did not occur. By contrast, the vocal folds were always in a completely open position during periods of central apnea. It is conceivable that the occurrence of laryngospasm merely reflected a level of seizure activity that caused cardiopulmonary dysfunction by a mechanism independent of obstructive apnea. However, when the airway was manually occluded by closing a tracheal tube in rats that had not been treated with kainate and were not undergoing seizures, the same sequence and time course of events was observed: oxygen desaturation, bradycardia, and ST-segment elevation within seconds, respiratory arrest and serious cardiac mechanical failure within about one minute, and cardiac arrest within several minutes. The combination of these findings indicates that it is the airway occlusion that triggers cardiopulmonary collapse and death.

A major difference between central and obstructive apnea relates to the intense autonomic response that comes during attempts to breathe against a closed airway or during asphyxiation (e.g. (Brostrom et al., 2007; Hotta et al., 2009; Weiss et al., 2015)), but does not occur in the absence of a drive to breathe. Breath holding can last for long times without detriment; the current world record in humans exceeds 11 minutes, or over 22 minutes after hyperventilation with pure oxygen (Association Internationale pour le Développement de l'Apnée; www.aidainternational.org/). It involves a voluntary reduction of the drive to breath, but does not require closing the glottis (Donzelli and Brady, 2004; Mendelsohn and Martin, 1993) and does not significantly activate the autonomic nervous system. Seizure-induced central apneas are generally harmless because they induce only a minimal autonomic and systemic response in the absence of a drive to breathe. Seizure-induced obstructive apneas, in contrast, are deadly because the attempt to breathe against a closed airway triggers a strong autonomic co-activation, on top of an already raised autonomic tone due to the seizures themselves, that ultimately results in cardiopulmonary collapse.

Given the complexity and interdependence of the cardiac, respiratory, and nervous systems, the question arises whether laryngospasm is both necessary and sufficient for sudden death. First, seizure-induced laryngospasm is not reflex-driven by salivation or other pharyngeal stimuli because a subgroup of non-intubated rats had bilateral superior-laryngeal-nerve lesions that would abolish the afferent limb of a reflex to drive laryngospasm. All of the deaths observed during the plethysmography experiments occurred with a sequence of seizure-induced laryngospasm followed by respiratory and then cardiac arrest with exactly the same temporal profile observed during the controlled occlusion of tracheal implants. Therefore, closing the airway by itself crosses a critical threshold and that seizure-induced laryngospasm is sufficient for sudden death.

The MORTEMUS heart rate data show that 9/10 patients experienced the largest drop in heart rate during the period of apparent respiration at the end of the seizure (FIG. 3 of Ryvlin et al., 2013) and before the onset of terminal apnea. The timing of the sharp drop in heart rate in the present rat experiments corresponds to a point late in the period of obstruction, after the seizure would have been terminated (Stewart, 2008), but before the point of respiratory arrest, which are believed to correspond to the onset of terminal apnea in the MORTEMUS study (Ryvlin et al., 2013). It is not only possible, but probable that the SUDEP cases of the MORTEMUS study experienced obstructive apnea as evidenced by the same terminal sequence of events leading to respiratory arrest and death as found for rats.

Laryngospasm may contribute to sudden death even in cases when it is not the initial trigger. In the manual airway occlusion experiments, laryngospasm was observed after respiratory arrest. This complicates the interpretation of clinical case reports since the presence of laryngospasm postictally may indicate either laryngospasm-mediated hypoxia or hypoxia-mediated laryngospasm. More ominously, whether laryngospasm starts the desaturation or occurs after desaturation, it guarantees that death occurs unless cardiopulmonary resuscitation is initiated shortly after respiratory arrest (when there is no effort to breathe and the heart is severely dilated).

A sequence of events is defined that links seizures to sudden death. In particular, seizure-induced laryngospasm resulted in cessation of airflow, followed within tens of seconds by ST-segment elevation, bradycardia, and respiratory arrest. These data were obtained in an established animal model for seizure experiments (urethane-anesthetized rats treated with kainic acid), not in humans, but demonstrate the utility of this rat model for studying laryngospasm and obstructive apnea.

Figure 12:
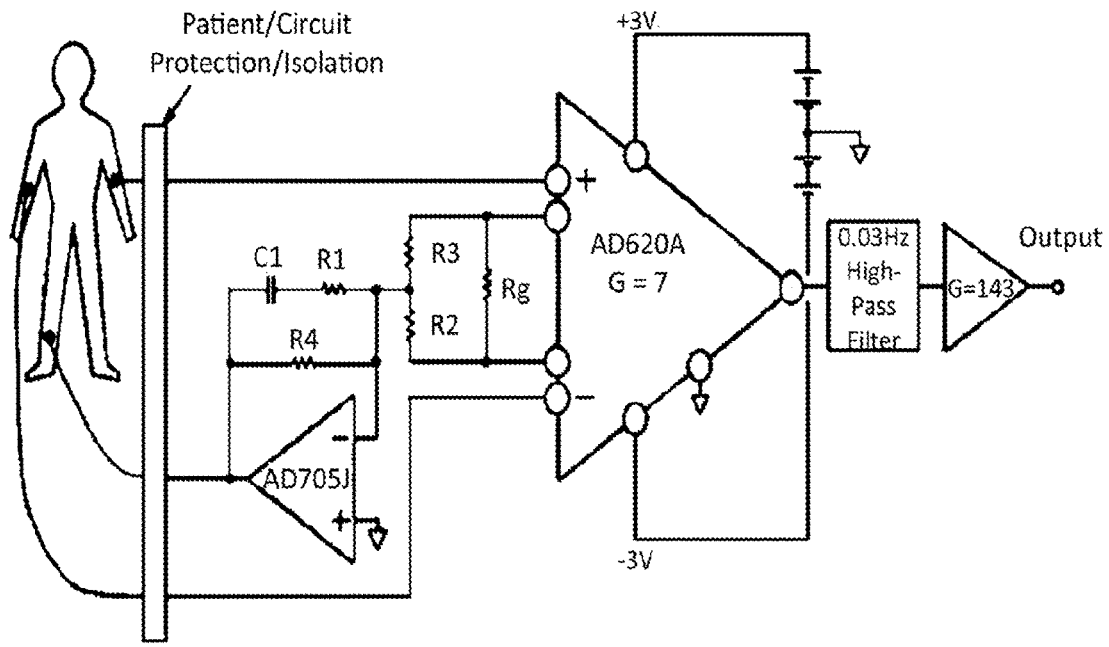
FIGS. 12 and 13 show various prior art ECG acquisition systems.
Figure 13:
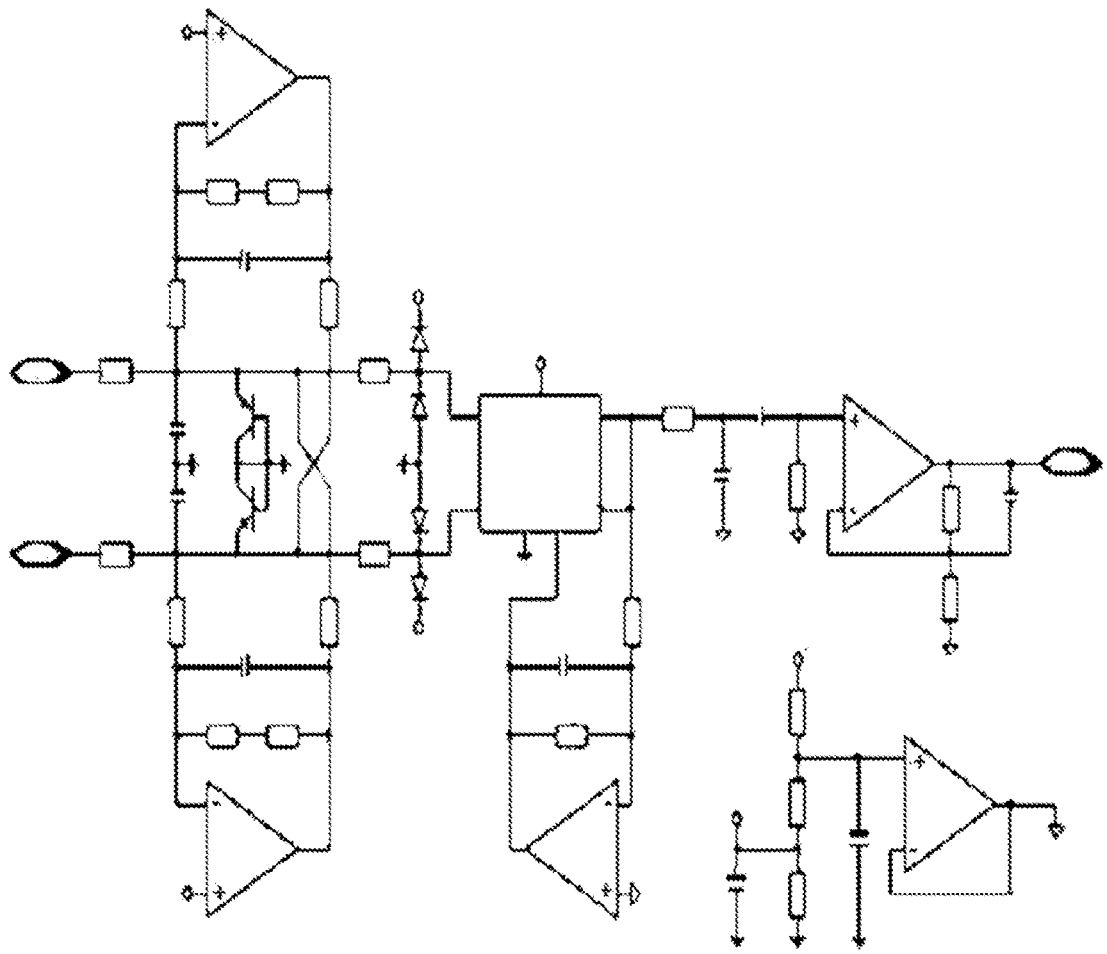

FIGS. 12 and 13 show prior art ECG acquisition circuits. See www.electro-tech-online.com/attachments/untitled-gif.26911/; www.electro-tech-online.com/attachments/ecg-circuit-png.26416/; and gasstationwithoutpumps.files.wordpress.com/2012/08/dobrev-amp.jpg, each of which is expressly incorporated herein by reference in its entirety.

Figure 14:
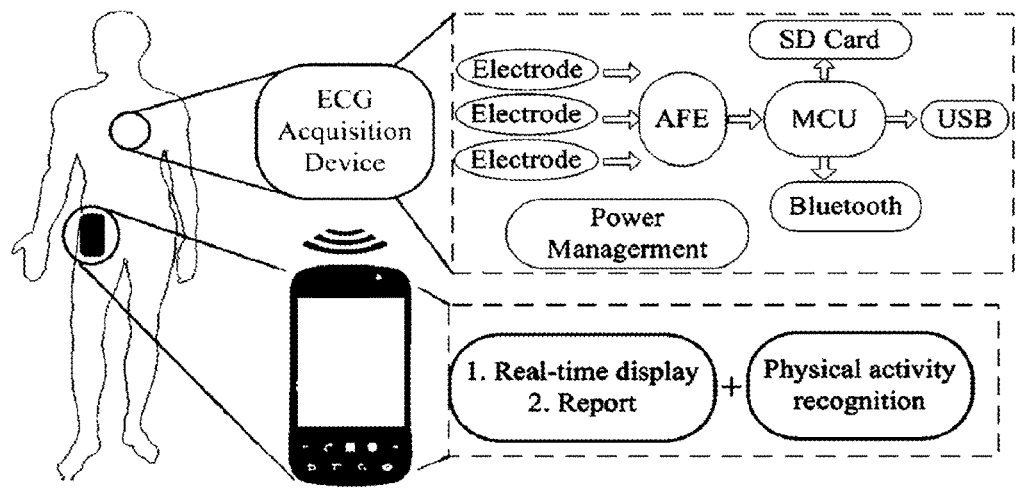
FIG. 14 shows a prior art ECG analog acquisition and wireless transmitter system.
Figure 15:
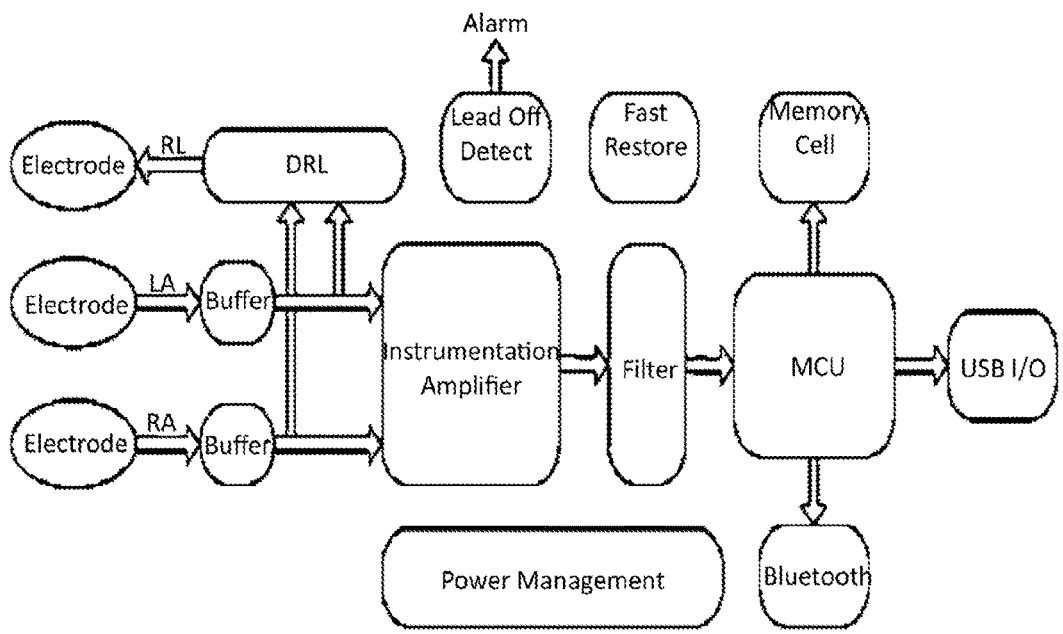
FIGS. 15 and 16 show semi-schematic drawings of the prior art ECG wireless transmitter system and ECG analog acquisition system of FIG. 14.
Figure 16:
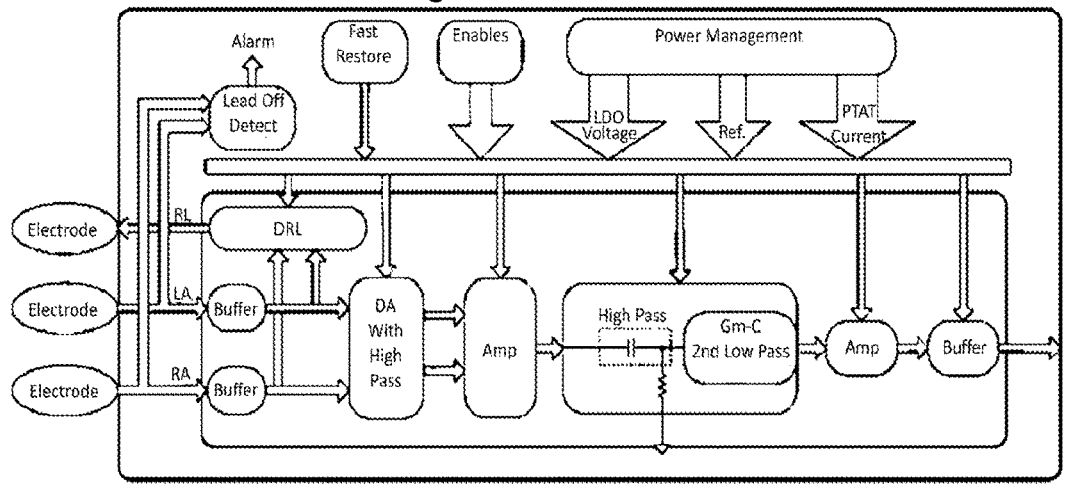

FIGS. 14, 15 and 16 show aspects of a prior art ECG analog acquisition and wireless transmitter system, See, Fen Miao, Yayu Cheng, Yi He, Qingyun He and Ye Li, "A Wearable Context-Aware ECG Monitoring System Integrated with Built-in Kinematic Sensors of the Smartphone", Sensors 2015, 15(5), 11465-11484; doi:10.3390/s150511465, www.mdpi.com/1424-8220/15/5/11465/htm, which is expressly incorporated herein by reference. In its entirety.

The block diagram of a proposed ECG monitoring system combined a wearable ECG acquisition sensor with a smartphone is shown in FIG. 14. The ECG sensor follows the YY1139-2000 standard (a pharmaceutical industry standard of China for single and multichannel electrodigraph, which is evolved from EC13 national standard). In the ECG acquisition sensor, signal is amplified and filtered by a single chip of AFE module, then in MCU module the analog signal from AFE is converted to digital signal. After processed with compression algorithm, the digital signal is recorded in SD card or transmitted to smartphone for real-time display. Meanwhile, a USB port is equipped in the device for transmitting the signals which have been saved in the SD card to personal computers and then to the cloud platform for further analysis. The ECG signals transmitted to smartphone are real-time displayed on screen, with a brief report provided from the automatic analysis approach in the software or professional advices provided from the remote server. The built-in kinematic sensors of the smartphone are used to recognize the individual's physical activity and thus help to improve the diagnosis accuracy for detecting abnormal patterns.

The block diagram of traditional implementation of ECG acquisition device is presented in FIG. 15, in which the circuit consists of a traditional instrument amplifier and Sallen-Key or Nyquist low pass filter, and some external function circuits for realistic ECG detection. The system employs various discrete components which occupy circuit board area.

Miao et al. propose an architecture using a fully custom, fully integrated, low power AFE, with all the function circuits integrated, as shown in FIG. 16 of the prior art, with an input/output buffer, full differential amplifier (DA) with high pass function, second Gm-C low pass filter, additional amplifying stage, DRL circuit, lead-off detecting circuit, fast restore function, and a power management module to provide a stable working voltage and current.

Figure 17:
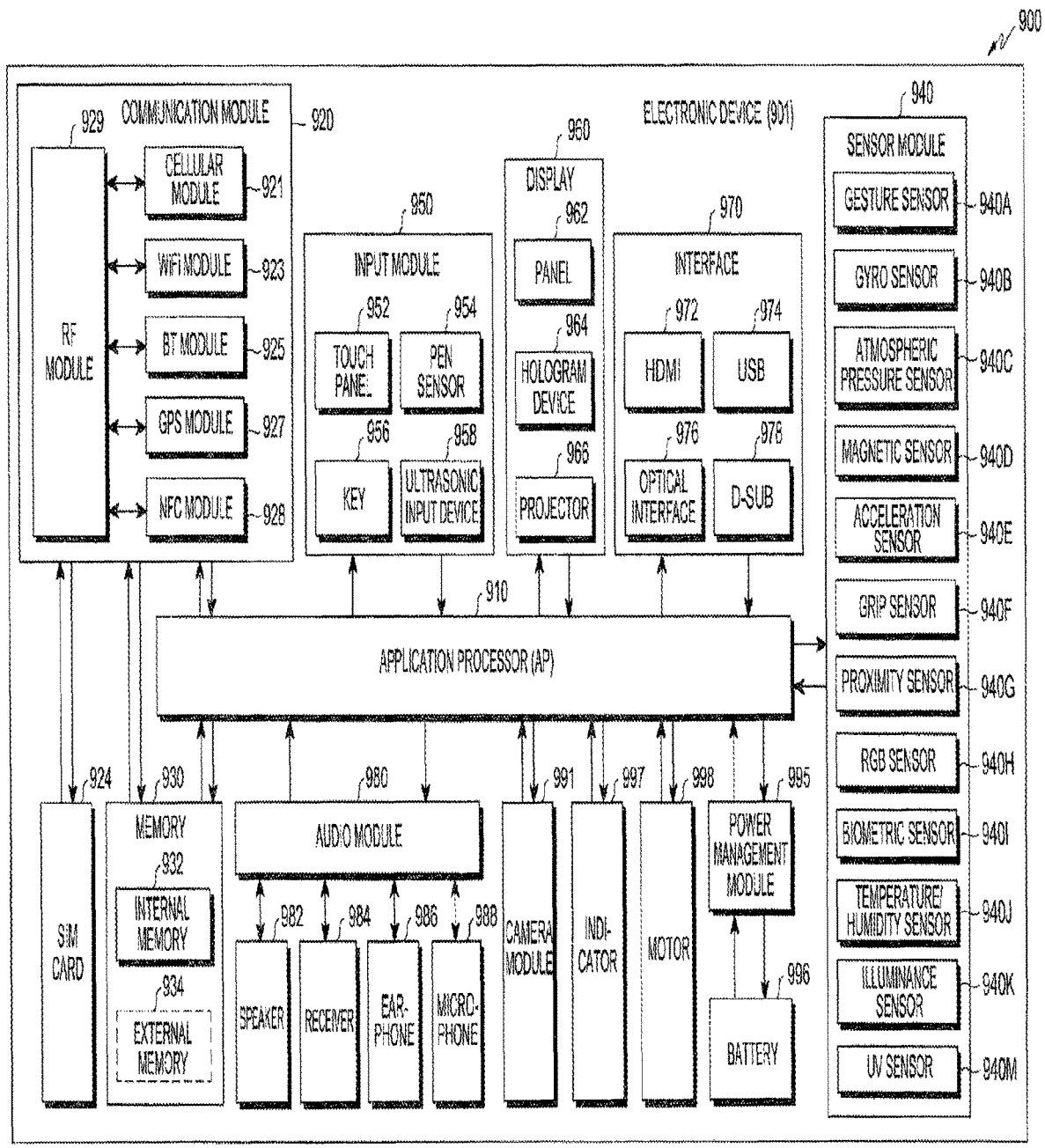
FIG. 17 shows a prior art flow diagram for algorithm implementation of the prior art ECG analog acquisition and wireless transmitter system according to FIG. 14.
Figure 18:
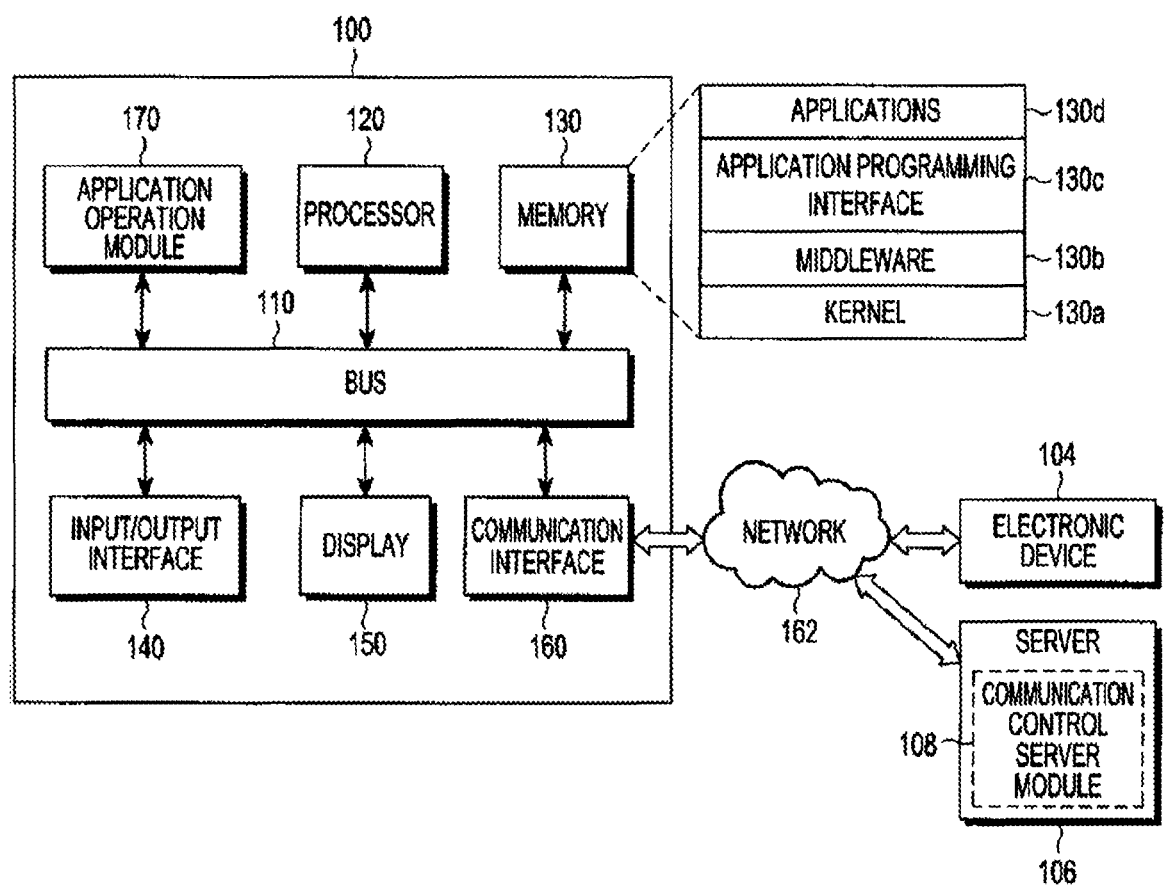
FIG. 18 shows a block diagram of a prior art electronic device according to US 2016/0128209.

US 2016/0128209, expressly incorporated herein by reference in its entirety, discloses an exemplary hardware platform that can be used to implement the present technology, as shown in FIGS. 17 and 18.

Referring to FIG. 17 of US 2016/0128209, the electronic device 100 can constitute at least one of: at least one AP (application processor) 910, a communication module 920, a SIM (subscriber identification module) card 924, a memory 930, a sensor module 940, an input device 950, a display 960 (e.g. the display device 13), an interface 970, an audio module 980, a camera module 991, a power management module 995, a battery 996, an indicator 997, and a motor 998. The AP 910 controls a plurality of hardware or software components connected to the AP 910 by driving an operating system or an application program, process various data including multimedia data, and perform calculations. The AP 910 can be embodied as, for example, a System on Chip (SoC). According to an embodiment, the AP 910 further includes a Graphic Processing Unit (GPU). The communication module 920 (e.g. the communication interface 160) can perform data transmission/reception in connection with communication with other electronic devices connected to the electronic device 100 via a network. According to one embodiment, the communication module 920 includes at least one of: a cellular module 921, a Wi-Fi module 923, a BT module 925, a GPS module 927, an NFC module 928, and a Radio Frequency (RF) module 929. The cellular module 921 provides a voice call, a video call, a text message service, or an Internet service through a communication network (for example, LTE, LTE-A, CDMA, WCDMA, UMTS, WiMax, GSM, 3G, 4G, 5G, or the like). Further, the cellular module 921 distinguishes and authenticates electronic devices within a communication network by using a subscriber identification module (for example, the SIM card 924). According to an embodiment, the cellular module 921 performs at least some of functions that the AP 910 provides. For example, the cellular module 921 can perform at least a part of a multimedia control function.

The cellular module 921 may include a Communication Processor (CP). Further, the cellular module 921 can be implemented by, for example, an SoC. Although components such as the cellular module 921 (e.g., the communication processor), the memory 930, or the power management module 995 are illustrated to be separate from the AP 910 in FIG. 17, the AP 910 can be implemented to include at least some of the above described components (e.g., the cellular module 921). The AP 910 or the cellular module 921 (for example, communication processor) can load a command or data received from at least one of a non-volatile memory and other components connected to each of them to a volatile memory and process the loaded command or data. Further, the AP 910 or the cellular module 921 can store data received from or generated by at least one of the other components in a non-volatile memory.

Each of the Wi-Fi module 923, the BT module 925, the GPS module 927, and the NFC module 928 can include, for example, a processor for processing data transmitted/received through the corresponding module. In FIG. 17, the cellular module 921, the WiFi module 923, the BT module 925, the GPS module 927, and the NFC module 928 are illustrated as blocks separated from each other, but, according to an embodiment, at least some (for example, two or more) of the cellular module 921, the WiFi module 923, the BT module 925, the GPS module 927, and the NFC module 928 can be included in one Integrated Chip (IC) or one IC package. For example, at least some (for example, a communication processor corresponding to the cellular module 921 and a Wi-Fi processor corresponding to the Wi-Fi module 923) of the processors corresponding to the cellular module 921, the Wi-Fi module 923, the BT module 925, the GPS module 927, and the NFC module 928, respectively, can be implemented by a single SoC.

The RF module 929 transmits and receives data, for example, an RF signal. Although not illustrated, the RF module 929 includes, for example, a transceiver, a Power Amplifier Module (PAM), a frequency filter, a Low Noise Amplifier (LNA), or the like. Further, the RF module 929 further includes a component for transmitting/receiving an electromagnetic wave in a free space during a radio communication, such as a conductor or a conducting wire. Although the cellular module 921, the Wi-Fi module 923, the BT module 925, the GPS module 927, and the NFC module 928 are illustrated to share one RF module 929 in FIG. 17, at least one of the cellular module 921, the Wi-Fi module 923, the BT module 925, the GPS module 927, and the NFC module 928 transmits and receives RF signals through a separate RF module.

The SIM card 924 is a card including a subscriber identification module, and can be inserted into a slot formed in a particular portion of the electronic device. The SIM card 924 includes unique identification information (for example, Integrated Circuit Card Identifier (ICCID)) or subscriber information (for example, International Mobile Subscriber Identity (IMSI)).

The memory 930 (for example, memory 130) includes an internal memory 932 or an external memory 934. The internal memory 932 includes at least one of a volatile memory (for example, a Dynamic RAM (DRAM), a Static RAM (SRAM), a Synchronous Dynamic RAM (SDRAM), and the like) and a non-volatile memory (for example, a One Time Programmable ROM (OTPROM), a Programmable ROM (PROM), an Erasable and Programmable ROM (EPROM), an Electrically Erasable and Programmable ROM (EEPROM), a mask ROM, a flash ROM, a NAND flash memory, a NOR flash memory, and the like).

According to an embodiment, the internal memory 932 is a Solid State Drive (SSD). The external memory 934 can further include a flash drive, for example, a Compact Flash (CF), a Secure Digital (SD), a Micro Secure Digital (Micro-SD), a Mini Secure Digital (Mini-SD), an extreme Digital (xD), a memory stick or the like. The external memory 934 can be functionally connected to the electronic device 100 through various interfaces. According to an embodiment, the electronic device 100 further includes a storage device (or storage medium) such as a hard drive.

The sensor module 940 measures a physical quantity or detects an operation state of the electronic device 100, and converts the measured or detected information to an electronic signal. The sensor module 940 includes, for example, at least one of a gesture sensor 940A, a gyro sensor 940B, an atmospheric pressure sensor 940C, a magnetic sensor 940D, an acceleration sensor 940E, a grip sensor 940F, a proximity sensor 940G, a color sensor 940H (for example, red, green, and blue (RGB) sensor), a biometric sensor 940I, a temperature/humidity sensor 940J, a luminance sensor 940K, and an Ultra Violet (UV) sensor 940M. Additionally or alternatively, the sensor module 940 includes, for example, an E-nose sensor (not illustrated), an ElectroMyo-Graphy (EMG) sensor (not illustrated), an ElectroEncephaloGram (EEG) sensor (not illustrated), an ElectroCardioGram (ECG) sensor (not illustrated), an InfraRed (IR) sensor, an iris sensor (not illustrated), a fingerprint sensor (not illustrated) and the like. The sensor module 940 further includes a control circuit for controlling one or more sensors included therein.

The input device 950 includes a touch panel 952, a (digital) pen sensor 954, a key 956, or an ultrasonic input device 958. The touch panel 952 recognizes a touch input through at least one of, for example, a capacitive scheme, a resistive scheme, an infrared scheme, and an ultrasonic scheme. The touch panel 952 further includes a control circuit. The capacitive scheme touch panel recognizes physical contact or proximity. The touch panel 952 further includes a tactile layer. In this case, the touch panel 952 provides a tactile reaction to a user.

The (digital) pen sensor 954 can be embodied, for example, using a method identical or similar to a method of receiving a touch input of a user, or using a separate recognition sheet. The key 956 includes, for example, a physical button, an optical key or a keypad. The ultrasonic input device 958 has an input tool, which generates ultrasonic signals, so that the electronic device 100 senses sound waves using the microphone 988 and identifies data, and is capable of wireless recognition. According to an embodiment, the electronic device 100 receives a user input from an external device (for example, computer or server) connected thereto by using the communication module 920.

The display 960 (e.g. the display device 13) includes a panel 962, a hologram device 964, or a projector 966. The panel 962 can be, for example, a Liquid Crystal Display (LCD), Active-Matrix Organic Light Emitting Diode (AM-OLED), or the like. The panel 962 can be embodied to be, for example, flexible, transparent, or wearable. The panel 962 can be also configured as one module together with the touch panel 952. The hologram 964 can show a stereoscopic image in the air by using interference of light. The projector 966 can project light onto a screen to display an image. For example, the screen can be located inside or outside the electronic device 100. According to one embodiment, the display 960 can further include a control circuit for controlling the panel 962, the hologram device 964, or the projector 966.

The interface 970 includes, for example, a High-Definition Multimedia Interface (HDMI) 972, a Universal Serial Bus (USB) 974, an optical interface 976, or a D-subminiature (D-sub) 978. Additionally or alternatively, the interface 970 includes, for example, a Mobile High-definition Link (MHL) interface, a Secure Digital (SD) card/Multi-Media Card (MMC) interface, or an Infrared Data Association (IrDA) standard interface.

The audio module 980 bi-directionally converts a sound and an electronic signal. At least some of the components of the audio module 980 can be included in the input/output interface. The audio module 980 processes voice information input or output through, for example, a speaker 982, a receiver 984, earphones 986, the microphone 988 or the like.

The camera module 991 is a device which can photograph an image and a dynamic image. According to an embodiment, the camera module 291 includes one or more image sensors (for example, a front sensor or a back sensor), a lens (not shown), an Image Signal Processor (ISP) (not shown) or a flash (not shown) (for example, LED or xenon lamp).

The power management module 995 manages power of the electronic device 100. Although not illustrated, the power management module 995 includes, for example, a Power Management Integrated Circuit (PMIC), a charger Integrated Circuit (IC), or a battery or fuel gauge. The PMIC can be mounted to, for example, an integrated circuit or an SoC semiconductor. Charging methods can be classified into a wired charging method and a wireless charging method. The charger IC charges a battery and prevents over voltage or over current from being flowed from a charger. According to an embodiment, the charger IC includes a charger IC for at least one of the wired charging method and the wireless charging method. A magnetic resonance scheme, a magnetic induction scheme, or an electromagnetic scheme can be exemplified as the wireless charging method, and an additional circuit for wireless charging, such as a coil loop circuit, a resonance circuit, a rectifier circuit, and the like can be added. The battery fuel gauge measures, for example, a remaining quantity of the battery 996, or a voltage, a current, or a temperature during the charging. The battery 996 stores or generates electricity, and supplies power to the electronic device 100 using the stored or generated electricity. The battery 996 can include, for example, a rechargeable battery or a solar battery.

The indicator 997 indicates particular states (e.g., a booting state, a message state, a charging state, etc.) of the electronic device 100 or a part (e.g., the AP 910) of the electronic device 900. The motor 998 converts an electrical signal to a mechanical vibration. Although not illustrated, the electronic device 100 includes a processing unit (for example, GPU) for mobile TV support. The processing unit for supporting the mobile TV processes media data according to a standard of Digital Multimedia Broadcasting (DMB), Digital Video Broadcasting (DVB), media flow or the like.

The above described components of the electronic device according to various embodiments of the present disclosure can be formed of one or more components, and a name of a corresponding component element may be changed based on the type of electronic device. The electronic device according to the present disclosure may include one or more of the aforementioned components or may further include other additional components, or some of the aforementioned components may be omitted. Further, some of the components of the electronic device according to the various embodiments of the present disclosure may be combined to form a single entity, and thus, may equivalently execute functions of the corresponding elements prior to the combination.

The "module" used in various embodiments of the present disclosure may refer to, for example, a "unit" including one of hardware, software, and firmware, or a combination of two or more of the hardware, software, and firmware. The "module" may be interchangeable with a term, such as a unit, a set of logic, e.g., embodied in a non-transitory computer readable medium, a logical block, a component, or a circuit. The "module" may be a minimum unit of an integrated component element or a part thereof. The "module" may be a minimum unit for performing one or more functions or a part thereof. The "module" may be mechanically or electronically implemented. For example, the "module" according to various embodiments of the present disclosure may include at least one of an Application-Specific Integrated Circuit (ASIC) chip, a Field-Programmable Gate Arrays (FPGAs), and a programmable-logic device for performing operations which have been known or are to be developed hereafter.

FIG. 18 of US 2016/0128209 is a diagram illustrating a network environment including an electronic device 100 which includes a bus 110, a processor 120, a memory 130, an input/output interface 140, a display 150, a communication interface 160, and an application operation module 170. The bus 110 is a circuit that connects the above-described components with each other and to transfer communication (for example, control messages) between the above-described components. For example, the processor 120 can receive instructions from the aforementioned other elements (e.g., the memory 130, the input/output interface 140, the display 150, the communication interface 160, and the application operation module 170) through the bus 110, decipher the received instructions, and perform calculation or data processing according to the deciphered instructions.

The memory 130 stores instructions or data received from the processor 120 or other elements (e.g., the input/output interface 140, the display 150, the communication interface 160, the application operation module 170, or the like) or generated by the processor 120 or other elements. The memory 130 includes programming modules, such as a kernel 130a, middleware 130b, API (application programming interface) 130c, or an application 130d. Each of the programming modules described above can be formed of software, firmware, and hardware, or a combination thereof.

The kernel 130a controls or manage system resources (for example, the bus 110, the processor 120, the memory 130 or the like) which are used for performing operations or functions implemented by other programming modules, for example, the middleware 130b, the API 130c or the application 130d. Further, the kernel 130a provides an interface through which the middleware 130b, the API 130c, or the application 130d can access and control or manage individual components of the electronic device 100.

The middleware 130b serves as an intermediator that allows the API 130c or the application 130d to communicate with and exchange data with the kernel 130a. Further, in relation to requests for an operation received from the application 130d, the middleware 130b controls (for example, scheduling or load-balancing) the requests for the operation by using, for example, a method of determining sequence for using system resources (for example, the bus 110, the processor 120, the memory 130, or the like) of the electronic device 100 with respect to at least one application among the applications 130d.

The API 130c is an interface by which the application 130d controls functions provided from the kernel 130a or the middleware 130b, and includes, for example, at least one interface or function (for example, instructions) for file control, window control, image processing, or text control.

According to various embodiments, the application 130d includes a Short Message Service (SMS)/Multimedia Message Service (MMS) application, an e-mail application, a calendar application, an alarm application, a health care application (for example, an application for measuring the amount of exercise or blood sugar), an environmental information application (for example, an application for providing atmospheric pressure, humidity, or temperature), or the like. Additionally or alternatively, the application 130d can be an application related to information exchange between the electronic device 100 and an external electronic device 104. The application related to the information exchange can include, for example, a notification relay application for transmitting specific information to the external electronic device, or a device management application for managing the external electronic device.

For example, the notification relay application can include a function of transferring notification information generated in other applications (for example, the SMS/MMS application, the e-mail application, the health care application, or the environmental information application) of the electronic device 100 to the external electronic device 104. Additionally or alternatively, the notification relay application can receive the notification information from, for example, the external electronic device 104, and can provide the received notification information to a user. The device management application manages (for example, install, delete, or update), for example, at least some functions (for example, turning external electronic device (or some elements) on or off, or adjusting the brightness (or resolution) of a display) of the external electronic device 104 that communicates with the electronic device 100, applications performed in the external electronic device, or services (for example, a phone call service, or a messaging service) provided by the external electronic device.

According to various embodiments, the application 130d includes applications, which are designated according to the attribute (e.g., device type) of the external electronic device 104. For example, in a case where the external electronic device is an MP3 player, the application 130d includes an application related to the reproduction of music. Similarly, when the external electronic device is a mobile medical device, the application 130d includes an application related to health care. According to an embodiment, the application 130d includes at least one of an application designated for the electronic device 100 or an application received from a different electronic device (for example, a server 106, or an external electronic device 104).

The input/output interface 140 transmits a command or data input from the user through an input/output device (for example, sensor, keyboard, or touch screen) to the processor 120, the memory 130, the communication interface 160, or the application operation module 170 through, for example, the bus 110. For example, the input/output interface 140 provides, to the processor 120, data for a user's touch which is input through the touch screen. Further, through the input/output device (for example, a speaker or a display), the input/output interface 140 outputs commands or data received from the processor 120, the memory 130, the communication interface 160, or the application operation module 170 through the bus 110. For example, the input/output interface 140 outputs voice data processed by the processor 120 to the user through the speaker.

The display 150 displays various pieces of information (for example, multimedia data or text data) for the user.

The communication interface 160 makes a communication connection between the electronic device 100 and a different electronic device (for example, the external electronic device 104 or the server 106). For example, the communication interface 160 connects to a network 162 through wireless or wired communication to communicate with the external electronic device. The wireless communication includes, for example, at least one of Wi-Fi, Wi-Fi Direct, Bluetooth (BT), Near Field Communication (NFC), a Global Positioning System (GPS), or cellular communication (for example, LTE, LTE-A, CDMA, WCDMA, UMTS, WiMax, GSM, 3G, 4G, 5G, etc.). The wired communication includes at least one of, for example, a Universal Serial Bus (USB, USB 2.0, USB 3.0, USB 3.1, etc.), a High Definition Multimedia Interface (HDMI), Ethernet (802.3, etc.), Recommended Standard 232 (RS-232), and a Plain Old Telephone Service (POTS) port/interface.

According to an embodiment, the network 162 can be a telecommunications network. The communication network can include at least one of a computer network, the Internet, the Internet of things, and a telephone network. According to an embodiment, protocols (for example, a transport layer protocol, a data link layer protocol, or a physical layer protocol) for communication between the electronic device 100 and external electronic devices can be supported by at least one of the application 130*d*, the API 130*c*, the middleware 130*b*, the kernel 130*a*, and the communication interface 160.

According to an embodiment, the application operation module 170 supports driving of the electronic device 100 by performing at least one of the operations (or functions) implemented by the electronic device 100. For example, the server 106 can include a communication control server module 108 capable of supporting the application operation module 170 implemented in the electronic device 100. For example, the communication control server module 108 can include at least one component of the application operation module 170, and can perform (e.g., perform as a proxy) at least one of the operations performed by the application operation module 170.

The application operation module 170 processes at least some of the information obtained from other components (for example, the processor 120, the memory 130, the input/output interface 140, or the communication interface 160) and utilize the same in various manners. For example, the application operation module 170 controls at least some functions of the electronic device 100 by using the processor 120 or independently thereof so that the electronic device 100 can interwork with a different electronic device (e.g., the external electronic device 104 or the server 106). The connection control module 170 can be integrated into the processor 120. According to an embodiment, at least one component of the application operation module 170 can be included in the server 106 (for example, the communication control server module 108) and can have at least one operation, which is performed by the application operation module 170, supported by the server 106.

Although the present disclosure has been described with an exemplary embodiment, various changes and modifications may be suggested to one skilled in the art. It is intended that the present disclosure encompass such changes and modifications as fall within the scope of the appended claims.

What is claimed is:

REFERENCES

Each reference cited herein (including those aforementioned) is expressly incorporated herein by reference in its entirety.

Aiba, I., Noebels, J. L., 2015. Spreading depolarization in the brainstem mediates sudden cardiorespiratory arrest in mouse SUDEP models. Sci Transl Med 7, 282ra246.

Amir, J., Ashkenazi, S., Schonfeld, T., Weitz, R., Nitzan, M., 1983. Laryngospasm as a single manifestation of epilepsy. Arch Dis Child 58, 151-153.

Antonia, S. A., Oliva, L. V., Bruck, I., Malucelli, M., Yabumoto, S., Castellano, J. L., 2001.

Sudden unexpected, unexplained death in epilepsy autopsied patients. Arq Neuropsiquiatr 59, 40-45.

Arito, H., Takahashi, M., Iwasaki, T., Uchiyama, I., 1997. Age-related changes in ventilatory and heart rate responses to acute ozone exposure in the conscious rat. Ind Health 35, 78-86.

Bartlett, D., 2011. Upper Airway Motor Systems, Comprehensive Physiology. John Wiley & Sons, Inc.

Bateman, L. M., Li, C. S., Seyal, M., 2008. Ictal hypoxemia in localization-related epilepsy: analysis of incidence, severity and risk factors. Brain 131, 3239-3245.

Bermeo-Ovalle, A. C., Kennedy, J. D., Schuele, S. U., 2015. Cardiac and autonomic mechanisms contributing to SUDEP. J Clin Neurophysiol 32, 21-29.

Bernard, C., 2015. Spreading depression: epilepsy's wave of death. Sci Transl Med 7, 282fs214. Blitzer, A., Meyer, T., 2006. Neurologic disorders of the larynx, in: Bailey, B. J., Johnson, J. T., Newlands, S. D. (Eds.), Head & Neck Surgery—otolaryngology Lippincott Williams & Wilkins, pp. 867-882.

Blum, A. S., 2009. Respiratory physiology of seizures. J Clin Neurophysiol 26, 309-315.

Brancatisano, A., Dodd, D. S., Engel, L. A., 1991. Posterior cricoarytenoid activity and glottic size during hyperpnea in humans. J Appl Physiol (1985) 71, 977-982.

Brostrom, A., Johansson, P., Stromberg, A., Albers, J., Martensson, J., Svanborg, E., 2007. Obstructive sleep apnoea syndrome—patients' perceptions of their sleep and its effects on their life situation. J Adv Nurs 57, 318-327.

Canteras, N. S., Swanson, L. W., 1992. Projections of the ventral subiculum to the amygdala, septum, and hypothalamus: a PHAL anterograde tract-tracing study in the rat. J Comp Neurol 324, 180-194.

Devinsky, O., 2011. Sudden, unexpected death in epilepsy. N Engl J Med 365, 1801-1811.

Donzelli, J., Brady, S., 2004. The effects of breath-holding on vocal fold adduction: implications for safe swallowing. Arch Otolaryngol Head Neck Surg 130, 208-210.

Ead, H., 2003. Review of laryngospasm and noncardiogenic pulmonary edema. Dynamics 14, 9-12.

Faingold, C. L., Randall, M., Tupal, S., 2010. DBA/1 mice exhibit chronic susceptibility to audiogenic seizures followed by sudden death associated with respiratory arrest. Epilepsy Behav 17, 436-440.

Geerling, J. C., Shin, J. W., Chimenti, P. C., Loewy, A. D., 2010. Paraventricular hypothalamic nucleus: axonal projections to the brainstem. J Comp Neurol 518, 1460-1499.

Greene, E. C., 1968. Anatomy of the rat. Hafner Pub. Co., New York.

Herreras, O., Largo, C., Ibarz, J. M., Somjen, G. G., Martin del Rio, R., 1994. Role of neuronal synchronizing mechanisms in the propagation of spreading depression in the in vivo hippocampus. J Neurosci 14, 7087-7098.

Hotta, H., Koizumi, K., Stewart, M., 2009. Cardiac sympathetic nerve activity during kainic acid-induced limbic cortical seizures in rats. Epilepsia 50, 923-927.

Johnston, S. C., Horn, J. K., Valente, J., Simon, R. P., 1995. The role of hypoventilation in a sheep model of epileptic sudden death. Ann Neurol 37, 531-537.

Johnston, S. C., Siedenberg, R., Min, J. K., Jerome, E. H., Laxer, K. D., 1997. Central apnea and acute cardiac ischemia in a sheep model of epileptic sudden death. Ann Neurol 42, 588-594.

Kuna, S. T., Day, R. A., Insalaco, G., Villeponteaux, R. D., 1991. Posterior cricoarytenoid activity in normal adults during involuntary and voluntary hyperventilation. J Appl Physiol (1985) 70, 1377-1385.

Kuna, S. T., Insalaco, G., Woodson, G. E., 1988. Thyroarytenoid muscle activity during wakefulness and sleep in normal adults. J Appl Physiol (1985) 65, 1332-1339.

Kuna, S. T., Smickley, J. S., Insalaco, G., 1990. Posterior cricoarytenoid muscle activity during wakefulness and sleep in normal adults. J Appl Physiol (1985) 68, 1746-1754.

Langan, Y., 2000. Sudden unexpected death in epilepsy (SUDEP): risk factors and case control studies. Seizure 9, 179-183.

Lathers, C. M., Schraeder, P. L., Boggs, J. G., 1998. Sudden unexplained death and autonomic dysfunction., in: Engel, J., Pedley, T. A. (Eds.), Epilepsy: a comprehensive textbook. Lippincott-Raven, Philadelphia, pp. 1943-1955, chapter 1183.

Lathers, C. M., Schraeder, P. L., Bungo, M. W., 2008. The mystery of sudden death: mechanisms for risks. Epilepsy Behav 12, 3-24.

Lauritzen, M., Dreier, J. P., Fabricius, M., Hartings, J. A., Graf, R., Strong, A J., 2011. Clinical relevance of cortical spreading depression in neurological disorders: migraine, malignant stroke, subarachnoid and intracranial hemorrhage, and traumatic brain injury. J Cereb Blood Flow Metab 31, 17-35.

Leaming, J. M., Temdrup, T. E., Ognibene, 5., 1999. Glottal patency during experimental cortical seizures in piglets. Acad Emerg Med 6, 682-687.

Leao, A. A., 1986. Spreading depression. Funct Neurol 1, 363-366.

Mascareno, E., Galatioto, J., Rozenberg, I., Salciccioli, L., Kamran, H., Lazar, J. M., Liu, F., Pedrazzini, T., Siddiqui, M. A., 2012. Cardiac lineage protein-1 (CLP-1) regulates cardiac remodeling via transcriptional modulation of diverse hypertrophic and fibrotic responses and angiotensin II-transforming growth factor beta (TGF-beta1) signaling axis. J Biol Chem 287, 13084-13093.

Massey, C. A., Sowers, L. P., Dlouhy, B. J., Richerson, G. B., 2014. Mechanisms of sudden unexpected death in epilepsy: the pathway to prevention. Nat Rev Neurol 10, 271-282.

Mendelsohn, M. S., Martin, R. E., 1993. Airway protection during breath-holding. The Annals of otology, rhinology, and laryngology 102, 941-944.

Miller, W. F., Scacci, R., Gast, L. R., 1987. Laboratory evaluation of pulmonary function. Lippincott, Philadelphia.

Mor, N., Naggar, I., Das, O., Nakase, K., Silverman, J. B., Sundaram, K., Stewart, M., Kollmar, R., 2014. Quantitative video laryngoscopy to monitor recovery from recurrent laryngeal nerve injury in the rat. Otolaryngology—head and neck surgery: official journal of American Academy of Otolaryngology-Head and Neck Surgery 150, 824-826.

Morentin, B., Alcaraz, R., 2002. [Sudden unexpected death in epilepsy in children and adolescents]. Rev Neurol 34, 462-465.

Murray-Calderon, P., Connolly, M. A., 1997. Laryngospasm and noncardiogenic pulmonary edema. Journal of perianesthesia nursing: official journal of the American Society of PeriAnesthesia Nurses/American Society of PeriAnesthesia Nurses 12, 89-94.

Naggar, I., Stewart, M., 2015. A rat model for exploring the contributions of ventricular arrhythmias to sudden death in epilepsy, in: Lathers, C. M., Schraeder, P. L., Leestma, J. E., Wannamaker, B. B., Richard L. Verrier, F. A. C. C., Schachter, S. C. (Eds.), Sudden Unexpected Death in Epilepsy: Mechanisms and New Methods for Analyzing Risks. Taylor & Francis, pp. 241-250.

Naggar, I., Uchida, S., Kamran, H., Lazar, J., Stewart, M., 2012. Autonomic boundary conditions for ventricular fibrillation and their implications for a novel defibrillation technique. J Physiol Sci 62, 479-492.

Nei, M., Hays, R., 2010. Sudden unexpected death in epilepsy. Curr Neurol Neurosci Rep 10, 319-326.

Paxinos, G., Watson, C., 1998. The rat brain in stereotaxic coordinates, 4th ed. Academic Press, San Diego.

Renninger, J. P., 2006. Head-out plethysmography in safety pharmacology assessment. Curr Protoc Pharmacol Chapter 10, Unit10 11.

Ryvlin, P., Nashef, L., Lhatoo, S. D., Bateman, L. M., Bird, J., Bleasel, A., Boon, P., Crespel, A., Dworetzky, B. A., Hogenhaven, H., Lerche, H., Maillard, L, Maker, M. P., Marchal, C., Murthy, J. M., Nitsche, M., Pataraia, E., Rabben, T., Rheims, S., Sadzot, B., Schulze-Bonhage, A., Seyal, M., So, E. L., Spitz, M., Szucs, A., Tan, M., Tao, J. X., Tomson, T., 2013. Incidence and mechanisms of cardiorespiratory arrests in epilepsy monitoring units (MORTEMUS): a retrospective study. Lancet Neurol 12, 966-977.

Saito, T., Sakamoto, K., Koizumi, K., Stewart, M., 2006. Repeatable focal seizure suppression: a rat preparation to study consequences of seizure activity based on urethane anesthesia and reversible carotid artery occlusion. J Neurosci Methods 155, 241-250.

Sakamoto, K., Saito, T., Orman, R., Koizumi, K., Lazar, J., Salciccioli, L., Stewart, M., 2008. Autonomic consequences of kainic acid-induced limbic cortical seizures in rats: peripheral autonomic nerve activity, acute cardiovascular changes, and death. Epilepsia 49, 982-996.

Salmo, E. N., Connolly, C. E., 2002. Mortality in epilepsy in the west of Ireland: a 10-year review. Ir J Med Sci 171, 199-201.

Schraeder, P. L., Lathers, C. M., 1983. Cardiac neural discharge and epileptogenic activity in the cat: an animal model for unexplained death. Life Sci 32, 1371-1382.

Seyal, M., Bateman, L. M., Albertson, T. E., Lin, T. C., Li, C. S., 2010. Respiratory changes with seizures in localization-related epilepsy: Analysis of periictal hypercapnia and airflow patterns. Epilepsia.

Shorvon, S., Tomson, T., 2011. Sudden unexpected death in epilepsy. Lancet 378, 2028-2038. Somjen, G. G., Aitken, P. G., Czeh, G. L., Herreras, O., Jing, J., Young, J. N., 1992. Mechanism of spreading depression: a review of recent findings and a hypothesis. Can J Physiol Pharmacol 70 Suppl, S248-254.

Sowers, L. P., Massey, C. A., Gehlbach, B. K., Granner, M. A., Richerson, G. B., 2013. Sudden unexpected death in epilepsy: fatal post-ictal respiratory and arousal mechanisms. Respiratory physiology & neurobiology 189, 315-323.

Stewart, M., 2008. Is an abrupt "cerebral electrical shutdown" during a seizure the mechanism of SUDEP?, J Neural Neurosurg Psychiatry, eLetter: jnnp.bmj.com/cgi/eletters/78/12/1395#3299, 1312 February 2008.

Stewart, M., 2011. The urethane/kainate seizure model as a tool to explore physiology and death associated with seizures, in: Lathers, C. M., Schraeder, P. L., Bungo, M. W., Leetsma, J. E. (Eds.), Sudden Death in Epilepsy: Forensic and Clinical Issues. Taylor & Francis Group, Boca Raton, FL, pp. 627-644.

Surges, R., Sander, J. W., 2012. Sudden unexpected death in epilepsy: mechanisms, prevalence, and prevention. Curr Opin Neurol 25, 201-207.

Tavee, J., Morris, H., 3rd, 2008. Severe postictal laryngospasm as a potential mechanism for sudden unexpected death in epilepsy: a near-miss in an EMU. Epilepsia 49, 2113-2117.

Terndrup, T. E., Gregory, M. E., Fordyce, W. E., 1995a. The role of the upper airway in contributing to respiratory responses during experimental seizures in piglets. Pediatr Res 38, 61-66.

Terndrup, T. E., Kadison, A., Woo, P., 1995b. Glottal patency during experimental seizures in piglets. Pediatr Res 38, 932-937.

Thurman, D. J., Hesdorffer, D. C., French, J. A., 2014. Sudden unexpected death in epilepsy: assessing the public health burden. Epilepsia 55, 1479-1485.

Tolstykh, G. P., Cavazos, J. E., 2013. Potential mechanisms of sudden unexpected death in epilepsy. Epilepsy Behav 26, 410-414.

Umbrain, V., Camu, F., 1993. Acute pulmonary edema after laryngospasm. Acta anaesthesiologica Belgica 44, 149-153.

Uteshev, V. V., Tupal, S., Mhaskar, Y., Faingold, C. L., 2010. Abnormal serotonin receptor expression in DBA/2 mice associated with susceptibility to sudden death due to respiratory arrest Epilepsy Res 88, 183-188.

Venit, E. L., Shepard, B. D., Seyfried, T. N., 2004. Oxygenation Prevents Sudden Death in Seizure-prone Mice. Epilepsia 45, 993-996.

Wannamaker, B. B., 1985. Autonomic nervous system and epilepsy. Epilepsia 26 Suppl 1, S31-39.

Weiss, J. W., Tamisier, R., Liu, Y., 2015. Sympathoexcitation and Arterial Hypertension Associated with Obstructive Sleep Apnea and Cyclic Intermittent Hypoxia. J Appl Physiol (1985), jap 00315 02015.

What is claimed is:

1. A method for detecting obstructive apnea, comprising:
receiving a transcutaneous composite bioelectric signal from a mammal comprising an electromyographic activity signal from muscles of inspiration of the mammal and components of one of an electrocardiographic signal from a heart of the mammal or an electroencephalographic signal from a brain of the mammal, with an amplifier;
quantifying an amplitude of the electromyographic activity signal from muscles of inspiration within the transcutaneous composite bioelectric with an electronic circuit configured to quantify the amplitude of the electromyographic activity signal from muscles of inspiration signal between at least 300 Hz to 1 kHz;
determining a timing of inspiratory efforts and an amplitude of inspiratory efforts based on the amplitude of the electromyographic activity signal from muscles of inspiration;
determining a baseline amplitude of inspiratory efforts during a period of non-obstructed respiration based on the amplitude of the electromyographic activity signal from muscles of inspiration;
comparing an amplitude of inspiratory efforts based on the amplitude of the electromyographic activity signal from muscles of inspiration with the determined baseline amplitude of inspiratory efforts; and
identifying a series of inspiratory efforts have an increasing amplitude of inspiratory efforts based on the amplitude of the electromyographic activity signal from muscles of inspiration over time, above the baseline amplitude of inspiratory efforts; and
determining an occurrence of an airway restriction or obstruction based on the identified series of inspiratory efforts that has an increasing amplitude of inspiratory efforts.

2. The method according to claim 1, further comprising determining a baseline timing range of inspiratory efforts during a period of non-obstructed respiration, and comparing the timing of inspiratory efforts with the determined baseline timing of inspiratory efforts, wherein the occurrence of the airway restriction or obstruction is determined if a series of inspiratory efforts have increasing amplitude of inspiratory efforts based on the amplitude of the electromyographic activity signal from muscles of inspiration above the baseline amplitude of inspiratory efforts over time, and a timing within the baseline timing range.

3. The method according to claim 1, wherein the bioelectric signal component is an electrocardiographic signal.

4. The method according to claim 3, wherein the timing and amplitude of inspiratory efforts based on the amplitude of the electromyographic activity signal from muscles of inspiration are determined over a series of at least three inspiratory efforts before the occurrence of an the airway restriction or obstruction is determined.

5. The method according to claim 1, wherein the bioelectric signal component is an electroencephalographic signal.

6. The method according to claim 1, wherein the transcutaneous composite bioelectric signal is acquired from a single extremity.

7. The method according to claim 1, further comprising generating an audible alarm in response to determining the occurrence of the airway restriction or obstruction.

8. The method according to claim 1, further comprising selectively wirelessly communicating a signal in response to determining the occurrence of the airway restriction or obstruction.

9. The method according to claim 1, wherein:
said receiving the transcutaneous composite bioelectric signal from the mammal comprising the electromyographic activity signal from muscles of inspiration comprises receiving at least one of an electrocardiographic signal and an electroencephalographic signal; and
said quantifying of the amplitude of the electromyographic activity signal from muscles of inspiration within the transcutaneous composite bioelectric signal also containing a bioelectric signal component comprising an electrocardiographic signal or an electroencephalographic signal comprises at least subjecting the transcutaneous composite bioelectric signal to a bandpass filter having a passband between about 300 Hz and 1 kHz.

10. The method according to claim 1, wherein said quantifying of the amplitude of the electromyographic activity signal from muscles of inspiration within the transcutaneous composite bioelectric signal also containing a bioelectric signal component comprising an electrocardiographic signal or an electroencephalographic signal comprises determining a signal power within a passband over time.

11. The method according to claim 1, wherein said comparing an amplitude of inspiratory efforts based on the amplitude of the electromyographic activity signal from muscles of inspiration with the determined baseline amplitude of inspiratory efforts comprises comparing a series of the amplitudes of inspiratory efforts and timings of inspiratory efforts with a baseline window representing a normal range of amplitudes of inspiratory efforts based on the amplitude of the electromyographic activity signal from muscles of inspiration and timings of inspiratory efforts.

12. The method according to claim 1, further comprising:
determining a baseline inter-heartbeat interval and a normal range of variation for a respective respiratory rate within a respiratory interval;
determining an inter-heartbeat interval and a respiratory rate of a patient;
determining a commencement of a series of at least one inter-heartbeat interval which is outside the normal range of variation, below the baseline inter-heartbeat interval, for the respective respiratory rate; and
determining commencement of the airway restriction or obstruction if within the respiratory interval, a number of commencements above a threshold, of the series of the at least one inter-heartbeat interval which is outside the normal range of variation, below the baseline inter-heartbeat interval for the respective respiratory rate.

13. The method according to claim 12, wherein the threshold is three.

14. The method according to claim 12, wherein the inter-heartbeat interval and the respiratory rate are determined based on the transcutaneous composite bioelectric signal.

15. The method according to claim 14, wherein the transcutaneous composite bioelectric signal comprises an electrocardiographic signal.

16. The method according to claim 15, wherein the inter-heartbeat interval is determined by determining an R-R interval of the electrocardiographic signal, further comprising:
establishing a window distinguishing a normal inter-heartbeat interval from a short inter-heartbeat interval for the respective respiratory rate; and
recording a time of inter-heartbeat intervals which is outside the window for the respective respiratory rate.

17. The method according to claim 1, further comprising automatically generating an e911 (enhanced 911) call through a telephone network in response to determining the commencement of the airway restriction or obstruction.

18. The method according to claim 1, wherein said determining an occurrence of the airway restriction or obstruction if a series of inspiratory efforts have an increasing amplitude of inspiratory efforts based on the amplitude of the electromyographic activity signal from muscles of inspiration over time, above the baseline amplitude of inspiratory efforts based on the quantified electromyographic activity from muscles of inspiration, comprises determining if three successive inspiratory efforts have an amplitude of inspiratory effort based on the quantified electromyographic activity from muscles of inspiration above a threshold with at least one of: a steady amplitude of inspiratory effort based on the quantified electromyographic activity from muscles of inspiration and or an increasing amplitude of inspiratory effort based on the quantified electromyographic activity from muscles of inspiration, while an interval between inspiratory efforts is within a normal range.

19. A system for detecting airway restriction or obstruction, comprising:
an input configured to receive a transcutaneous composite bioelectrical signal from a mammal comprising at least one of electromyographic activity of muscles of inspiration of the mammal and components of one of an electrocardiographic signal from a heart of the mammal or an electroencephalographic signal from a brain of the mammal, with an amplifier;
at least one processor configured to:
(a) (1) process the transcutaneous composite bioelectric signal to quantify an amplitude of the electromyographic activity signal from muscles of inspiration within the transcutaneous composite bioelectric with an electronic circuit configured to quantify the amplitude of the electromyographic activity signal from muscles of inspiration signal between at least 300 Hz to 1 kHz,
(2) determine a baseline amplitude of inspiratory efforts based on the quantified amplitude of the electromyographic activity from muscles of inspiration; and
(3) determine an occurrence of the airway restriction or obstruction if a series of inspiratory efforts over time have an increasing amplitude of the electromyographic activity from muscles of inspiration inspiratory effort, above the baseline amplitude of inspiratory efforts; or
(b) (1) determine a baseline inter-heartbeat interval and a normal range of variation for a respective respiratory rate within a respiratory interval from analysis of the transcutaneous composite bioelectric signal;
(2) determine an inter-heartbeat interval and a respiratory rate of a patient from analysis of the transcutaneous composite bioelectric signal;
(3) determine a commencement of a series of inter-heartbeat intervals which is outside the normal range of variation below the baseline inter-heartbeat interval for the respective respiratory rate; and
(4) determine an occurrence of the airway restriction or obstruction if a number of commencements of the series of at least one inter-heartbeat interval, which is below the baseline inter-heartbeat interval for the respective respiratory rate within the respiratory interval, is above a threshold; and
an output for communicating a signal dependent on the determined occurrence of the airway restriction or obstruction.

* * * * *